US008283343B2

(12) United States Patent
Austad et al.

(10) Patent No.: US 8,283,343 B2
(45) Date of Patent: *Oct. 9, 2012

(54) ANSAMYCIN FORMULATIONS AND METHODS OF USE THEREOF

(75) Inventors: Brian C. Austad, Tewksbury, MA (US);
Louis Grenier, Newton, MA (US);
Edward B. Holson, Newton Highlands, MA (US); John J. Lee, Somerville, MA (US); Roger H. Pak, Boxborough, MA (US); James R. Porter, Rowley, MA (US); James L. Wright, Lexington, MA (US)

(73) Assignee: Infinity Pharmaceuticals Inc., Cambridge, MA (US)

( * ) Notice: Subject to any disclaimer, the term of this patent is extended or adjusted under 35 U.S.C. 154(b) by 1080 days.

This patent is subject to a terminal disclaimer.

(21) Appl. No.: 12/229,277

(22) Filed: Aug. 20, 2008

(65) Prior Publication Data

US 2009/0062528 A1 Mar. 5, 2009

Related U.S. Application Data

(63) Continuation of application No. 12/001,239, filed on Dec. 11, 2007, now Pat. No. 7,947,670.

(60) Provisional application No. 60/874,349, filed on Dec. 12, 2006, provisional application No. 60/914,477, filed on Apr. 27, 2007, provisional application No. 60/939,913, filed on May 24, 2007.

(51) Int. Cl.
*A61K 31/27* (2006.01)
*A61K 31/33* (2006.01)
(52) U.S. Cl. ........................................ 514/183; 514/490
(58) Field of Classification Search .................. None
See application file for complete search history.

(56) References Cited

U.S. PATENT DOCUMENTS

| 4,261,989 | A | 4/1981 | Sasaki et al. |
|---|---|---|---|
| 5,387,584 | A | 2/1995 | Schnur |
| 5,834,472 | A | 11/1998 | Sangekar et al. |
| 5,932,566 | A | 8/1999 | Schnur et al. |
| 6,548,555 | B1 | 4/2003 | Curatolo et al. |
| 6,872,715 | B2 | 3/2005 | Santi et al. |
| 6,964,978 | B2 | 11/2005 | Hageman et al. |
| 7,115,279 | B2 | 10/2006 | Curatolo et al. |
| 7,235,260 | B2 | 6/2007 | Crew et al. |
| 7,282,493 | B2 | 10/2007 | Adams et al. |
| 7,361,647 | B2 | 4/2008 | Adams et al. |
| 7,375,217 | B2 | 5/2008 | Adams et al. |
| 7,465,718 | B2 | 12/2008 | Zhang et al. |
| 2002/0009494 | A1 | 1/2002 | Curatolo et al. |
| 2003/0072801 | A1 | 4/2003 | Curatolo et al. |
| 2003/0211144 | A1 | 11/2003 | Tabibi et al. |
| 2003/0219489 | A1 | 11/2003 | Curatolo et al. |
| 2003/0228358 | A1 | 12/2003 | Perlman et al. |
| 2004/0013734 | A1 | 1/2004 | Babcock et al. |
| 2005/0176695 | A1 | 8/2005 | Zhang et al. |
| 2005/0203612 | A1 | 9/2005 | Bhat et al. |
| 2005/0256097 | A1 | 11/2005 | Zhong et al. |
| 2006/0003011 | A1 | 1/2006 | Crew et al. |
| 2006/0014730 | A1 | 1/2006 | Ulm et al. |
| 2006/0019939 | A1 | 1/2006 | Adams et al. |
| 2006/0019941 | A1 | 1/2006 | Adams et al. |
| 2006/0067953 | A1 | 3/2006 | Mansfield et al. |
| 2006/0205705 | A1 | 9/2006 | Ross et al. |
| 2006/0228405 | A1 | 10/2006 | Ulm et al. |
| 2006/0252739 | A1 | 11/2006 | Johnson et al. |
| 2006/0252740 | A1 | 11/2006 | Johnson et al. |
| 2007/0026072 | A1 | 2/2007 | Olsen et al. |
| 2007/0148232 | A1 | 6/2007 | Crew et al. |
| 2009/0042847 | A1 | 2/2009 | Licari et al. |

FOREIGN PATENT DOCUMENTS

| EP | 0577215 | 3/2000 |
|---|---|---|
| EP | 1027887 | 8/2000 |
| EP | 0901786 | 6/2007 |
| GB | 2106111 | 4/1983 |
| WO | WO-93/14215 | 7/1993 |
| WO | WO-95/01342 | 1/1995 |
| WO | WO-98/08490 | 3/1998 |
| WO | 001342 A1 | 1/2000 |
| WO | WO-00/03737 | 1/2000 |
| WO | 008490 A1 | 2/2000 |
| WO | WO-00/37050 | 6/2000 |
| WO | 014215 A2 | 1/2001 |
| WO | 031430 A1 | 1/2003 |
| WO | 037050 A1 | 1/2003 |
| WO | WO-03/013430 | 2/2003 |
| WO | WO-03/026571 | 4/2003 |
| WO | WO-03/066005 | 8/2003 |
| WO | WO-03/086381 | 10/2003 |
| WO | WO-2004/082676 | 9/2004 |
| WO | WO-2005/063714 | 7/2005 |
| WO | WO-2005/095347 | 10/2005 |

(Continued)

OTHER PUBLICATIONS

Buchner, J., "Hsp90—A Holding for Folding" *Trends Biochem. Sci.* (1999) 24:136-141.
Clevenger et al., "Design, Synthesis and Evaluation of a Radicicol and Geldanamycin Chimera, Radamide" *Organic Letters* (2004) 6:4459-4462.
Egorin et al., "Metabolism of 17-(Allylamino)-17-Demethoxygeldanamycin (NSC 330507) by Murine and Human Hepatic Preparations" *Cancer Research* (1998) 58:2385-2396.
Grem et al., "Phase I and Pharmacologic Study of 17-(Allylamino)-17-Demethoxygeldanamycin in Adult Patients with Solid Tumors" *J. Clin. Oncol.* (2005) 23:1805-1893.

(Continued)

Primary Examiner — James D Anderson
Assistant Examiner — Gregg Polansky
(74) Attorney, Agent, or Firm — Nutter McClennen & Fish LLP; Thomas J. Engellenner

(57) ABSTRACT

Amorphous, polymorphic, and solvated forms of 17-amino geldanamycin are disclosed. These compounds are particularly useful for the treatment of cancer, a neoplastic disease state and/or a hyperproliferative disorder, and inhibiting Heat Shock Protein 90 ("Hsp90").

13 Claims, 48 Drawing Sheets
(3 of 48 Drawing Sheet(s) Filed in Color)

FOREIGN PATENT DOCUMENTS

| | | |
|---|---|---|
| WO | WO-2005/112587 | 12/2005 |
| WO | WO-2006/034147 | 3/2006 |
| WO | WO-2006/050457 | 5/2006 |
| WO | WO-2006/089207 | 8/2006 |
| WO | WO-2006/094029 | 9/2006 |
| WO | WO-2006/118953 | 11/2006 |
| WO | WO-2007/001049 | 1/2007 |
| WO | WO-2007/002093 | 1/2007 |
| WO | WO-2007/009007 | 1/2007 |
| WO | WO-2007/053284 | 5/2007 |
| WO | WO-2007/059116 | 5/2007 |
| WO | WO-2007/064926 | 6/2007 |
| WO | WO-2007/084233 A2 | 7/2007 |
| WO | WO-2007/084233 A3 | 7/2007 |

OTHER PUBLICATIONS

Guo et al., "Formation of 17-Allylaminodemethoxygeldanamycin (17-AAG) Hydroquinone by NAD(P)H:Quinone Oxireductase 1: Role of 17-AAG Hydroquinone in Heat Shock Protein 90 Inhibition" *Cancer Research* (2005) 65:10006-10015.

Hancock and Parks, "What is the True Solubility Advantage for Amorphous Pharmaceuticals?" *Pharmaceutical Research* (2000) 17:397-404.

Hancock and Zografi, "Characteristics and Significance of the Amorphous State in Pharmaceutical Systems" *J. Pharm. Sci.* (1997) 86:1-12.

Hu et al., "Isolation and Characterization of Novel Geldanamycin Analogues" *J. Antibiotics* (2004) 57:421-428.

Kelland et al., "DT-Diaphorase Expression and Tumor Cell Sensitivity to 127-Allylamino, 17-Demethyoxygeldanamycin, an Inhibitor of Heat Shock Protein 90" *J. Nat. Can. Inst.* (1999) 91:1940-1949.

Kumar and Mishra, "Analgesic, Anti-Inflammatory and Ulcerogenic Studies of Meloxicam Solid Dispersions in Rodents" *Iranian Journal of Pharmacology and Therapeutics* (2006) 5:77-79.

Konno and Taylor "Ability of Different Polymers to Inhibit Crystallization of Amorphous Felodipine in the Presence of Moisture" *Pharmaceutical Research* (2008) 25:969-978.

Kushida et al., "Improvement of Dissolution and Oral Absorption of ER-34122, A Poorly Water-Soluble Dual 5-Lipoxygenase/Cyclooxygenase Inhibitor with Anti-Inflammatory Activity by Preparing Solid Dispersion" *J. Pharm. Sci.* (2002) 91:258-266.

Lang et al., "Biotransformation of Geldanamycin and 17-Allylamino-17-Demethoxygeldanamycin by Human Liver Microsomes: Reductive Versus Oxidative Metabolism and Implications" *Drug Metabolism and Disposition* (2007) 35:21-29 and *Drug Metabolism and Disposition Fast Forward*, published on Sep. 29, 2006, 40 pages.

Leuner and Dresssman, "Improving Drug Solubility for Oral Delivery Using Solid Dispersions" *Eur. J. Pharm. Biopharm.* (2000) 50:47-60.

Li et al., "Effects of Geldanamycin and Its Derivatives on RNA-Directed DNA Polymerase and Infectivity of Rauscher Leukemia Virus" *Cancer Treatment Reports* (1977) 61:815-824.

Maloney et al., "Hsp90 as a New Therapeutic Target for Cancer Therapy: The Story Unfolds" *Expert Opin. Biol. Ther.* (2002) 2: 3-24.

Marsac et al., "A Comparison of the Physical Stability of Amorphous Felodipine and Nifedipine Systems" *Pharmaceutical Research* (2006) 23:2306-2316.

Mitsiades et al., "Antimyeloma Activity of Heat Shock Protein-90 Inhibition" *Blood* (2006) 107:1092-1100.

Overhoff et al., "Effect of Stabilizer on the Maximum Degree and Extent of Supersaturation and Oral Absorption of Tacrolimus Made by Ultra-Rapid Freezing" *Pharmaceutical Research* (2008) 25:167-175.

Patterson et al., "Preparation of Glass Solutions of Three Poorly Water Soluble Drugs by Spray Drying, Melt Extrusion and Ball Milling" *International Journal of Pharmaceutics* (2007) 336:22-34.

Pignatello et al., "Preparation of Solid Dispersions of Nonsteroidal Anti-inflammaotry Drugs with Acrylic Polymers and Studies on Mechanisms of Drug-Polymer Interactions" *AAPS PharmSciTech* (2002) 3:1-11.

Rutherford et al., "Hsp90 as a Capacitator for Morphological Variation" *Nature* (1998) 396:336-342.

Sasaki et al., "Growth Inhibition of Virus Transformed Cells in Vitro and Antitumor Activity in Vivo of Geldanamycin and its Derivatives" *J. Antibiotics* (1979) 32:849-851.

Schnur et al., "Inhibition of the Oncogene Product p185erB-2 in Vitro and in Vivo by Geldanamycin and Dihydrogeldanamycin Derivatives" *J. Med. Chem.* (1995) 38: 3806-3812.

Serajuddin, "Sold Dispersion of Poorly Water-Soluble Drugs: Early Promises, Subsequent Problems, and Recent Breakthroughs" *J. Pharm. Sci.* (1999) 88:1058-1066.

Smith et al., "Molecular Chaperones: Biology and Prospects for Pharmacological Intervention" *Pharmacol. Rev.* (1998) 50:493-513.

Tantishaiyakul et al., "Properties of Solid Dispersions of Piroxicam in Polyvinylpyrrolidone" *International Journal of Pharmaceutics* (1999) 181:143-151.

Tian et al., "Synthesis and Biological Activities of Novel 17-Aminogeldanamycin Derivatives" *Bioorg. Med. Chem.* (2004) 5317-5329.

Vasconcelos et al., "Solid Dispersions as Strategy to Improve Oral Bioavailability of Poor Water Soluble Drugs" *Drug Discovery Today* (2007) 1-8.

Young et al., "Hsp90: a Specialized but Essential Protein-Folding Tool" *J. Cell Biol.* (2001) 154:267-273.

International Search Report for WO 2007/009007, mailed Mar. 20, 2007.

International Search Report for WO 2007/002093, mailed Feb. 26, 2007.

International Search Report for WO 2005/063714, mailed Apr. 25, 2005.

International Search Report for WO 2007/025317, mailed Jun. 9, 2008.

Chiou et al., "Pharmaceutical Applications of Solid Dispersion Systems"; J. Pharm Sci, (1971) 60:1281-1302.

Shah et al., "Preformulation study of etoposide: II. Increased Solubility and Dissolution Rate by Solid-Solid Dispersions"; Int. J. Pharm, (1995) 113:103-111.

Okimoto et al., "Dissolution Mechanism and Rate of Solid Dispersion Particles of Nilvadipine with Hydroxypropylmethylcellulose"; Int. J. Pharm, (1997) 159:85-93.

Egorin et al., "Pharmacokinetics, Tissue Distribution, and Metabolism of 17-(dimethylaminoethylamino)-17-demethoxygeldanamycin (NSC 707545) in $CD_2F_1$ Mice and Fischer 344 Rats"; Cancer Chemother Pharmacol, (2002) 49:7-19.

Singapore Written Opinion dated Nov. 23, 2010 for application No. 200903908-2.

Kaur et al., "Antiangiogenic Properties of 17-(Dimethylaminoethylamino)-17-Demethoxygeldanamycin: An Orally Bioavailable Heat Shock Protein 90 Modulator"; *Clinical Cancer Research* (2004) 10:4813-4821.

Egorin et al., "Plasma Pharmacokinetics and Tissue Distribution of 17-(Allylamino)-17-Demethoxygeldanamycin (NSC 330507) in CD2F1 Mice1"; *Cancer Chemother Pharmacol* (2001) 47:291-302.

Haaf et al., Polymers of n-vinylpyrrolidone: synthesis, characterization and uses. Polymer Journal. 1985;17(1):143-152.

Honkanen et al., Bioavailability and in vitro oesophageal sticking tendency of hydroxypropyl methylcellulose capsule formulations and corresponding gelatine capsule formulations. Eur J Pharm Sci. Jun. 2002;15(5):479-88.

International Preliminary Report on Patentability mailed Jun. 16, 2009 for Application No. PCT/US2007/025317 (8 pages).

Kai et al., Oral absorption improvement of poorly soluble drug using solid dispersion technique. Chem Pharm Bull (Tokyo). Mar. 1996;44(3):568-71.

Marin et al., Characterization and solubility study of solid dispersions of flunarizine and polyvinylpyrrolidone. Farmaco. Sep. 2002;57(9):723-7.

Tanno et al., Evaluation of hypromellose acetate succinate (HPMCAS) as a carrier in solid dispersions. Drug Dev Ind Pharm. Jan. 2004;30(1):9-17.

Yagi et al., Dissolution behavior of probucol from solid dispersion systems of probucol-polyvinylpyrrolidone. Chemical and Pharmaceutical Bulletin. 1996;44(1):241-244.

|  |  | Cmax (ng/ml) | AUC inf (ng*hr/ml) |
|---|---|---|---|
|  |  | Males | Males |
| Crystalline 17-AG | Uncoated capsules @ 15mpk | 4.5 | CNE |
| 12% 17-AG PVP K30 | Uncoated capsules @ 15mpk | 4760 | 24150 |
|  | Coated capsules @ 15mpk | 3070 | 13485 |

|  |  | Cmax (ng/ml) | AUC inf (ng*hr/ml) |
|---|---|---|---|
|  |  | Females | Females |
| Crystalline 17-AG | Uncoated capsules @ 15mpk | 9 | CNE |
| 12% 17-AG PVP K30 | Uncoated capsules @ 15mpk | 4765 | 24800 |
|  | Coated capsules @ 15mpk | 1460 | 4970 |

In Vitro Dissolution (SIF @ 37°C) of Solid Dispersions of 17-AG (20% load w/w) in Various Polymers Figure 14a
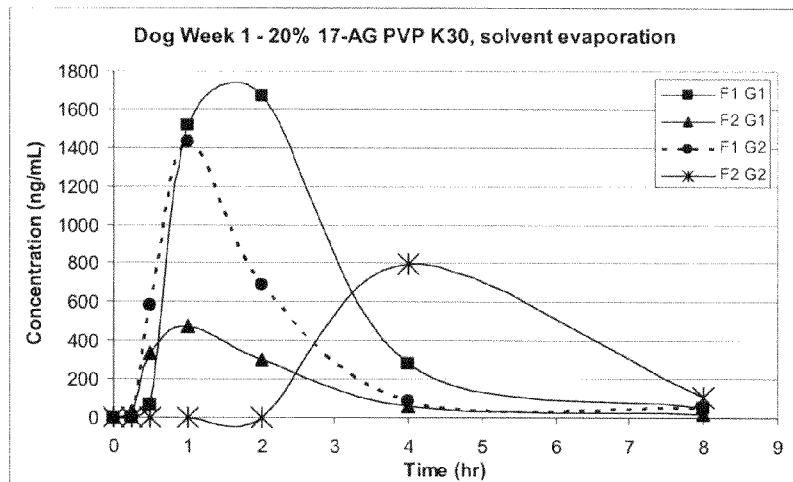
Figure 14b
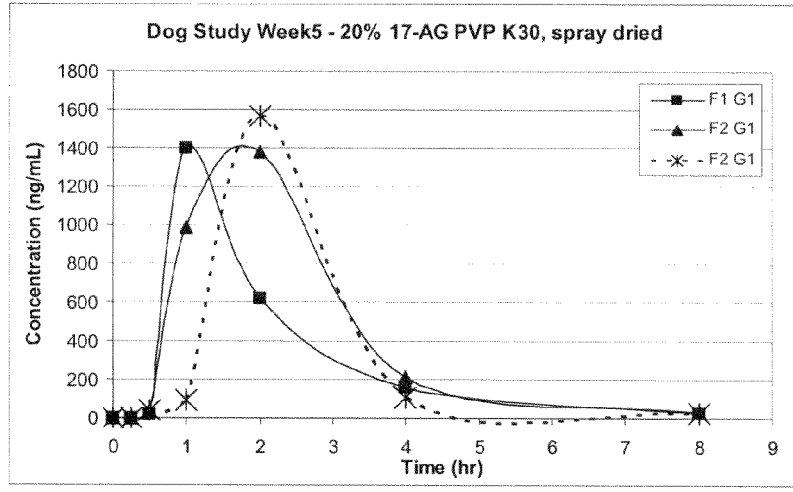
Figure 14c
| Formulation/Dose | Half Life (h) | Tmax (h) | Cmax (ng/ml) | AUC INF (ng*hr/ml) |
|---|---|---|---|---|
| 20% 17-AG PVP K30 solvent evaporation dispersion | 1.5 | 1.8 | 1176.2 | 3153.0 |
| 20% 17-AG PVP K30 spray dried dispersion | 1.2 | 1.7 | 1450.0 | 3011.3 |

Plasma Concentration Time Profile of 17-AG after 15 mg/kg p.o. Dose in Female Beagle Dog to Compare Effect of % 17-AG Load Combined with K-30 PVP

| | | Cmax (ng/ml) | AUC inf (ng*hr/ml) |
|---|---|---|---|
| | | Females | Females |
| 17-AG Load | 12% 17-AG K30 | 13775 | 97386 |
| | 20% 17-AG K30 | 8785 | 73667 |
| | 30% 17-AG K30 | 6725 | 59084 |

Plasma Concentration Time Profile of 17-AG after 15 mg/kg p.o. Dose in Male
Beagle Dog to Compare Effect of % 17-AG Load Combined with K-30 PVP

|  |  | Cmax (ng/ml) | AUC inf (ng*hr/ml) |
|---|---|---|---|
|  |  | Males | Males |
| 17-AG Load | 12% 17-AG K30 | 11100 | 77675 |
|  | 20% 17-AG K30 | 10235 | 65201 |
|  | 30% 17-AG K30 | 6965 | 49517 |

Figure 30a
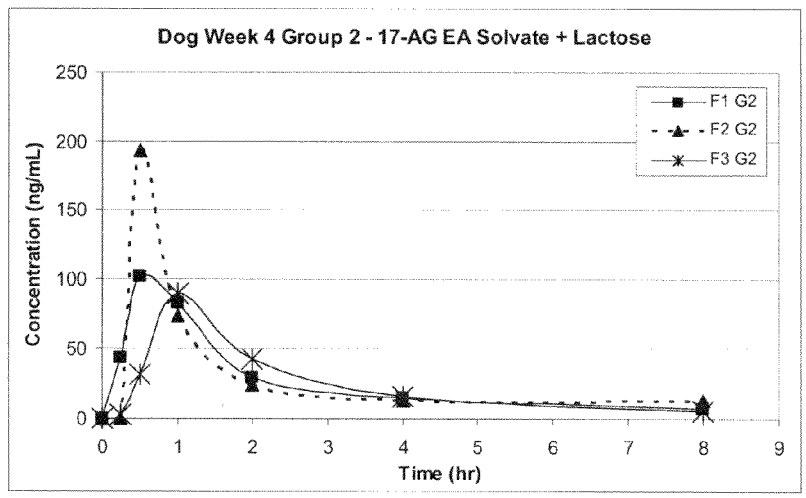
Figure 30b
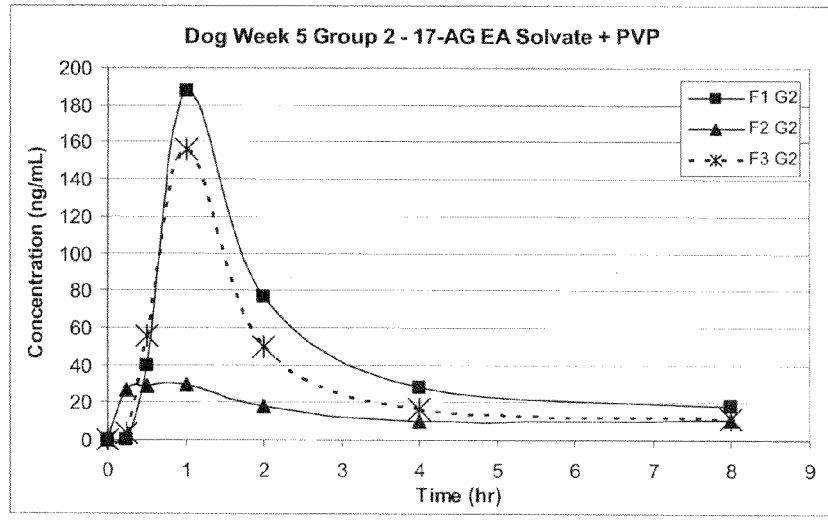
Figure 30c
| Formulation/Dose | Half Life (h) | Tmax (h) | Cmax (ng/ml) | AUC INF (ng*hr/ml) |
|---|---|---|---|---|
| 17-AG Ethyl acetate solvate + lactose | 2.7 | 0.7 | 98.1 | 239.0 |
| 17-AG Ethyl acetate solvate + PVP | 3.2 | 1.0 | 124.4 | 322.2 |

Figure 31a
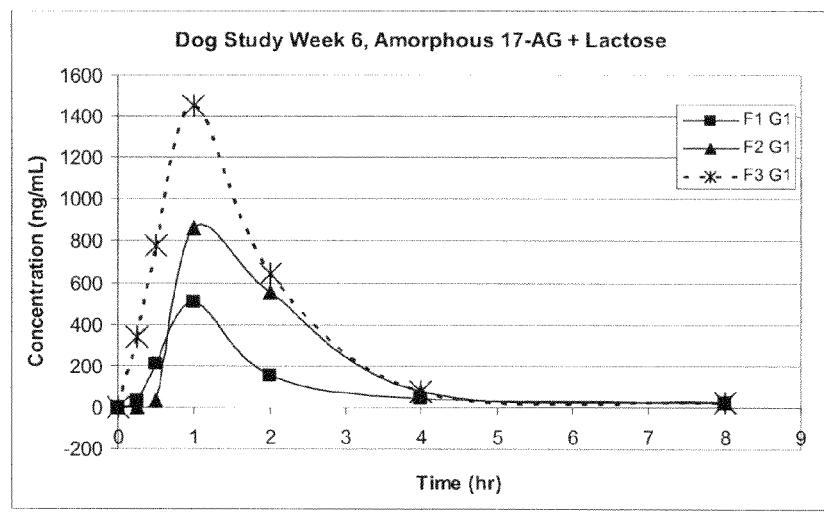
Figure 31b
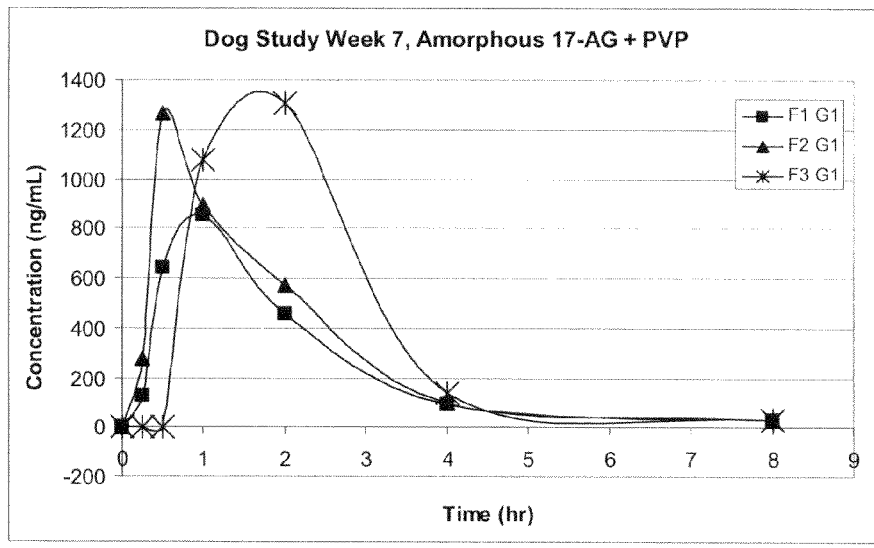
Figure 31c
| Formulation/Dose | Half Life (h) | Tmax (h) | Cmax (ng/ml) | AUC INF (ng*hr/ml) |
|---|---|---|---|---|
| Amorphous 17-AG + lactose | 1.5 | 1.0 | 942.3 | 1854.4 |
| Amorphous 17-AG + PVP | 1.3 | 1.2 | 1141.3 | 2594.2 |

Plasma Concentration of 17-AG in Female Beagles after Oral Dosing at 10 mg/kg with Small and Large Particle Sizes

|  |  | Cmax (ng/ml) |
|---|---|---|
|  |  | Females |
| Particle Size | 20% 17-AG K30 - small | 3050 |
|  | 20% 17-AG K30 - large | 3390 |

|  |  | Cmax (ng/ml) |
|---|---|---|
|  |  | Males |
| Particle Size | 20% 17-AG K30 - small | 1373 |
|  | 20% 17-AG K30 - large | 1116 |

Plasma Concentration Time Profile of 17-AG after 15 mg/kg p.o. Dose in Female Beagle Dog to Compare Effect of PVP Length Combined with 12% 17-AG

|  |  | Cmax (ng/ml) | AUC inf (ng*hr/ml) |
|---|---|---|---|
|  |  | Females | Females |
| PVP Grade | 12% 17-AG K30 | 13775 | 97386 |
|  | 12% 17-AG K15 | 5165 | 35034 |
|  | 12% 17-AG K90 | 4245 | 23800 |

Plasma Concentration Time Profile of 17-AG after 15 mg/kg p.o. Dose in Male Beagle Dog to Compare Effect of PVP Length Combined with 12% 17-AG

| | | Cmax (ng/ml) | AUC inf (ng*hr/ml) |
|---|---|---|---|
| | | Males | Males |
| PVP Grade | 12% 17-AG K30 | 11100 | 77675 |
| | 12% 17-AG K15 | 6415 | 47304 |
| | 12% 17-AG K90 | 4035 | 30254 |

(A)

(B)

(C)

(D)

(E)

(A)

(B)

ANSAMYCIN FORMULATIONS AND METHODS OF USE THEREOF

RELATED APPLICATIONS

This application claims benefit under 35 U.S.C. 119(e) of the filing date of U.S. Ser. No. 60/874,349 filed on Dec. 12, 2006, U.S. Ser. No. 60/914,477 filed on Apr. 27, 2007, and 60/939,913 filed May 24, 2007, the entire disclosure of each of which is incorporated herein by reference.

FIELD

Provided herein are, inter alia, solid forms of geldanamycin analogs, pharmaceutical compositions comprising a geldanamycin analog and a crystallization inhibitor, and methods of making and using such compositions. In some embodiments, provided are methods for the treatment of cancer and/or a hyperproliferative disorder, and methods of inhibiting Heat Shock Protein 90 ("Hsp90").

BACKGROUND

Hsp90 is an abundant protein which has a role in cell viability and which exhibits dual chaperone functions (*J. Cell Biol.* (2001) 154:267-273, *Trends Biochem. Sci.* (1999) 24:136-141). It plays a role in the cellular stress-response by interacting with many proteins after their native conformations have been altered by various environmental stresses, such as heat shock, ensuring adequate protein-folding and preventing non-specific aggregation (*Pharmacological Rev.* (1998) 50:493-513). Recent results suggest that Hsp90 may also play a role in buffering against the effects of mutation, presumably by correcting inappropriate folding of mutant proteins (*Nature* (1998) 396:336-342). Hsp90 also has regulatory roles under normal physiological conditions and is responsible for the conformational stability and maturation of a number of specific client proteins (see. *Expert. Opin. Biol Ther.* (2002) 2(1): 3-24).

Hsp90 antagonists are currently being explored in a large number of biological contexts where a therapeutic effect can be obtained for a condition or disorder by inhibiting one or more aspects of Hsp90 activity.

Geldanamycin is a macrocyclic lactam that is a member of the benzoquinone-containing ansamycin family of natural products. Geldanamycin's nanomolar potency and apparent selectivity for killing tumor cells, as well as the discovery that its primary target in mammalian cells is Hsp90, has stimulated interest in its development as an anti-cancer drug. However, its extremely low solubility and the association of hepatotoxicity with the administration of geldanamycin have led to difficulties in developing an approvable agent for therapeutic applications. In particular, geldanamycin has poor water solubility, making it difficult to deliver in therapeutically effective doses.

More recently, attention has focused on 17-amino derivatives of geldanamycin ("geldanamycin analogs"), in particular 17-AAG, showing reduced hepatotoxicity while maintaining Hsp90 binding. See U.S. Pat. Nos. 4,261,989; 5,387,584; and 5,932,566. Like geldanamycin, these 17-amino derivatives have very limited aqueous solubility. Consequently, there is an unmet need to develop additional pharmaceutical compositions of geldanamycin analogs, such as 17-AG and 17-AAG, and solid forms thereof.

SUMMARY

In one embodiment, provided herein are solid forms of geldanamycin analogs, which are useful as Hsp90 antagonists. Also provided herein, among other things, are pharmaceutical compositions comprising geldanamycin analogs, methods for making such compositions having enhanced bioavailability, methods of using gelanamycin analogs for the treatment of cancer and/or a hyperproliferative disorder, and methods of inhibiting Hsp90. It has been discovered herein that mixtures of geldanamycin analogs and crystallization inhibitors dramatically improve the bioavailability of geldanamycin analogs. Examples of formulations that achieve this improvement include, but are not limited to, solid dispersions, solid molecular dispersions, and physical blends of the components. In some embodiments, a geldanamycin analog is present in an amorphous state, a microcrystalline state, a nanocrystalline state, or any combination thereof.

In certain embodiments, pharmaceutical compositions containing a solid dispersion of a geldanamycin analog and at least one crystallization inhibitor are provided wherein the geldanamycin analog is present in substantially amorphous form. In other embodiments, a method for the preparation of amorphous geldanamycin analogs is provided. One method for producing a solid molecular dispersion of amorphous geldanamycin analogs provided herein involves solvent spray drying. Other techniques that can be used to prepare solid molecular dispersions of amorphous geldanamycin analogs include, without limitation: (1) milling; (2) extrusion; (3) melt processes, including high melt-congeal processes and melt-congeal processes; (4) solvent modified fusion; (5) solvent processes, including spray coating, lyophilization, solvent evaporation (e.g., rotary evaporation) and spray-drying; and (6) non-solvent precipitation.

In another embodiment, provided are amorphous geldanamycin analogs that can exist within a solid amorphous dispersion as a pure phase, as a molecular dispersion of geldanamycin analog homogeneously distributed throughout a crystallization inhibitor or any combination of these states or those states that lie intermediate between them. In some embodiments, a dispersion is substantially homogeneous such that an amorphous geldanamycin analog is dispersed uniformly throughout the dispersion or formulation.

In yet another embodiment, provided are geldanamycin analogs that exist in a variety of solid forms. In certain embodiments, 17-AG exists in more than one polymorphic form. Provided are 17-AG compositions that include such forms, whether in a pure polymorphic state or admixed with any other material, including for example, another polymorphic form of 17-AG.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 10a depicts a graph of 17-AG concentration levels, plotted as a function of ng/ml versus time (hours), demonstrating higher relative bioavailability with the administration of amorphous 17-AG as compared to crystalline 17-AG in male beagle dogs in: (i) an uncoated HPMC capsule containing 17-AG (12% load) in a PVP solid dispersion formulation (Session 1); (ii) an uncoated HPMC capsule containing a crystalline 17-AG (Session 3); and (iii) a coated HPMC capsule containing 17-AG (12% load) in a PVP solid dispersion formulation (Session 4).

FIG. 10b depicts a summary table of PK parameters for FIG. 10a.

FIG. 11a depicts a graph of 17-AG concentration levels, plotted as a function of ng/ml versus time (hours), demonstrating higher relative bioavailability with the administration of amorphous 17-AG as compared to crystalline 17-AG in female beagle dogs in: (i) an uncoated HPMC capsule containing 17-AG (12% load) in a PVP solid dispersion formulation (Session 1); (ii) an uncoated HPMC capsule containing a crystalline 17-AG (Session 3); and (iii) a coated HPMC capsule containing 17-AG (12% load) in a PVP solid dispersion formulation (Session 4).

FIG. 11b depicts a summary table of PK parameters for FIG. 11a.

FIG. 14 depicts a graph of 17-AG concentration levels, plotted as a function of ng/ml versus time (hours), demonstrating relative bioavailability of 17-AG in female beagle dogs using: solid dispersion formulations made by two different methods, plotted as a function of ng/ml versus time (hours): (FIG. 14a) an uncoated HPMC capsule containing 17-AG (20% load) in a PVP solid amorphous dispersion formulation made by rotary evaporation; and (FIG. 14b) an uncoated HPMC capsule containing 17-AG (20% load) in a PVP solid amorphous dispersion formulation made by spray drying.

FIG. 14c depicts a summary table of the data in FIG. 14a and FIG. 14b.

FIG. 28a depicts a graph demonstrating effects of varying loads of 17-AG (12%, 20% and 30% loads (w/w) in PVP K-30) on plasma level concentration of 17-AG in female beagle dogs, plotted as a function of ng/ml versus time (minutes). FIG. 28b is a summary table of the data in FIG. 28a.

FIG. 29a depicts a graph demonstrating effects of varying loads of 17-AG (12%, 20% and 30% loads (w/w) in PVP K-30) on plasma level concentration of 17-AG in male beagle dogs, plotted as a function of ng/ml versus time (minutes).

FIG. 29b depicts a summary table of the data in FIG. 29a.

FIG. 30a depicts a graph of 17-AG dog plasma level concentration after administration of an uncoated HPMC capsule containing a physical blend of an EtOAc Solvate of 17-AG and lactose, without a crystallization inhibitor present, plotted as a function of ng/ml versus time (hours).

FIG. 30b depicts a graph of 17-AG dog plasma level concentration after administration of an uncoated HPMC capsule containing a physical blend of an EtOAc Solvate of 17-AG and a crystallization inhibitor (PVP), plotted as a function of ng/ml versus time (hours) demonstrating that adding a crystallization inhibitor leads to increased plasma level concentration.

FIG. 30c depicts a summary table of the PK parameters for FIG. 30a and FIG. 30b.

FIG. 31a depicts a graph of 17-AG dog plasma level concentration after administration of an uncoated HPMC capsule containing amorphous 17-AG and lactose, without a crystallization inhibitor present, plotted as a function of ng/ml versus time (hours), demonstrating that even when no crystallization inhibitor is present, the plasma level concentration is high, relative to crystalline 17-AG.

FIG. 31b depicts a graph of 17-AG dog plasma level concentration after administration of an uncoated HPMC capsule containing amorphous 17-AG and a crystallization inhibitor (PVP), plotted as a function of ng/ml versus time (hours), demonstrating that adding a crystallization inhibitor leads to increased plasma level concentration.

FIG. 31c depicts a summary table of the PK parameters for FIG. 31a and FIG. 31b.

FIG. 40a depicts a graph of plasma concentration in female beagle dogs after oral dosing (10 mg/kg) of 17-AG (20% load) plus PVP in a solid dispersion formulation [both small (<50 μM) and large (>800 μM) particle sizes], plotted as a function of ng/ml versus time (minutes) demonstrating that particle size does not greatly affect in-vivo exposure.

FIG. 40b depicts a summary table of the PK parameters for FIG. 40a.

FIG. 40c depicts a summary table of the PK parameters for a graph of plasma concentration in male beagle dogs after oral dosing (10 mg/kg) of 17-AG (20% load) plus PVP in a solid dispersion formulation [both small (less than 50 microns) and large (greater than 800 microns) particle sizes], plotted as a function of ng/ml versus time (minutes).

FIG. 41a depicts a graph of 17-AG (12% load) plasma concentration in female beagle dogs after oral dosing (15 mg/kg) of amorphous 17-AG dispersions using various grades of PVP (K-15, K30 and K-90), plotted as a function of ng/ml versus time (hours) demonstrating a trend. From the data, PVP grade K-30 provides greater exposure than PVP K-15 which provides greater exposure than PVP K-90.

FIG. 41b depicts a summary table of the PK parameters for FIG. 41a.

FIG. 42a depicts a graph of 17-AG (12% load) plasma concentration in male beagle dogs after oral dosing (15 mg/kg) of amorphous 17-AG dispersions using various grades of PVP (K-15, K30 and K-90), plotted as a function of ng/ml versus time (hours). Similar to the data from female dog dosing, PVP grade K-30 provides greater exposure than PVP K-15 which provides greater exposure than PVP K-90.

FIG. 42b depicts a summary table of the PK parameters for FIG. 42a.

DETAILED DESCRIPTION (1) Definitions and Abbreviations

Figure 1:
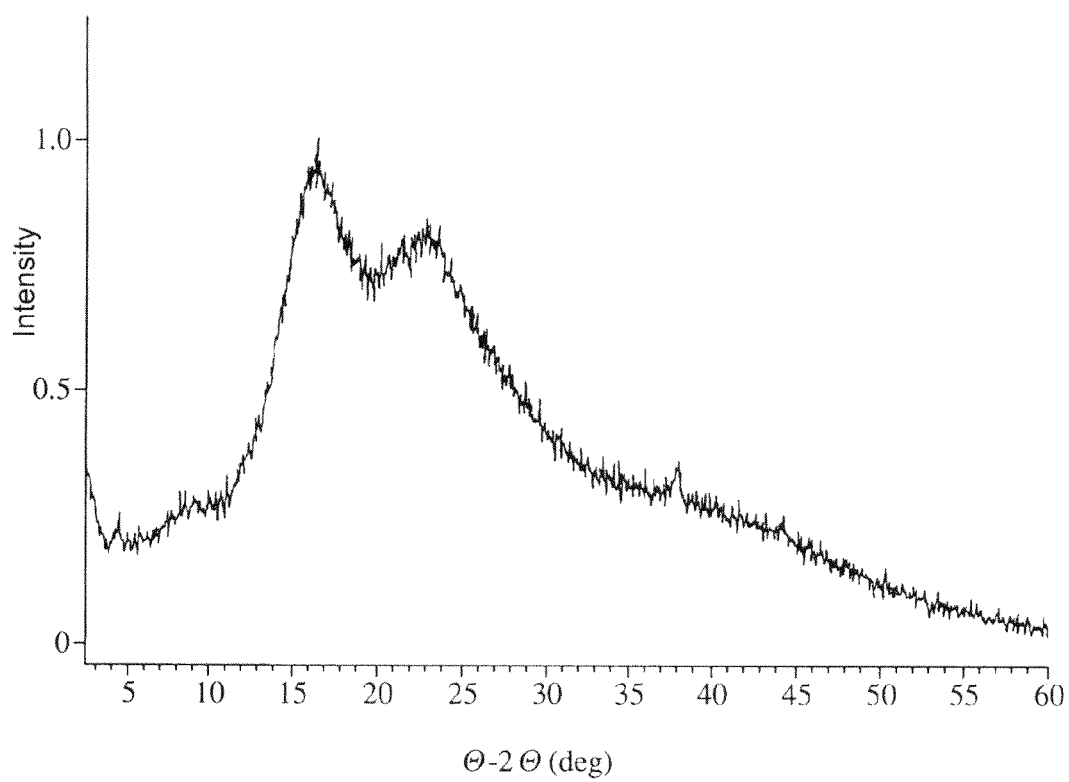
FIG. 1 depicts an XRPD pattern for amorphous 17-AG.

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

Where stereochemistry is not specifically indicated, all stereoisomers of the inventive compounds provided herein are included within the scope of this disclosure, as pure isomers as well as mixtures thereof. Unless otherwise indicated, individual enantiomers, diastereomers, geometrical isomers, and combinations and mixtures thereof are all encompassed by the present disclosure. Polymorphic crystalline forms and solvates are also encompassed within the scope of this disclosure.

The term "acylamino" and "acylamine" refers to a moiety that may be represented by the general formula:

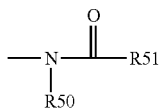

wherein each of R50 and R51 independently represent a hydrogen, an alkyl, an alkenyl or —(CH$_2$)$_m$—R61; wherein R61 represents an aryl, a cycloalkyl, a cycloalkenyl, a heterocycle or a polycycle; and m is zero or an integer in the range of 1 to 8; or R50 and R51, taken together with the N atom to which they are attached complete a heterocycle having from 4 to 8 atoms in the ring structure.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{30}$ for straight chain, $C_3$-$C_{30}$ for branched chain), 20 or fewer. In some embodiments, certain cycloalkyls have from 3-10 carbon atoms. In some embodiments, an alkyl group contains 1-10 carbon atoms as its backbone, and may be substituted. In some embodiments, certain cycloalkyls have from 3-10 carbon atoms in their ring structure, and others have 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. In some embodiments, "lower alkenyl" and "lower alkynyl" have similar chain lengths from two to about ten carbons, alternatively from two to about six carbon atoms in its backbone structure.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "aralkyl" is art-recognized and refers to an alkyl group substituted with an aryl group (e.g., an aromatic or heteroaromatic group). Benzyl, p-methoxybenzyl, and phenylethyl are examples of an aralkyl.

The terms "alkenyl" and "alkynyl" refer to unsaturated aliphatic groups analogous in length and possible substitution to the alkyls described above, but that contain at least one double or triple bond respectively. Alkenyl and alkynyl groups may be substituted with the same groups that are suitable as substituents on alkyl groups, to the extent permitted by the available valences. In certain embodiments, alkenyl and alkynyl groups contain 2-10 carbons in the backbone structure.

The terms "alkoxyl" or "alkoxy" refers to an alkyl group, as defined herein, having an oxygen radical attached thereto. In one embodiment, alkoxyl groups include methoxy, ethoxy, propyloxy, tert-butoxy and the like. The alkyl portion of an alkoxy group is sized like the alkyl groups, and can be substituted by the same groups that are suitable as substituents on alkyl groups, to the extent permitted by the available valences.

The term "amido" and "amide" are art recognized as an amino-substituted carbonyl and includes a moiety that may be represented by the general formula:

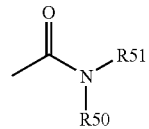

wherein R50 and R51 are as defined herein.

The terms "amine" and "amino" are art-recognized and refer to both unsubstituted and substituted amines, e.g., a moiety that may be represented by the general formulas:

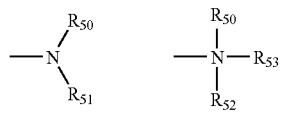

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "aralkyl" as used herein, whether alone or as part of a group name such as, for example, aralkyloxy, refers to an alkyl group as described herein substituted with an aryl group as described herein (e.g., an aromatic or heteroaromatic group). The aryl portion of each aralkyl group may be optionally substituted. In one embodiment, aralkyl groups include, for example, groups of general formula Ar—(CH$_2$)$_t$—, where Ar represents an aromatic or heteroaromatic ring and t is an integer from 1-6.

The term "aryl" as used herein, whether alone or as part of another name as in 'aryloxy', refers to 5-, 6- and 7-membered single-ring aromatic groups that may include from zero to four heteroatoms selected from N, O and S, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

As used herein, the term "benzoquinone ansamycin" (aka "geldanamycin compound") means a macrocyclic lactam ring system containing: (a) one amide bond; and (b) a benzoquinone moiety, wherein said benzoquinone moiety bears 0-2 nitrogen substituents that are exo- to the macrocyclic lactam ring system, and the benzoquinone moiety itself. Specific examples of naturally-occurring benzoquinone ansamycins include, but are not limited to, geldanamycin and herbimycin.

The phrase "characteristic XRPD peaks" or "characteristic set of peaks" means a single peak or set of peaks taken from an XRPD spectra that distinguish a polymorph from other known polymorphs of the same compound identified by comparison of XRPD patterns from different forms.

The term "crystallization inhibitor" means a pharmaceutically acceptable excipient which substantially inhibits the conversion of a compound from the amorphous form to one or more crystalline forms in the solid state or in solution. A crystallization inhibitor may also substantially inhibit crystal growth in the gastrointestinal tract for long enough (e.g., about 1 to 6 hours) to allow for enhanced absorption of at least 50%, over conventional delivery, of the compound into the bloodstream.

The term "geldanamycin analog" refers to a benzoquinone ansamycin other than geldanamycin, for example, 17-amino-geldanamycin (17-AG), 17-allylamino-17-demethoxygeldanamycin (17-AAG) or 17-(2-dimethylaminoethyl) amino-17-demethoxygeldanamycin (17-DMAG).

The term "heterocycloalkyl" refers to cycloalkyl groups as described herein, wherein at least one carbon atom of the alkyl or cycloalkyl portion is replaced by a heteroatom selected from N, O and S.

The term "heteroatom" is art-recognized and refers to an atom of any element other than carbon or hydrogen. Illustrative heteroatoms include boron, nitrogen, oxygen, phosphorus, sulfur and selenium.

The terms "heterocyclyl", "heteroaryl", "heterocyclic ring" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described herein, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "Hsp90 mediated disorder" or "disorder mediated by cells expressing Hsp90" refers to pathological and disease conditions in which Hsp90 plays a role. Such roles can be directly related to the pathological condition or can be indirectly related to the condition. The common feature to this class of conditions is that the condition can be ameliorated by inhibiting the activity, function, or association with other proteins of Hsp90. Particular exemplary Hsp90 mediated disorders are discussed, infra.

As used herein, the term "isolated" in connection with a compound provided herein means the compound is not in a cell or organism and the compound is separated from some or all of the components that typically accompany it in nature.

The term "molecular dispersion" as used herein refers to a type of solid dispersion wherein one component is dispersed throughout another component such that the system is chemically and physically uniform and homogeneous throughout. These systems are substantially free of active ingredients in their crystalline or microcrystalline state as evidenced by thermal analysis (e.g., differential scanning calorimetry), diffractive (e.g., X-ray diffraction), or imaging (polarized light microscopy) techniques.

The term "pharmaceutically acceptable salt" or "salt" refers to a salt of one or more compounds. Suitable pharmaceutically acceptable salts of compounds include acid addition salts which may, for example, be formed by mixing a solution of the compound with a solution of a pharmaceutically acceptable acid, such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical-Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of provided herein, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group", as used herein means that a particular functional moiety, e.g. O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group must be selectively removed in good yield by readily available, preferably non-toxic reagents that do not attack the other functional groups; the protecting group may form an easily separable derivative (without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary protecting groups include esters of carboxylic acids, silyl ethers of alcohols, and acetals and ketals of aldehydes and ketones, respectively. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "*Protective Groups in Organic Synthesis*" Third Ed. Greene, T. W. and Wuts, P. G., Eds., John Wiley & Sons, New York: 1999, the entire contents of which are hereby incorporated by reference.

The term "polymorph" refers to different crystal structures achieved by a particular chemical entity. Specifically, polymorphs occur when a particular chemical compound can crystallize with more than one structural arrangement.

The term "solvate" refers to a crystal form where a stoichiometric or non-stoichiometric amount of solvent, or mixture of solvents, is incorporated into the crystal structure.

The term "subject" as used herein, refers to an animal, typically a mammal or a human, that will be or has been the object of treatment, observation, and/or experiment. When the term is used in conjunction with administration of a compound or drug, then the subject has been the object of treatment, observation, and/or administration of the compound or drug.

The term "substantially amorphous" when used to describe a composition disclosed herein means that the majority of the compound present in a composition is present in amorphous form and that the composition has less than about 20% crystalline compound, less than about 15% crystalline compound, less than about 10% crystalline compound, less than about 5% crystalline compound, less than about 3% crystalline compound, or less than about 1% crystalline compound, less than about 0.1% crystalline compound, or less than about 0.01% crystalline compound. In some embodiments of the present invention, the compound present in a composition contains no detectable crystalline material. When the term "substantially amorphous" is used to describe a compound disclosed herein it means that the majority of the compound is present in amorphous form and the compound has less than about 20% crystalline content, less than about 15% crystalline content, less than about 10% crystalline content, less than about 5% crystalline content, less than about 3% crystalline content, or less than about 1% crystalline content, less than about 0.1% crystalline content, or less than about 0.01% crystalline content. In some embodiments of the present invention, the compound present in a composition contains no detectable crystalline material.

The term "substantially free of", when used to describe a material or compound, means that the material or compound lacks a significant or detectable amount of a designated substance. In some embodiments, the designated substance is present at a level not more than about 1%, 2%, 3%, 4% or 5% (w/w or v/v) of the material or compound. For example, a preparation of a particular geldanamycin analog is "substantially free of" other geldanamycin analogs if it contains less than about 1%, 2%, 3%, 4% or 5% (w/w or v/v) of any geldanamycin analog other than the particular geldanamycin analog designated. Similarly, in some embodiments of the present invention, a preparation of amorphous geldanamycin is "substantially free of" crystalline geldanamycin if it contains less than about 1%, 2%, 3%, 4% or 5% (w/w or v/v) crystalline geldanamycin. In some embodiments of the present invention, the preparation of amorphous geldanamycin contains no detectable crystalline geldanamycin. Similarly, in some embodiments of the present invention a preparation of amorphous 17-AG is "substantially free of" crystalline 17-AG if it contains less than about 1%, 5%, 10% or 15% (w/w or v/v) crystalline 17-AG. Similarly, in some embodiments of the present invention a preparation of amorphous 17-AAG is "substantially free of" crystalline 17-AAG if it contains less than about 1%, 5%, 10% or 15% (w/w or v/v) crystalline 17-AAG. Similarly, in some embodiments of the present invention, a preparation of an EtOAc solvate is "substantially free of" other solid forms of 17-AG if it contains less than about 1%, 5%, 10% or 15% (w/w or v/v) of any solid form other than the solid form designated. Similarly, in some embodiments of the present invention, a preparation of an EtOAc solvate is "substantially free of" other solid forms of 17-AAG if it contains less than about 1%, 5%, 10% or 15% (w/w or v/v) of any solid form other than the solid form designated.

The phrase "substantially all" when used to describe XRPD peaks of a compound means that the XRPD of that compound includes at least about 80% of the peaks when compared to a reference. For example, when an XRPD of a compound is said to include "substantially all" of the peaks in a reference list, or all of the peaks in a reference XRPD, it means that the XRPD of that compound includes at least 80% of the peaks in the specified reference. In other embodiments, the phrase "substantially all" means that the XRPD of that compound includes at least about 85, 90, 95, 97, 98, or 99% of the peaks when compared to a reference. Additionally, one skilled in the art will appreciate throughout, that XRPD peak intensities and relative intensities as listed herein may change with varying particle size and other relevant variables.

The term "substantially homogeneous" means that the geldanamycin analog is dispersed evenly throughout the dispersion or formulation. Thus, a portion of a dispersion that is 10% by weight of the dispersion should contain 8-12% or 9-11% by weight of the geldanamycin analog present in the dispersion.

The term "substantially inhibit" as used herein means to reduce significantly. For example, a crystallization inhibitor that inhibits conversion of an amorphous compound to one or more crystalline forms of the compound in the solid state (e.g., that "substantially inhibits" that conversion if it reduces conversion to less than about 1%, to less than about 5%, to less than about 10%, to less than about 15%, to less than about 20%, or less than about 25% crystalline material) for a period of about 1 hour or greater, about 3 hours or greater, about 6 hours or greater, about 12 hours or greater, about 1 day or greater, about 1 week or greater, about one month or greater, about 3 months or greater, about 6 months or greater, or about one year or greater.

The term "substituted" refers to a chemical group, such as alkyl, cycloalkyl aryl, and the like, wherein at least one hydrogen is replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "substituted" is also contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described herein above. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. In many embodiments, however, any single substituent has fewer than the 100 total atoms.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The definition of each expression, e.g. alkyl, m, n, and the like, when it occurs more than once in any structure, is intended to be independent of its definition elsewhere in the same structure.

The term "sugar" as used herein refers to a natural or an unnatural monosaccharide, disaccharide, oligosaccharide, or polysaccharide comprising one or more triose, tetrose, pentose, hexose, heptose, octose, and nonose saccharides. Sugars may include alditols resulting from reduction of the saccharide carbonyl group; aldonic acids resulting from oxidation of one or more terminal groups to carboxylic acids of the saccharide; deoxy sugars resulting from replacement of one or more hydroxyl group(s) by a hydrogen in the saccharide; amino sugars resulting from replacement of one or more hydroxyl group(s) by an amino group in the saccharide; thio sugars resulting from replacement of one or more hydroxyl group(s) by a thiol group, or other analogous compounds resulting from the replacement of, for example, one or more hydroxyl group(s) by an acylamino group, a sulfate group, a phosphate group, or similar heteroatomic group; or any combination of the foregoing modifications. The term sugar also includes analogs of these compounds (i.e., sugars that have been chemically modified by acylation, alkylation, and formation of glycosidic bonds by reaction of sugar alcohols with aldehydes or ketones, etc). Sugars may be present in cyclic (oxiroses, oxetosesm furanoses, pyranoses, septanoses, octanoses, etc) form as hemiacetals, hemiketals, or lactones; or in acyclic form. The sacharides may be ketoses, aldoses, polyols and/or a mixture of ketoses, aldoses and polyols. Sugars may include, but are not limited to glycerol, polyvinylalcohol, propylene glycol, sorbitol, ribose, arabinose, xylose, lyxose, allose, altrose, mannose, mannitol, gulose, dextrose, idose, galactose, talose, glucose, fructose, dextrates, lactose, sucrose, starches (i.e., amylase and amylopectin), sodium starch glycolate, cellulose and cellulose derivatives (i.e., methylcellulose, hydroxypropyl celluloe, hydroxyethyl cellulose, hydroxyethylmethyl cellulose, carboxymethyl cellulose, cellulose acetate, cellulose acetate phthalate, croscarmellose, hypomellose, and hydroxypropyl methyl cellulose), carrageenan, cyclodextrins, dextrin, polydextrose, and trehalose.

The term "supersaturated" means that a solution has a concentration of dissolved solute that is higher than the concentration of that same solute at equilibrium solubility in a given solvent at a given temperature.

The phrase "therapeutically effective amount" as used herein, means an amount sufficient to elicit a desired biological or medicinal response in a cell culture, tissue system, animal, or human. In some embodiments, the response includes alleviation and/or delay of onset of one or more symptoms of the disease, condition, or disorder being treated.

The phrase "taken together form a bond," when used to refer to two chemical groups means that, if the groups are attached to atoms that are not otherwise directly bonded to each other, they represent a bond between the atoms to which they are attached. If the groups are on atoms that are directly bonded to each other, they represent an additional bond between those two atoms. Thus, for example, when $R^5$ and $R^6$ taken together form a bond, the structure —CH($R^5$)—CH($R^6$)— represents —C(H)=C(H)—.

Certain compounds contained in compositions disclosed herein may exist in particular geometric or stereoisomeric forms. Unless otherwise indicated, the present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of this disclosure. Additional asymmetric carbon atoms may be present in a substituent such as an alkyl group. All such isomers, as well as mixtures thereof, are intended to be included in this disclosure.

(2) Solid Forms

Provided herein are geldanamycin analogs that can exist in a variety of solid forms. Such forms include neat crystal forms, known as polymorphs. Such solid forms also include solvates, hydrates, anhydrous forms and amorphous. Such solid forms of geldanamycin analogs are contemplated as within this disclosure. In certain embodiments, provided is a geldanamycin compound as a mixture of one or more different solid forms (e.g., polymorphs, solvates and amorphous geldanamycin analogs) of 17-AG and/or 17-AAG.

Provided herein is 17-AG as an amorphous solid, referred to herein as amorphous 17-AG, and substantially free of other geldanamycin analogs. In some embodiments, amorphous 17-AG is substantially free of other solid forms of 17-AG. Amorphous solids are well known to one of ordinary skill in the art and are typically prepared by such methods as lyophilization, melting, and precipitation from supercritical fluid, among others. Methods of preparing amorphous 17-AG are described in the Examples section, infra.

In some embodiments, amorphous 17-AG is characterized in that it has an XRPD pattern similar to that depicted in FIG. 1.

In certain embodiments, provided is substantially amorphous 17-AG substantially free of crystalline forms of 17-AG.

Provided herein are at least three polymorphic forms, referred to herein as Form I, Form II and Form III, of 17-AG.

In certain embodiments, provided is Form I of 17-AG. In some embodiments, provided is Form I of 17-AG characterized in that it has a peak in its XRPD patterns at the specified peaks ± about 0.3 degrees 2-theta. As used herein, the term "about", when used in reference to any degree 2-theta value recited, refers to the stated value ±0.3 degree 2-theta in accordance with the value's reported decimal place.

Figure 2:
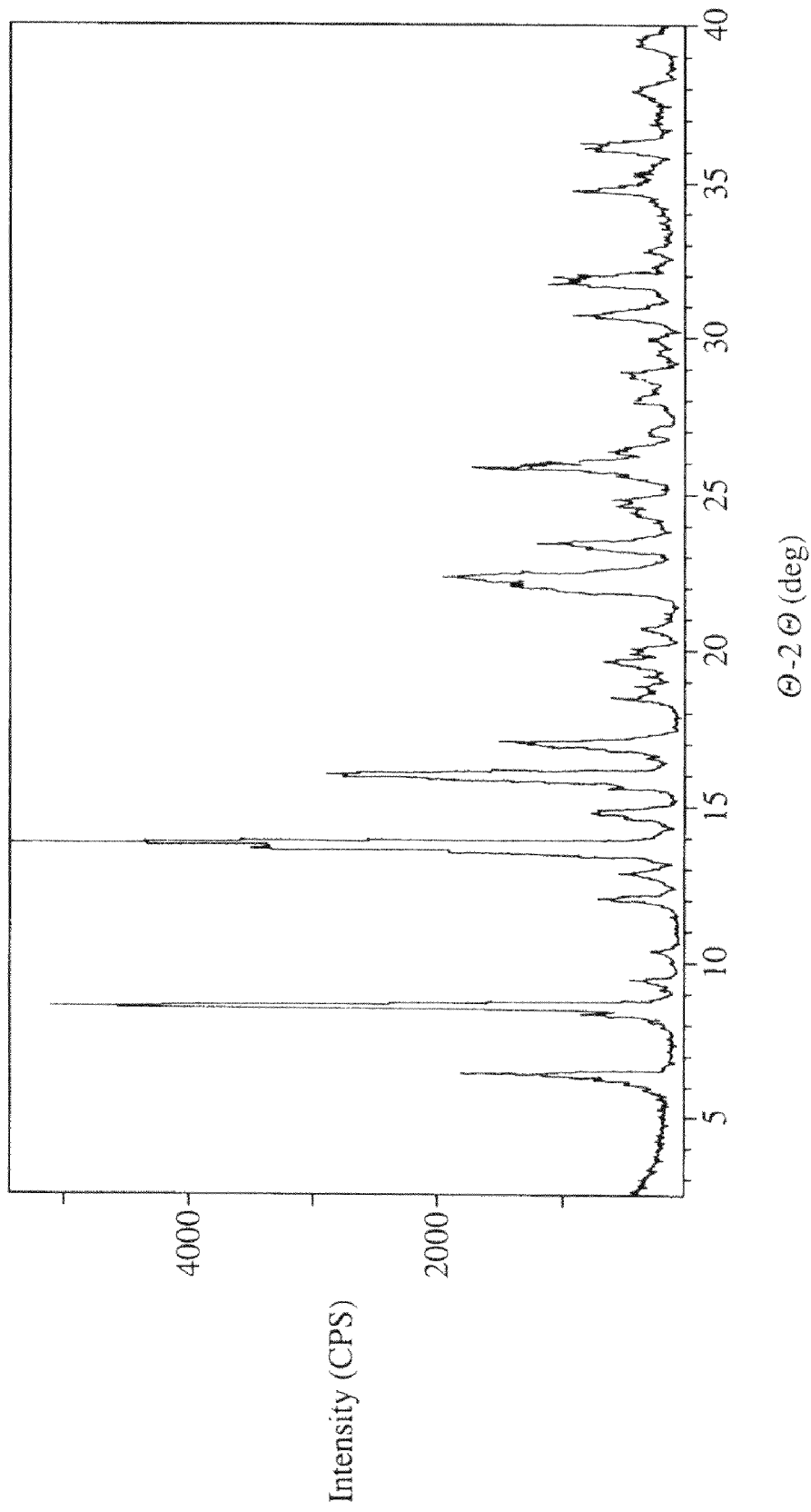
FIG. 2 depicts an XRPD pattern for Form I of 17-AG.

In certain embodiments, provided is Form I of 17-AG substantially free of other geldanamycin analogs. In some embodiments, Form I of 17-AG is substantially free of other solid forms of 17-AG. In some embodiments, Form I is characterized by representative peaks in its XRPD pattern selected from those at about 6.2, 8.5, 13.6, 15.9, 16.9, 22.4, 23.4, 26.3, 30.6, 31.7, 35.1 and 36.1 degrees 2-theta, and combinations thereof. In some embodiments, Form I is characterized in that it has at least one peak selected from those at about 6.2, 8.5 13.6 and 15.9 degrees 2-theta. In some embodiments, Form I is characterized by at least one representative peak in its XRPD pattern selected from those at about 6.2, 8.5, 13.6 and 15.9, in combination with at least one other peak selected from those at about 6.2, 8.5, 13.6, 15.9, 16.9, 22.4, 23.4, 26.3, 30.6, 31.7, 35.1 and 36.1 degrees 2-theta. In some embodiments, Form I of 17-AG is characterized in that it has substantially all peaks in its XRPD pattern shown in FIG. 2.

Figure 3:
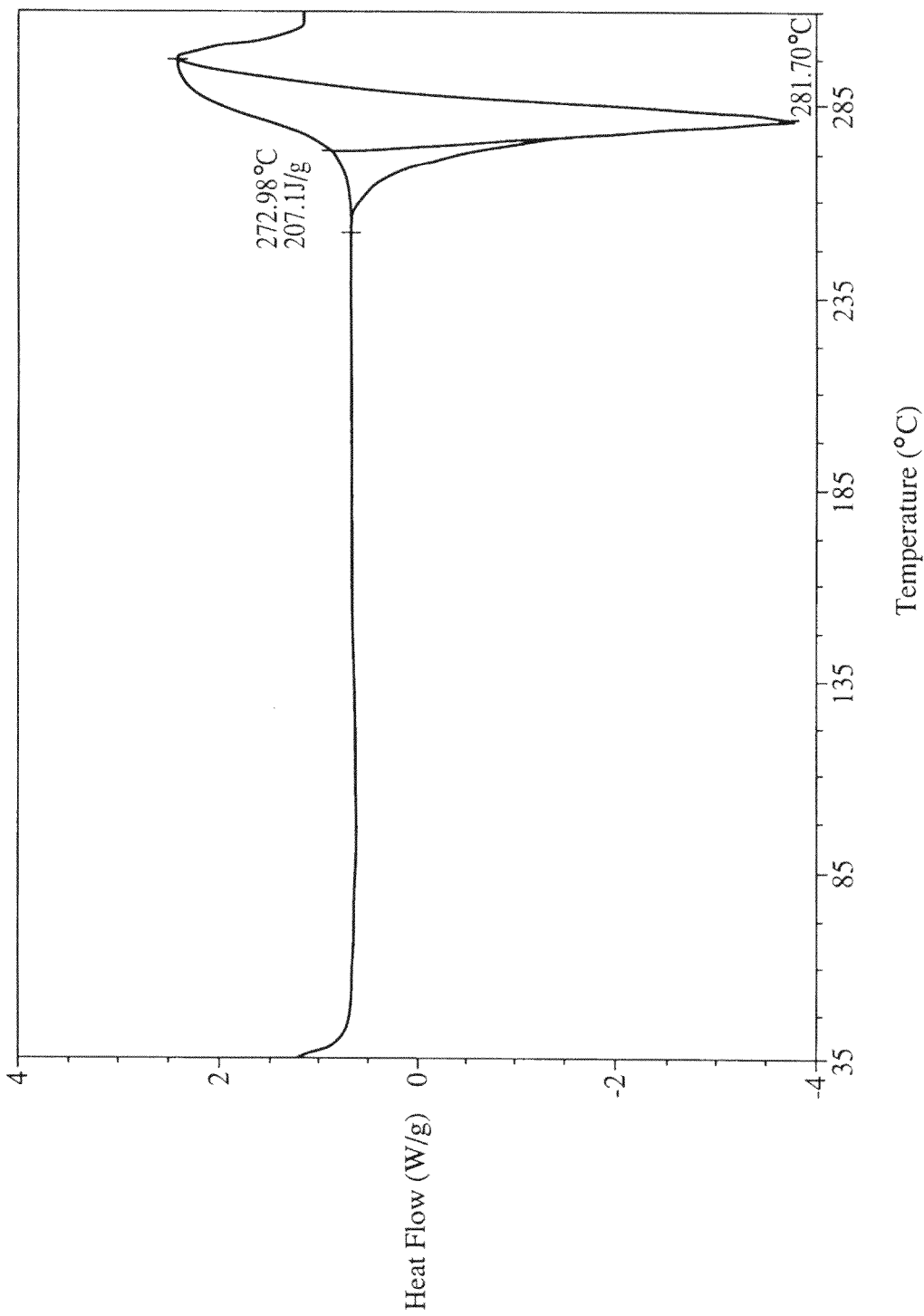
FIG. 3 depicts a DSC pattern for Form I of 17-AG.
Figure 4:
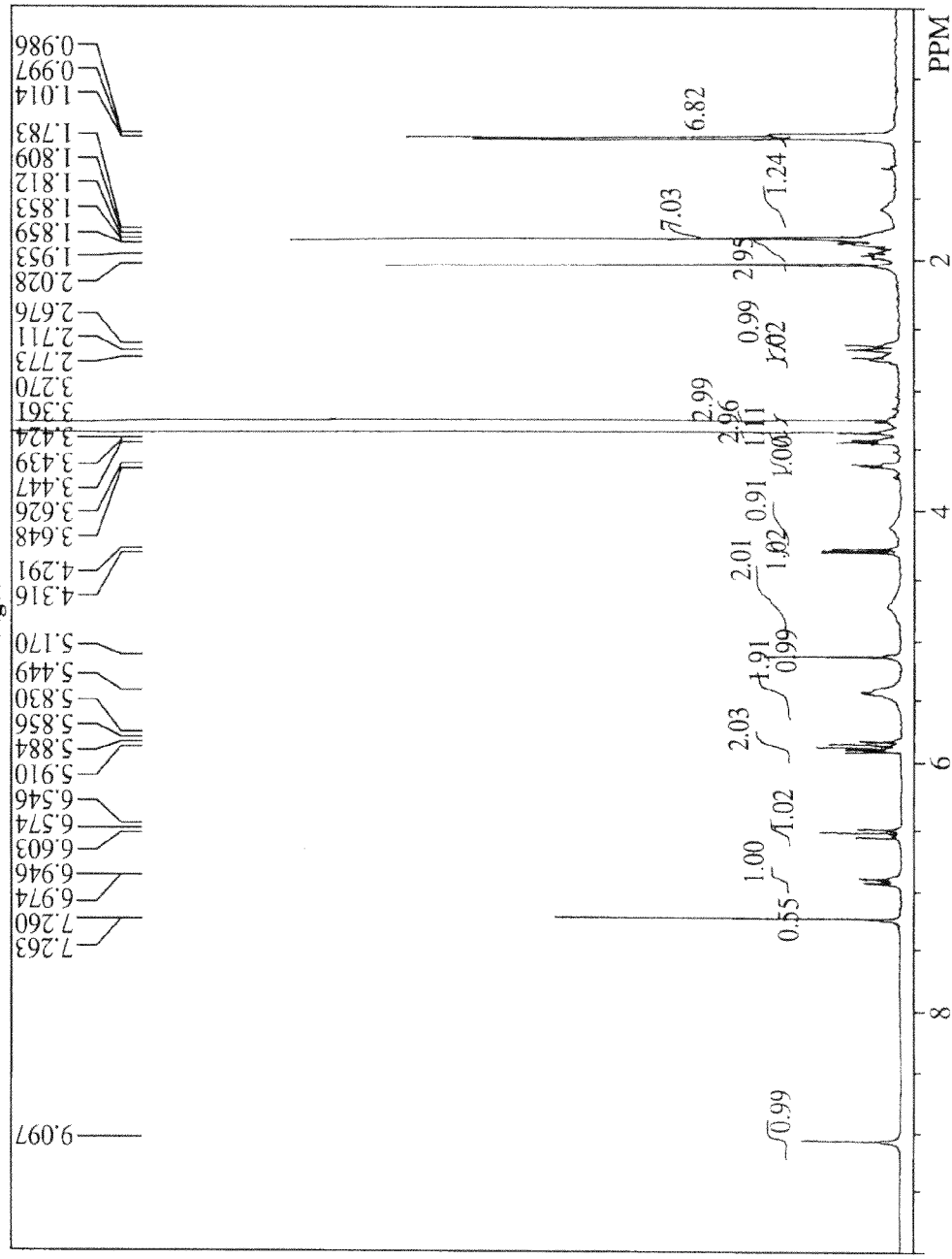
FIG. 4 depicts an $^1$HNMR spectra for Form I of 17-AG.

In some embodiments, Form I is characterized in that it has a DSC pattern similar to that depicted in FIG. 3. A representative $^1$HNMR spectra for Form I is depicted in FIG. 4.

Figure 5:
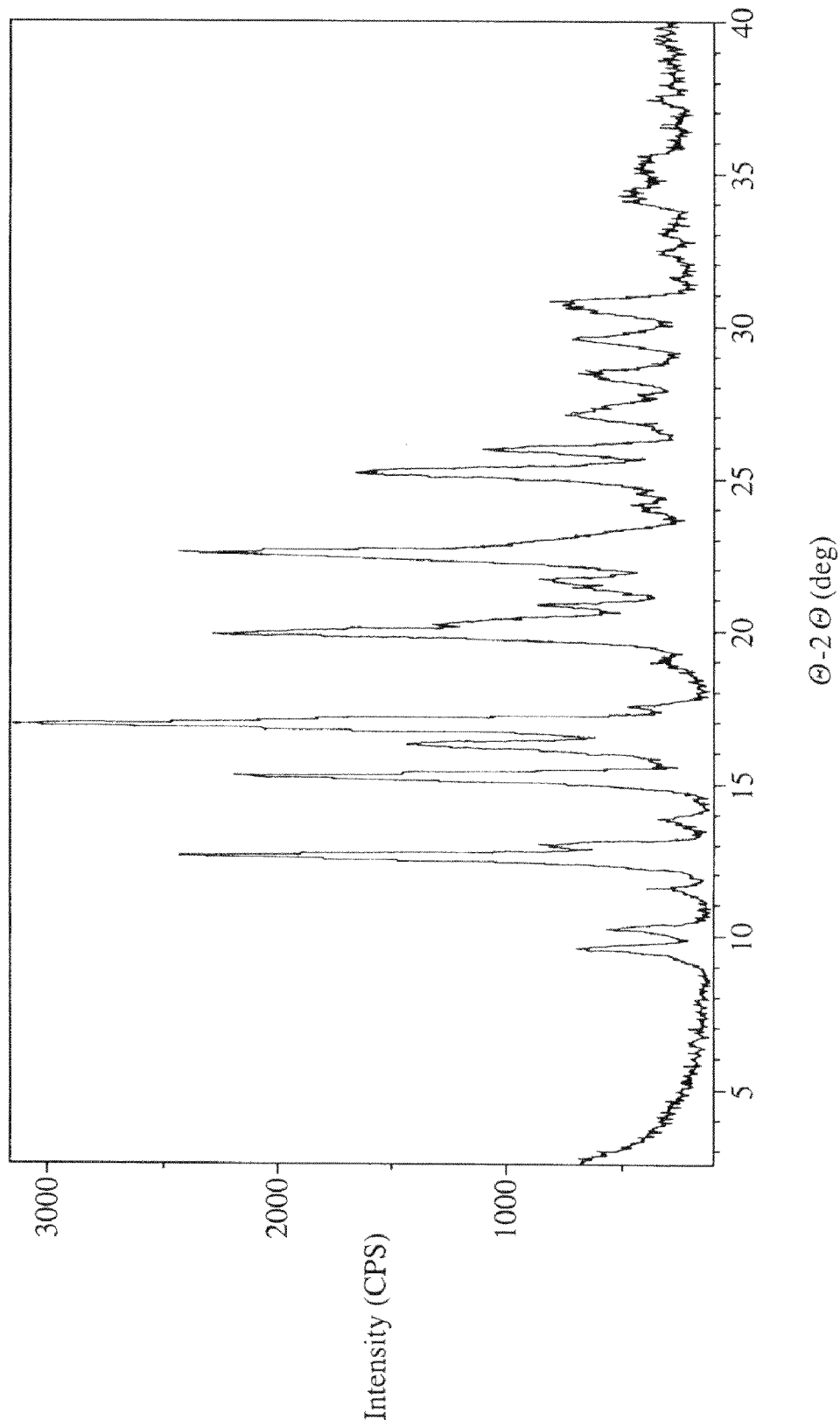
FIG. 5 depicts an XRPD pattern for Form II of 17-AG.

In certain embodiments, provided is Form II of 17-AG substantially free of other geldanamycin analogs. In some embodiments, Form II of 17-AG is substantially free of other solid forms of 17-AG. In some embodiments, Form II is characterized by representative peaks in its XRPD pattern selected from those at about 9.5, 10.1, 12.5, 15.1, 16.1, 16.8, 19.8, 20.7, 21.5, 22.4, 25.1, 25.8, 29.5 and 30.5 degrees 2-theta, and combinations thereof. In some embodiments, Form II is characterized in that it has at least one peak selected from those at about 12.5, 15.1, 20.7, 22.4 and 25.0 degrees 2-theta. In some embodiments, Form II is characterized by at least one representative peak in its XRPD pattern selected from those at about 12.5, 15.1, 20.7, 22.4 and 25.0 in combination with at least one other peak selected from those at about 9.5, 10.1, 12.5, 15.1, 16.1, 16.8, 19.8, 20.7, 21.5, 22.4, 25.1, 25.8, 29.5 and 30.5 degrees 2-theta. In some embodiments, Form II is characterized by its XRPD peaks substantially as shown in FIG. 5.

Figure 6:
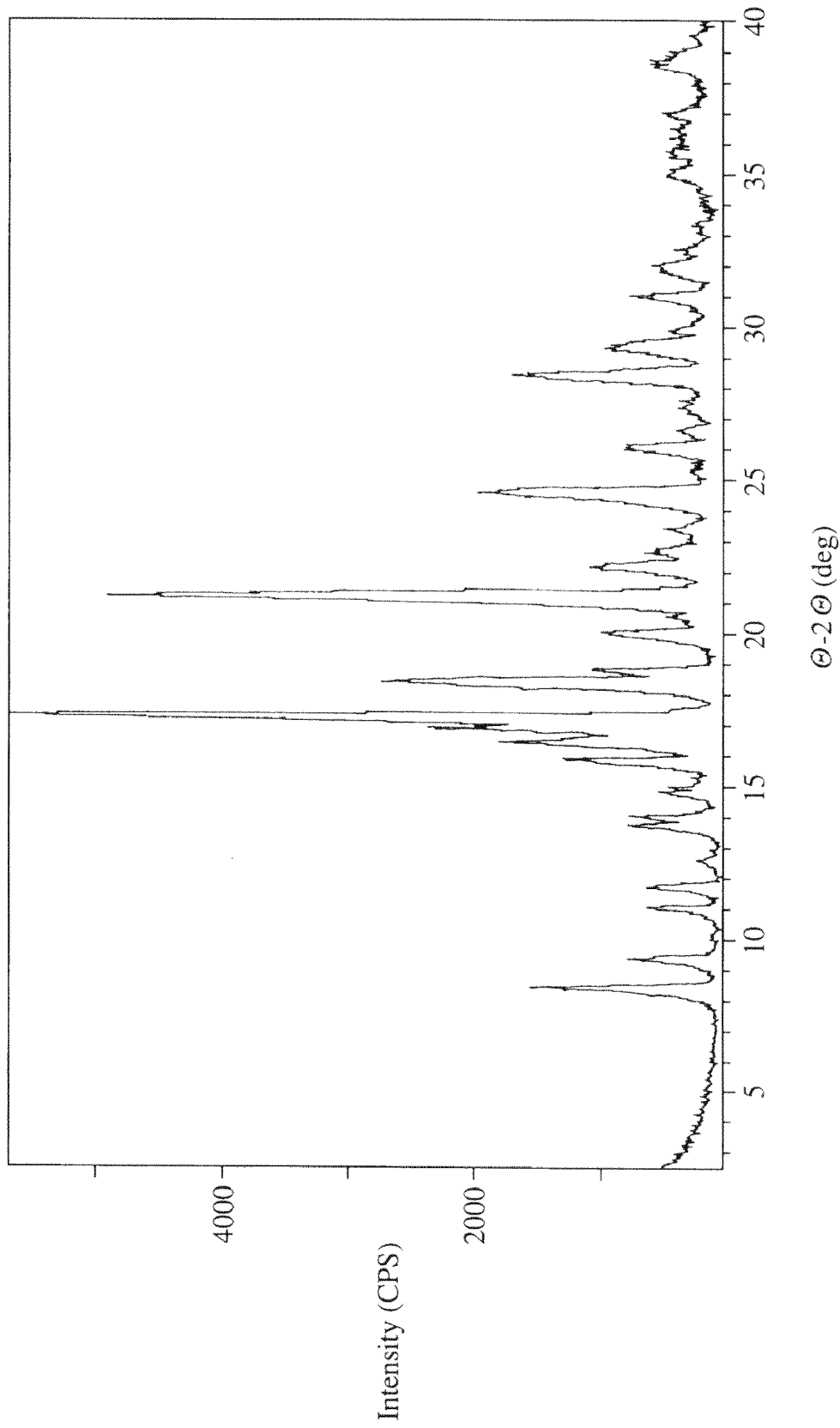
FIG. 6 depicts an XRPD pattern for Form III of 17-AG.

In certain embodiments, provided is Form III of 17-AG substantially free of other geldanamycin analogs. In some embodiments, Form III of 17-AG is substantially free of other solid forms of 17-AG. In some embodiments, Form III is characterized by representative peaks in its XRPD pattern selected from those at about 8.4, 9.3, 10.9, 11.6, 13.6, 13.9, 15.7, 16.3, 17.1, 18.3, 18.6, 19.9, 21.0, 22.0, 24.3, 25.8, 28.2, 29.2, and 30.8 degrees 2-theta, and combinations thereof. In some embodiments, Form III is characterized in that it has at least one peak selected from those at about 18.3, 21.0 and 24.3 degrees 2-theta. In some embodiments, Form III is characterized by at least one representative peak in its XRPD pattern selected from those at about 18.3, 21.0 and 24.3, in combination with at least one other peak selected from those at about 8.4, 9.3, 10.9, 11.6, 13.6, 13.9, 15.7, 16.3, 17.1, 18.3, 18.6, 19.9, 21.0, 22.0, 24.3, 25.8, 28.2, 29.2 degrees 2-theta. In some embodiments, Form III is characterized by its XRPD peaks substantially as shown in FIG. 6.

Also provided is at least one solvate form, referred to herein as EtOAc Solvate, of 17-AG.

Figure 7:
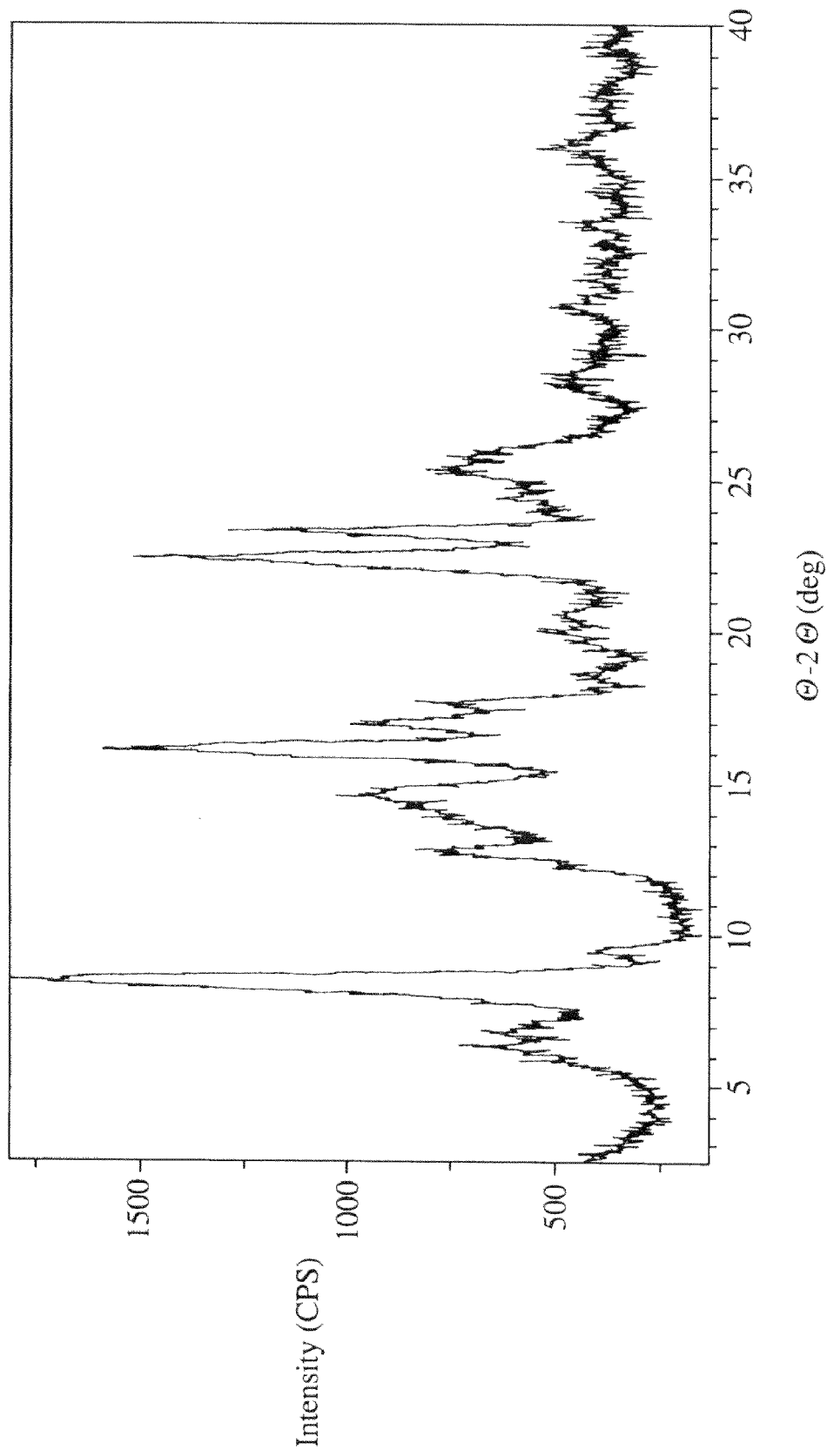
FIG. 7 depicts an XRPD pattern for EtOAc Solvate of 17-AG.

In certain embodiments, provided is an ethyl acetate solvate of 17-AG substantially free of other geldanamycin analogs. In some embodiments, the EtOAc Solvate of 17-AG is substantially free of other solid forms of 17-AG. In some embodiments, the EtOAc Solvate is characterized by representative peaks in its XRPD pattern selected from those at about 6.2, 8.2, 12.6, 14.5, 15.9, 16.8, 17.5, 22.3, 23.3 and 25.3 degrees 2-theta, and combinations thereof. In some embodiments, the EtOAc Solvate is characterized in that it has at least one peak selected from those at about 8.2, 15.9 and 22.3 degrees 2-theta. In some embodiments, the ethyl acetate solvate is characterized by at least one representative peak in its XRPD pattern selected from those at about 8.2, 15.9 and 22.3, in combination with at least one other peak selected from those at about 6.2, 8.2, 12.6, 14.5, 15.9, 16.8, 17.5, 22.3, 23.3 and 25.3 degrees 2-theta. In some embodiments, the EtOAc Solvate is characterized by its XRPD peaks substantially as shown in FIG. 7.

Figure 8:
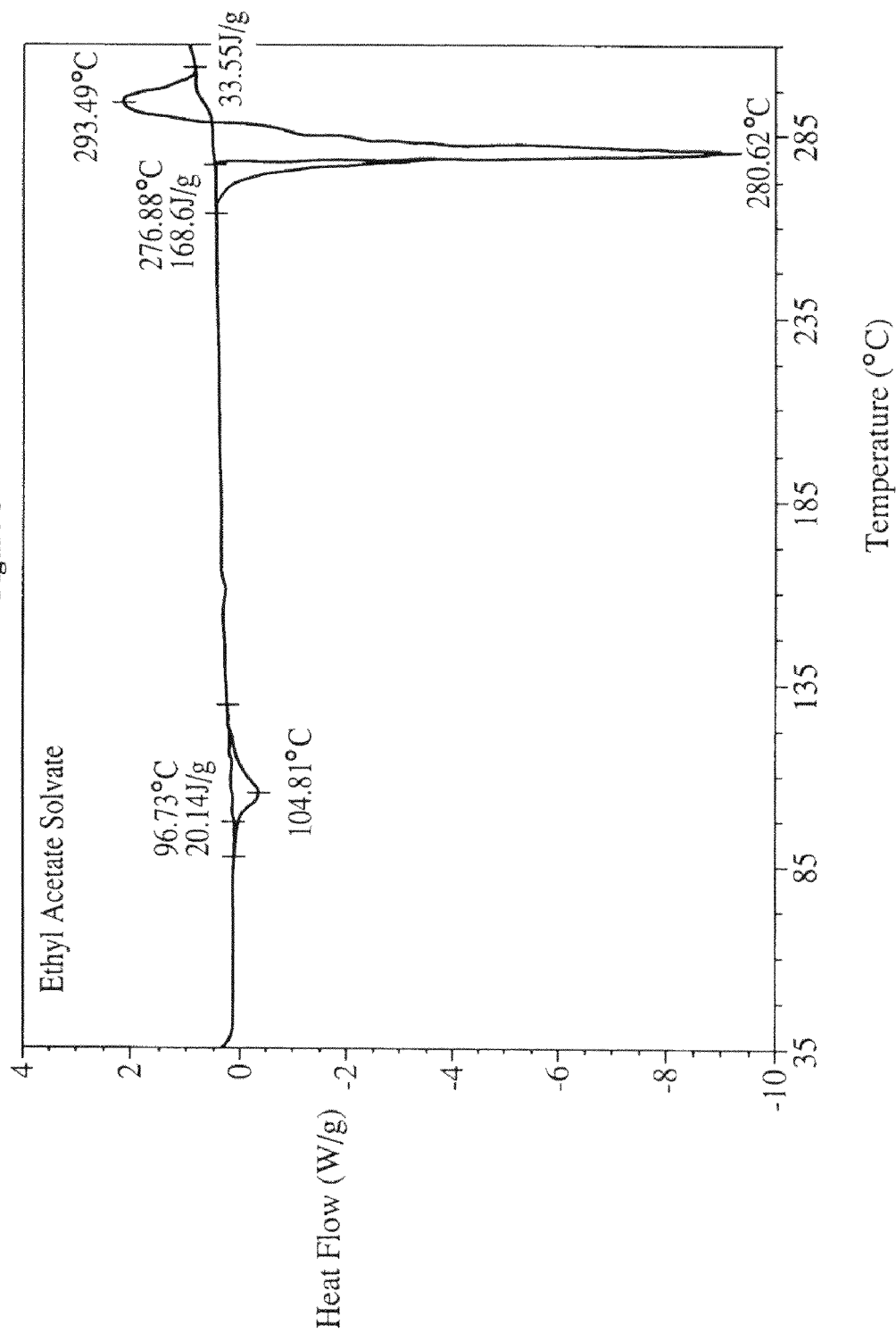
FIG. 8 depicts a DSC pattern for EtOAc Solvate of 17-AG.

In some embodiments, the EtOAc solvate is characterized in that it has a DSC pattern similar to that depicted in FIG. 8. In some embodiment, the DSC shows an endothermic transition at about 96° C., consistent with a desolvation event. In some embodiments, the DSC shows an endothermic transition (melting point onset) at about 276° C.

Figure 9:
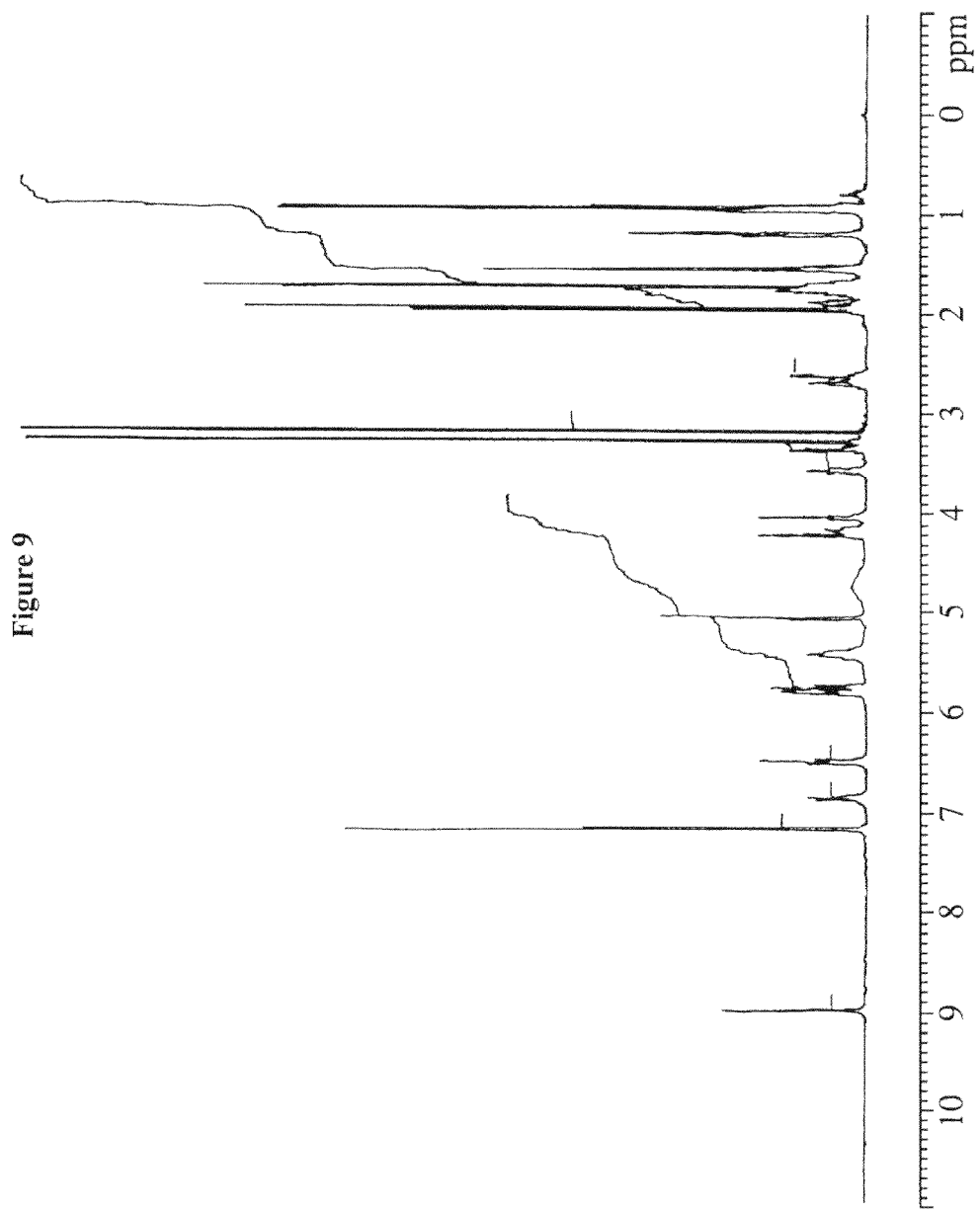
FIG. 9 an $^1$HNMR spectra for EtOAc Solvate of 17-AG demonstrating ratio of 17-AG to ethyl acetate.

In some embodiments, the EtOAc Solvate is characterized by its $^1$HNMR peaks substantially as shown in FIG. 9 below, showing that there is a complex between 17-AG and ethyl acetate in approximate ratio of 2:1.

In another embodiment, also provided herein is 17-AAG can exist as an amorphous solid, referred to herein as amorphous 17-AAG, that is substantially free of other geldanamycin analogs. In some embodiments, amorphous 17-AAG is substantially free of other solid forms of 17-AAG. Amorphous solids are well known to one of ordinary skill in the art and are typically prepared by such methods as lyophilization, melting, and precipitation from supercritical fluid, among others. Methods of preparing amorphous 17-AAG are described in the Examples section, infra.

In certain embodiments, provided is substantially amorphous 17-AAG substantially free of other crystalline forms of 17-AAG.

In some embodiments, provided is a composition comprising amorphous 17-AAG and at least one crystalline form of 17-AAG. Such crystalline forms of 17-AAG include neat crystal forms, solvates and hydrates as described herein or other crystalline forms of 17-AAG that may result from the preparation of, and/or isolation of, amorphous 17-AAG. In certain embodiments, provided is a composition comprising amorphous 17-AAG and at least one crystalline form of 17-AAG as described herein. In some embodiments, provided is a composition comprising amorphous 17-AAG and at least one crystalline form of 17-AAG.

(3) Pharmaceutical Compositions

It is art-recognized that geldanamycin and other benzoquinone ansamycin compounds (including, for example, 17-AG and 17-AAG) are poorly soluble in water, and thus are not suitable for oral administration due to poor bioavailability. Provided herein are pharmaceutical compositions of such compounds that can be administered orally if they, for example, are delivered in an amorphous form (and/or in the presence of a crystallization inhibitor). In one embodiment, provided are oral formulations of benzoquinone ansamycin compounds, such as 17-AG or 17-AAG, which oral formulations comprise amorphous compound in a solid or liquid composition, optionally also including a crystallization inhibitor. In some embodiments, compositions that contain a mixture of an amorphous geldanamycin analog and a crystallization inhibitor, resulted in a surprising finding that the bioavailability of amorphous geldanamycin analogs are dramatically improved and are therefore useful for oral administration.

Without wishing to be bound by any particular theory, we propose that one mechanism that might contribute to the improved bioavailability of inventive oral formulations provided herein might be reduced recrystallization of compound as it is released from the formulation in the gastrointestinal tract. That is, if absorption of a compound is slow as it is released from a delivered formulation, then the possibility exists that a supersaturated solution is generated in the gastrointestinal tract, potentially resulting in crystallization. If crystallization is inhibited, so that more compound remains in solution, improved delivery may be achieved. Thus, the compositions provided herein may achieve rapid and sufficiently long-lasting solubilization of low solubility benzoquinone ansamycin compounds in the aqueous medium in the digestive tract, by inhibiting crystallization of the compound.

In some embodiments, the compositions containing benzoquinone ansamycin compounds (other than 17-DMAG), when dosed at a dose of 15 mg/kg of active compound, are capable of delivering an amount of compound sufficient to achieve an AUC of at least 100 ng·ml/hr, at least 500 ng·ml/hr, at least 1,000 ng·ml/hr, at least 5,000 ng·ml/hr, at least 10,000 ng·ml/hr, at least 15,000 ng·ml/hr, at least 25,000 ng·ml/hr, or at least 50,000 ng·ml/hr of the active compound.

In some of the foregoing embodiments, the compound is present in substantially amorphous form.

In some embodiments, a pharmaceutical composition for oral administration is provided, comprising a crystallization inhibitor and a compound of formula 1:

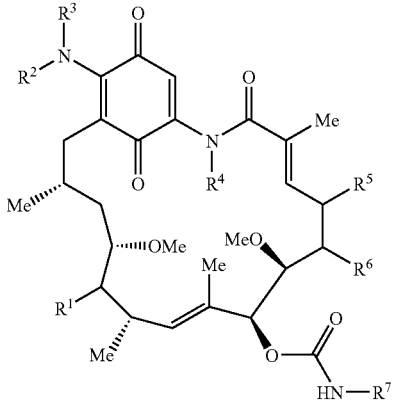

1 or a pharmaceutically acceptable salt thereof, wherein;

$R^1$ is H, —$OR^8$, —$SR^8$—$N(R^8)(R^9)$, —$N(R^8)C(O)R^9$, —$N(R^8)C(O)OR^9$, —$N(R^8)C(O)N(R^8)(R^9)$, —$OC(O)R^8$, —$OC(O)OR^8$, —$OS(O)_2R^8$, —$OS(O)_2OR^8$, —$OP(O)_2OR^8$, CN or a carbonyl moiety;

each of $R^2$ and $R^3$ independently is H, alkyl, alkenyl, alkynyl, cycloalkyl, cycloalkenyl, heterocycloaklyl, aryl, aralkyl, heteroaryl, heteroaralkyl, —C(=O)CH$_3$ or —[(C($R^{10}$)$_2$)$_p$]—$R^{11}$; or $R^2$ and $R^3$ taken together with the nitrogen to which they are bonded represent a 3-8 membered optionally substituted heterocyclic ring which contains 1-3 heteroatoms selected from O, N, S, and P;

p independently for each occurrence is 0, 1, 2, 3, 4, 5, or 6;

$R^4$ is H, alkyl, akenyl, or aralkyl;

$R^5$ and $R^6$ are each H; or $R^5$ and $R^6$ taken together form a bond;

$R^7$ is hydrogen alkyl, alkenyl, alkynyl, cycloalkyl, cycloalkenyl, heterocycloaklyl, aryl, aralkyl, heteroaryl, heteroaralkyl, or —[(C($R^{10}$)$_2$)$_p$]—$R^{11}$;

each of $R^8$ and $R^9$ independently for each occurrence is H, alkyl, alkenyl, alkynyl, cycloalkyl, cycloalkenyl, heterocycloaklyl, aryl, aralkyl, heteroaryl, heteroaralkyl, or —[(C($R^{10}$)$_2$)$_p$]-$R^{11}$; or $R^8$ and $R^9$ taken together represent a 3-8 membered optionally substituted heterocyclic ring which contains 1-3 heteroatoms selected from O, N, S, and P;

$R^{10}$ for each occurrence independently is H, alkyl, alkenyl, alkynyl, cycloalkyl, cycloalkenyl, heterocycloaklyl, aryl, aralkyl, heteroaryl, or heteroaralkyl; and $R^{11}$ for each occurrence independently is H, cycloalkyl, aryl, heteroaryl, heterocyclyl, —$OR^8$, —$SR^8$, —$N(R^8)(R^9)$, —$N(R^8)C(O)R^9$, —$N(R^8)C(O)OR^9$, —$N(R^8)C(O)N(R^8)(R^9)$, —$OC(O)R^8$, —$OC(O)OR^8$, —$OS(O)_2R^8$, —$OS(O)_2OR^8$, —$OP(O)_2OR^8$, —$C(O)R^8$, —$C(O)_2R^8$, —$C(O)N(R^8)(R^9)$, halide, or CN.

In some embodiments $R^1$ is OH, $R^4$ is H, and $R^5$ and $R^6$ taken together form a bond.

In some embodiments, a pharmaceutical composition for oral administration is provided, comprising a crystallization inhibitor and a compound of formula 1:

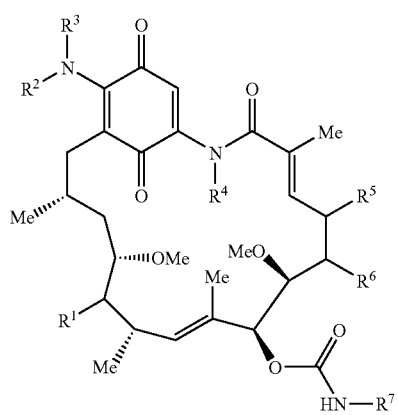

1

In certain embodiments, a pharmaceutical composition for oral administration is provided, comprising a crystallization inhibitor and a compound of formula 1:

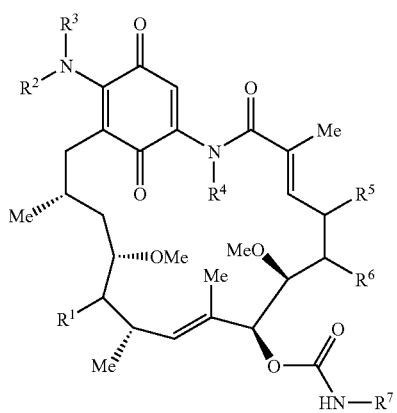

or a pharmaceutically acceptable salt thereof,
wherein;
$R^1$ is —$OR^8$, —C(=O)$CH_3$, or a carbonyl moiety;
each of $R^2$ and $R^3$ independently is H, alkyl, alkenyl or —[(C$(R^{10})_2)_p$]—$R^{11}$; or $R^2$ and $R^3$ taken together with the nitrogen to which they are bonded represent a 3-8 membered optionally substituted heterocyclic ring which contains 1-3 heteroatoms selected from O, N, S, and P;
p independently for each occurrence is 0, 1 or 2;
$R^4$ is H;
$R^5$ and $R^6$ are each H; or $R^5$ and $R^6$ taken together form a bond;
$R^7$ is hydrogen or —[(C$(R^{10})_2)_p$]—$R^{11}$;
each of $R^8$ and $R^9$ independently are H; or $R^8$ and $R^9$ taken together represent a 3-8 membered optionally substituted heterocyclic ring which contains 1-3 heteroatoms selected from O, N, S, and P;
$R^{10}$ for each occurrence independently is H; and
$R^{11}$ for each occurrence independently is H, —N($R^8$)($R^9$) or halide.

Examples of benzoquinone ansamycin compounds include those having the following structures:

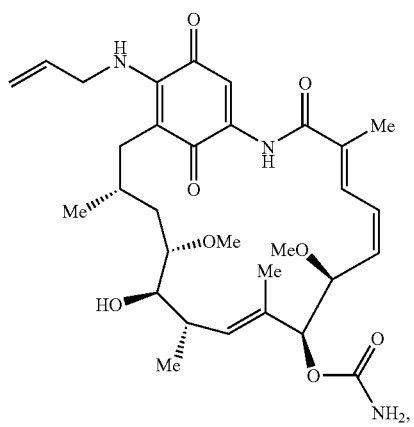

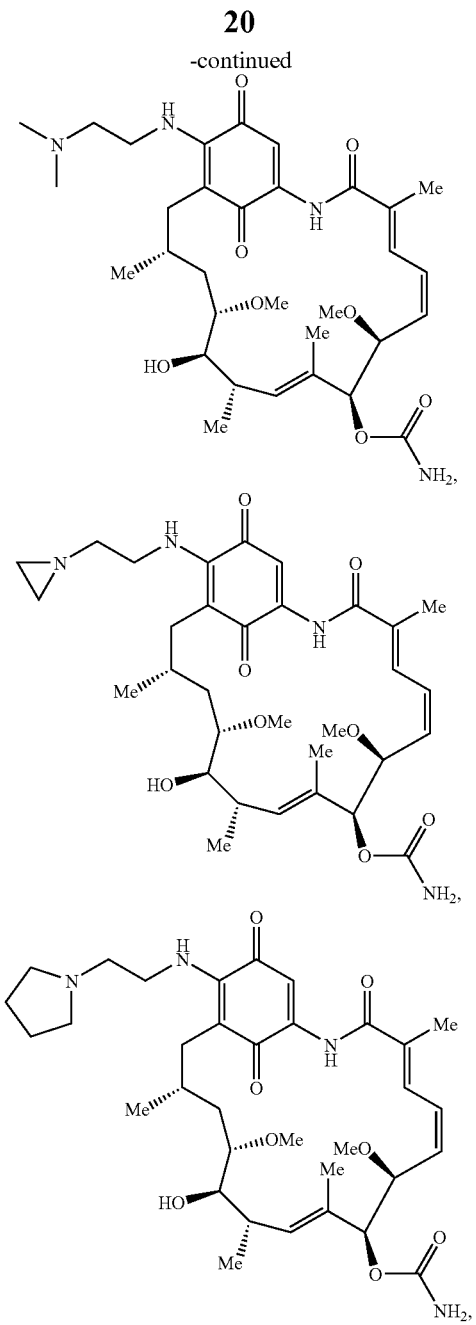

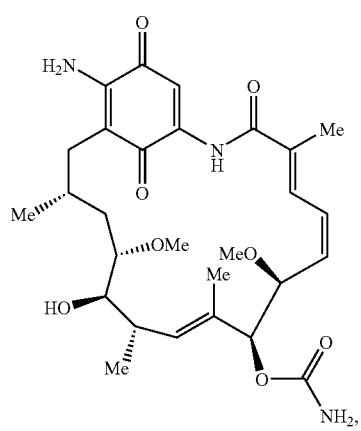

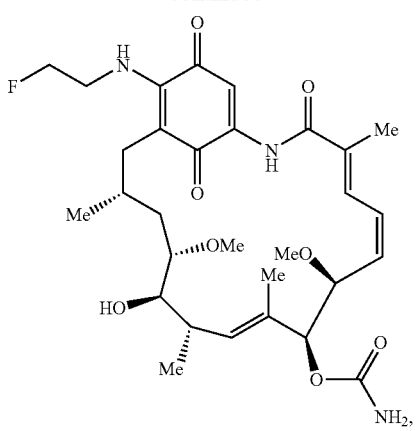
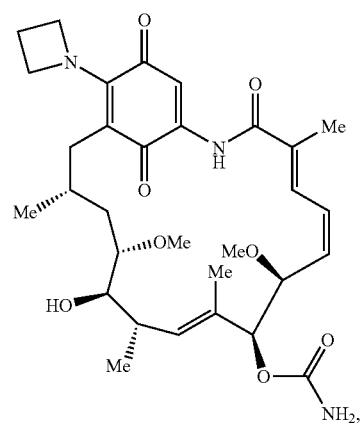
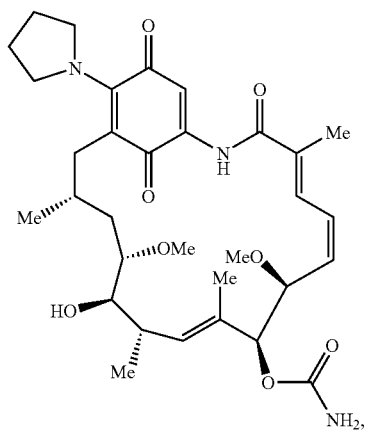
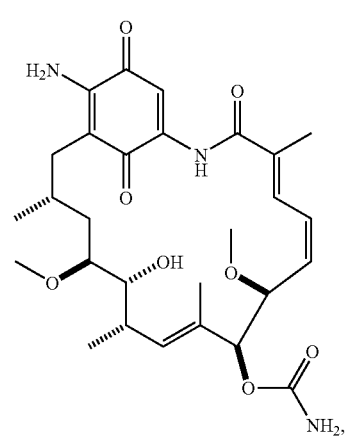
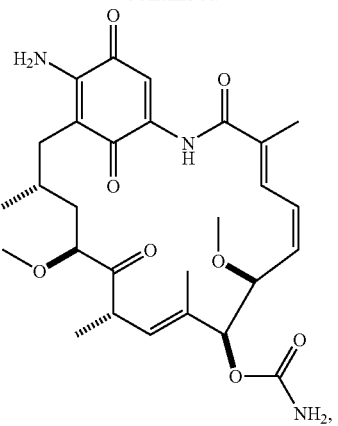
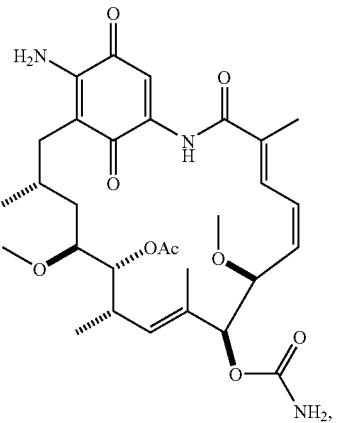
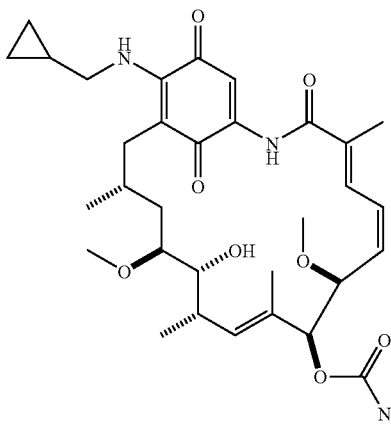
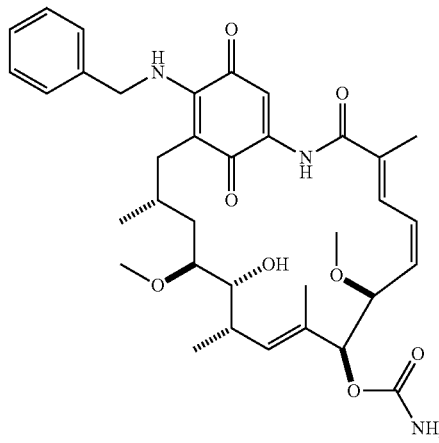

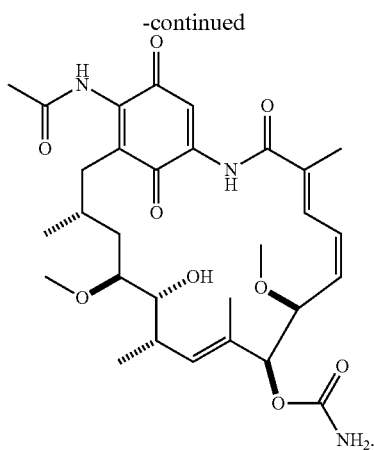

In some embodiments, compositions provided herein containing amorphous 17-AG resulted in a surprising finding of improved bioavailability relative to crystalline 17-AG even when no crystallization inhibitor was used; such compositions are therefore useful for administration, such as oral administration.

In some of the foregoing embodiments, the compound is present in substantially amorphous form.

Similarly, in some embodiments, the composition contains an amount of crystallization inhibitor of at least about 10%, 25%, 50%, 75% (w/w), based on the total weight of the composition.

In some of the foregoing embodiments, the crystallization inhibitor is PVP. In some of the foregoing embodiments, the 17-AG is substantially amorphous.

In certain embodiments, the pharmaceutical composition may be in the form of a paste, solution, slurry, ointment, emulsion or dispersion. In certain embodiments, the pharmaceutical composition is, or comprises, a molecular dispersion.

In certain embodiments, the crystallization inhibitor may be selected from polyvinylpyrrolidone (PVP) (including homo- and copolymers of polyvinylpyrrolidone and homopolymers or copolymers of N-vinylpyrrolidone); crospovidone; gums; cellulose derivatives (including hydroxypropyl methylcellulose (HPMC), hydroxypropyl methylcellulose phthalate, hydroxypropyl cellulose, ethyl cellulose, hydroxyethylcellulose, sodium carboxymethyl cellulose, calcium carboxymethyl cellulose, sodium carboxymethyl cellulose, and others); dextran; acacia; homo- and copolymers of vinyllactam, and mixtures thereof, cyclodextrins; gelatins; hypromellose phthalate; sugars; polyhydric alcohols; polyethylene glycol (PEG); polyethylene oxides; polyoxyethylene derivatives; polyvinyl alcohol; propylene glycol derivatives and the like, SLS, Tween, Eudragit; and combinations thereof. The crystallization inhibitor may be water soluble or water insoluble.

HPMCs vary in the chain length of their cellulosic backbone and consequently in their viscosity as measured for example at a 2% (W/W) in water. HPMC used in the pharmaceutical compositions provided herein may have a viscosity in water (at a concentration of 2% (w/w)), of about 100 to about 100,000 cP, about 1000 to about 15,000 cP, for example about 4000 cP. In certain embodiments, the molecular weight of HPMC used in the pharmaceutical compositions provided herein may have greater than about 10,000, but not greater than about 1,500,000, not greater than about 1,000,000, not greater than about 500,000, or not greater than about 150,000.

HPMCs also vary in the relative degree of substitution of available hydroxyl groups on the cellulosic backbone by methoxy and hydroxypropoxy groups. With increasing hydroxypropoxy substitution, the resulting HPMC becomes more hydrophilic in nature. In certain embodiments, the HPMC has about 15% to about 35%, about 19% to about 32%, or about 22% to about 30%, methoxy substitution, and having about 3% to about 15%, about 4% to about 12%, or about 7% to about 12%, hydroxypropoxy substitution.

HPMCs which can be used in the pharmaceutical compositions are illustratively available under the brand names Methocel™ of Dow Chemical Co. and Metolose™ of Shin-Etsu Chemical Co. Examples of suitable HPMCs having medium viscosity include Methocel™ E4M, and Methocel™ K4M, both of which have a viscosity of about 400 cP at 2% (w/w) water. Examples of HPMCs having higher viscosity include Methocel™ E10M, Methocel™ K15M, and Methocel™ K100M, which have viscosities of about 10,000 cP, 15,000 cP, and 100,000 cP respectively viscosities at 2% (w/w) in water. An example of an HPMC is HPMC-acetate succinate, i.e., HPMC-AS.

In certain embodiments the PVPs used in pharmaceutical compositions provided herein have a molecular weight of about 2,500 to about 3,000,000 Daltons, about 8,000 to about 1,000,000 Daltons, about 10,000 to about 400,000 Daltons, about 10,000 to about 300,000 Daltons, about 10,000 to about 200,000 Daltons, about 10,000 to about 100,000 Daltons, about 10,000 to about 80,000 Daltons, about 10,000 to about 70,000 Daltons, about 10,000 to about 60,000 Daltons, about 10,000 to about 50,000 Daltons, or about 20,000 to about 50,000 Daltons. In certain instances the PVPs used in pharmaceutical compositions provided herein have a dynamic viscosity, 10% in water at 20° C., of about 1.3 to about 700, about 1.5 to about 300, or about 3.5 to about 8.5 mPas.

When PEGs are used they can have an average molecular about 5,000-20,000 Dalton, about 5,000-15,000 Dalton, or about 5,000-10,000 Dalton.

Also provided herein is a pharmaceutical composition for oral delivery, comprising 17-AG and at least one pharmaceutically acceptable excipient, wherein said pharmaceutical composition is substantially free of crystalline 17-AG. In certain instances, the 17-AG in such a pharmaceutical composition includes less than about 15% (w/w), less than about 10% (w/w), less than about 5% (w/w), less than about 3% (w/w), or less than about 1% (w/w) crystalline 17-AG. Such a pharmaceutical composition may be formulated as a solid dosage form (e.g., a tablet or capsule), a paste, emulsion, slurry, or ointment.

Also provided herein is a pharmaceutical composition for oral delivery, comprising 17-AAG and at least one pharmaceutically acceptable excipient, wherein said pharmaceutical composition is substantially free of crystalline 17-AAG. In certain instances, the 17-AAG in such a pharmaceutical composition includes less than about 15% (w/w), less than about 10% (w/w), less than about 5% (w/w), less than about 3% (w/w), or less than about 1% (w/w) crystalline 17-AAG. Such a pharmaceutical composition may be formulated as a solid dosage form (e.g., a tablet or capsule), a paste, emulsion, slurry, or ointment.

As described above, benzoquinone ansamycins and pharmaceutical compositions of the present invention may additionally comprise pharmaceutically acceptable carriers and excipients according to conventional pharmaceutical compounding techniques to form a pharmaceutical composition or dosage form. Suitable pharmaceutically acceptable carriers and excipients include, but are not limited to, those described in Remington's, The Science and Practice of Pharmacy, (Gennaro, A. R., ed., 19th edition, 1995, Mack Pub. Co.), which is herein incorporated by reference. The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g., a human). For oral liquid pharmaceutical compositions, pharmaceutical carriers and excipients can include, but are not limited to water, glycols, oils, alcohols, flavoring agents, preservatives, coloring agents, and the like. Oral solid pharmaceutical compositions may include, but are not limited to starches, sugars, microcrystalline cellulose, diluents, granulating agents, lubricants, binders and disintegrating agents. The pharmaceutical composition and dosage form may also include a benzoquinone ansaymycin compound or solid form thereof as discussed above.

The solid forms described herein can be useful for making pharmaceutical compositions suitable for oral administration. Such pharmaceutical compositions may contain any of the benzoquinone ansamycin compounds described herein, for example, in an amorphous form and no crystallization inhibitor, or an amorphous form in combination with a crystallization inhibitor. Examples of such benzoquinone ansamycins are described in Schnur et al., J. Med. Chem. 1995, 38: 3806-12.

(4) Pharmaceutical Uses and Methods of Treatment

Also provided herein are methods of treating cancer, inhibiting Hsp90, and/or treating a hyperproliferative disorder comprising orally administering to a patient in need thereof a therapeutically effective amount of any of the aforementioned compounds or pharmaceutical compositions. For example, 17-AAG is currently being studied in clinical trials as a treatment for multiple myeloma. 17-AG is produced in the human body by metabolism of 17-AAG (Egorin et al 1998) and is also believed to be an active anti-cancer agent. The cancer, neoplastic disease state or hyperproliferative disorder is selected from the group consisting of gastrointestinal stromal tumor (GIST), colon cancer, colorectal cancer, pancreatic cancer, breast cancer, ovarian cancer, prostate cancer, small cell lung cancer, non-small cell lung cancer, melanoma, multiple myeloma, myelodysplastic syndrome, acute lymphocytic leukemia, acute myelocytic leukemia, chronic myelocytic leukemia, chronic lymphocytic leukemia, polycythemia Vera, Hodgkin lymphoma, non-Hodgkin lymphoma, Waldenstrom's macroglobulinemia, heavy chain disease, soft-tissue sarcomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, endometrial cancer, follicular lymphoma, diffuse large B-cell lymphoma, mantle cell lymphoma, hepatocellular carcinoma, thyroid cancer, gastric cancer, esophageal cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, thyroid cancer, neuroendocrine cancers, and carcinoid tumors.

In certain embodiments, the cancer is selected from the group consisting of gastrointestinal stromal tumor, multiple myeloma, prostate cancer, breast cancer, melanoma, chronic myelocytic leukemia, and non-small cell lung cancer.

In certain embodiments, the methods described herein treat a disease using a benzoquinone compound such as 17-AG. In certain embodiments, 17-AG is substantially amorphous.

(5) Dosing

Actual dosage levels of the benzoquinone ansamycins, e.g., geldanamycin analogs, in the pharmaceutical compositions of the present invention may be varied so as to obtain an amount of the gelanamycin analog which is effective to achieve the desired therapeutic response for a particular patient, composition, and mode of administration, without being toxic to the patient.

The selected dosage level will depend upon a variety of factors including the activity of the particular geldanamycin analog employed, or salt thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds provided herein, employed in the pharmaceutical composition, at levels lower than that required in order to achieve the desired therapeutic effect and gradually increase the dosage until the desired effect is achieved.

In general, a suitable dose of a geldanamycin analog will be that amount of the compound which is the lowest safe and effective dose to produce a therapeutic effect. Such an effective dose will generally depend upon the factors described above. When the geldanamycin analogs are administered in combination with another chemotherapeutic or with radiation, the doses of each agent will in most instances be lower than the corresponding dose for single-agent therapy.

Provided compositions may be formulated into a unit dosage form. Such formulations are well known to one of ordinary skill in the art and include capsules, tablets, and the like. In certain embodiments, the present invention provides a formulation comprising a capsule filled with inventive geldanamycin analogs. In other embodiments, the present invention provides a capsule for oral administration comprising inventive geldanamycin analogs. In some embodiments, a unit dosage form (e.g., a capsule or tablet) contains 5-1,000 mg, e.g., 25, 50, 125, 250 or 500 mg, of a geldanamycin analog. In some embodiments, a unit dosage form contains more than 5 mg/kg of a geldanamycin analog.

In some embodiments, the oral dose is between 1 mg/kg and 100 mg/kg, inclusive, or between 5 mg/kg and 50 mg/kg, inclusive, or between 5 mg/kg and 25 mg/kg, inclusive, or between 10 mg/kg and 20 mg/kg, inclusive, of a geldanamycin analog characterized in that the area under the curve of at least 100 ng·hr/ml is achieved. In some embodiments, the dose is 15 mg/kg. In some embodiments, the area under the curve achieved is at least 500, 1000, 5000, 10,000, or 15,000 ng·hr/ml.

A total daily dosage of a geldanamycin analog (e.g., 17-AG or 17-AAG) will typically be in the range 500-1,500 mg per day. In certain embodiments, an effective amount of a geldanamycin analog for administration to a 70 kg adult human may comprise about 100 mg to about 1,500 mg of compound (e.g., 17-AG or 17-AAG) per day. It will be appreciated that dose ranges set out above provide guidance for the administration of active compound to an adult. The amount to be administered to, for example, an infant or a baby can be determined by a medical practitioner or person skilled in the art and can be lower or the same as that administered to an adult.

The geldanamycin analog can be administered daily, every other day, three times a week, twice a week, weekly, or bi-weekly. The dosing schedule can include a "drug holiday," i.e., the drug can be administered for two weeks on, one week off, or continuously, without a drug holiday.

(6) Combination Therapy

In some embodiments, the pharmaceutical compositions described herein can be used in combination with other therapeutic agents in order to achieve selective activity in the treatment of cancer. In certain embodiments, the geldanamycin analogs described herein are used to reduce the cellular levels of properly folded Hsp90 client proteins, which are then effectively inhibited by the second agent. For example, binding of a benzoquinone ansamycin analog to Hsp90 results in targeting of the client protein to the proteasome, and subsequent degradation. Using an agent that targets and inhibits the proteasome, e.g., Velcade™, then leads to increased cellular apoptosis and cell death.

Some examples of therapeutic agents which can be used in combination with the formulations described herein include alkylating agents; anti-angiogenic agents; anti-metabolites; epidophyllotoxin; procarbazine; mitoxantrone; platinum coordination complexes; anti-mitotics; biological response modifiers and growth inhibitors; hormonal/anti-hormonal therapeutic agents; haematopoietic growth factors; the anthracycline family of drugs; the vinca drugs; the mitomycins; the bleomycins; the cytotoxic nucleosides; the epothilones; discodermolide; the pteridine family of drugs; diynenes; and the podophyllotoxins. Particularly useful members of those classes include, for example, caminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, doxorubicin, vindesine, leurosine, paclitaxel, taxol, taxotere, docetaxel, cis-platin, imatinib mesylate, or gemcitebine.

Other useful agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins. Particularly useful agents include taxotere, Gleevec (imatinib), Tarceva (erlotinib), Sutent (sunitinib), Tykerb (lapatinib), and Xeloda (capecitabine).

The formulations described herein can also be used in conjunction with radiation therapy. The chemotherapeutic agent/radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. The therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, the geldanamycin analogs described herein and the second chemotherapeutic agent do not have to be administered in the same pharmaceutical composition, and may, because of different physical and chemical characteristics, have to be administered by different routes. For example, the geldanamycin compound can be administered orally, while the second chemotherapeutic is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the attending physicians and their judgment of the condition of the patient and the appropriate treatment protocol.

The geldanamycin analog and the second chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the geldanamycin analog.

If the geldanamycin analog, and the chemotherapeutic agent and/or radiation are not administered simultaneously or essentially simultaneously, then the optimum order of administration may be different for different tumors. Thus, in certain situations the geldanamycin analog may be administered first followed by the administration of the chemotherapeutic agent and/or radiation; and in other situations the chemotherapeutic agent and/or radiation may be administered first followed by the administration of a geldanamycin analog. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a geldanamycin analog followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., geldanamycin analog, chemotherapeutic agent or radiation) of the treatment according to the individual patient's needs, as the treatment proceeds.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular geldanamycin analog employed, or salt thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds provided herein, employed in the pharmaceutical composition, at levels lower than that required in order to achieve the desired therapeutic effect and gradually increase the dosage until the desired effect is achieved.

In general, a suitable dose of a geldanamycin analog will be that amount of the compound which is the lowest safe and effective dose to produce a therapeutic effect. The dose can be 1 mg/kg to 25 mg/kg. Such an effective dose will generally depend upon the factors described above. When the geldanamycin analogs are administered in combination with another chemotherapeutic or with radiation, the doses of each agent will in most instances be lower than the corresponding dose for single-agent therapy.

EXAMPLES

The present disclosure now being generally described, it will be more readily understood by reference to the following examples, which are included merely for purposes of illustration of certain aspects and embodiments of the present invention, and are not intended to limit the disclosure herein.

In general, geldanamycin analogs are known to be Hsp90 inhibitors (Schnur et al., J. Med. Chem. (1995), Vol. 38, pages 3806-3812). Examples 1 through 11 describe synthetic chemical preparation for various geldanamycin analogs and solid forms thereof.

Example 1

Preparation of Form I of 17-AG

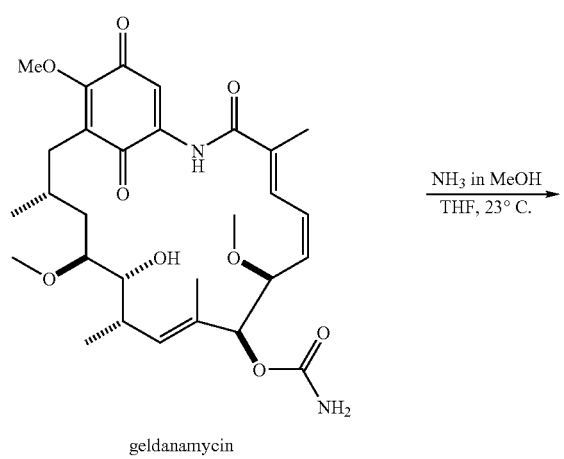

geldanamycin

NH$_3$ in MeOH
THF, 23° C.

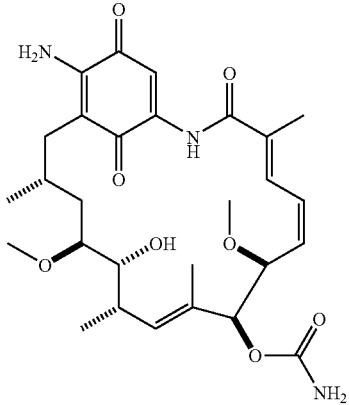

17-aminogeldanamycin
Form I polymorph

A 22 L RB flask was equipped with a bottom drain valve, mechanical stirring, a 1 L addition funnel, internal temperature probe, and an inert gas bypass. Geldanamycin (500 g, 1 eq) and anhydrous THF (5.0 L) was charged to a 22 L RB flask. The stirring is started and Ammonia in MeOH (7 M) is charged (1.0 L, 8.0 eq.) The reaction was stirred at ambient temperature 7 hours. The LCMS indicated complete consumption of starting material at 7 hours. During the course of the reaction, the color changed from yellow to deep purple. Heptane (14 L) was slowly added to the reaction mixture, inducing crystallization of the desired product from solution. The brick red slurry was stirred overnight. The product was isolated by suction filtration and rinsed with 2:1 (v/v) heptane/THF (0.5 L). Oven drying provided crude 17-AG as a powdery, dingy red solid (470 g). The crude material is dissolved in a 4:1 mixture of acetone/ethanol (18-19 L) with heating and clarified. The solution is concentrated and solvent exchanged with additional ethanol (2 L). The ethanol slurry of purple solids is diluted with ethanol (4 L) and water (5 L). The slurry is aged overnight at 35° C. and then heated to 70° C. for 3 hours, during which the crystal form changes and the color turns from dark purple to red. The slurry is cooled to room temperature and the solids are isolated by filtration. The Karl Fisher analysis was 0.86% and all residual solvents were low (EtOH 2266 ppm; acetone 89 ppm; heptane 9 ppm; THF and MeOH not detected). This is the polymorph referred to as Form I.

Example 2

Preparation of Form II of 17-AG

Form I 17-AG (10 g) from the preceding procedure was dissolved in acetone/ethanol at 30° C. and clarified. The flask and the in-line filter were rinsed, and the solution was concentrated via a rotovap to a thick slurry. Then 100 mL of water was added and the rest of the organic solvents removed by vacuum distillation. When the distillate collection ceased, the bath temperature was increased from 40° C. to 60° C. and a small amount of water was removed. Then another portion of water was added (100 mL). With a bath temperature of 80° C. and slight vacuum, water was distilled for ca. 5 min. The slurry remained purple, so the vacuum was disconnected, and the bath increased to 100° C. The slurry was mixed for ca 1 h. The slurry was then allowed to cool to ambient temperature overnight and the purple solids were isolated from water. The Karl Fisher analysis was 0.14% and all residual solvents were low (MeOH: 106 ppm, EtOH: 173 ppm, Acetone 230 ppm, and THF and heptane were not detected). This material is the Form II polymorph.

Example 3

Preparation of Form III of 17-AG

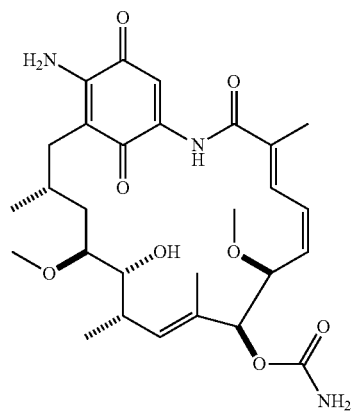

20% 17-amino geldanamycin PVP K-30
amorphous disperison

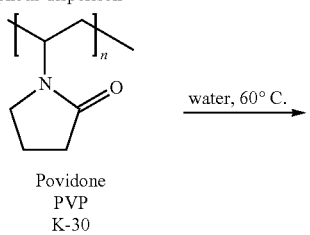

Povidone
PVP
K-30 water, 60° C.

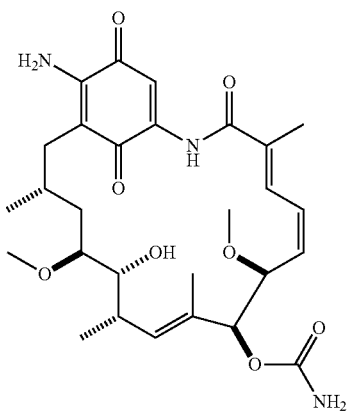

Form III

To 400 mL of distilled water was added 1 g of 20% solid dispersion of 17-aminogeldanamycin in PVP K-30 (as prepared in Example 14). The suspension was heated to 60° C. until complete dissolution of the solid. After heating at 60° C. for 5-10 min, purple crystals precipitated from the solution. The mixture was allowed to cool to 23° C. and the purple crystalline material was isolated by filtration. The collected crystals were dried for 2 days in vacuum oven at 80° C. to give 155 mg 17-AG Form III as purple powder. Yield 75%. MS (ESI(+)) m/z 563.4 (M+H$_2$O)$^+$.

Example 4

Preparation of 17-AG Ethyl Acetate Solvate

To 17-AG (1.2 g) (Form I Polymorph) was added EtOAc (150 mL). The mixture was heated a gentle reflux until 17-AG completely dissolved. The solutions were analyzed using polarized light microscopy to ensure complete dissolution. The volume was reduced to ca 5 mL using a rotatory evaporator and the solution was allowed to cool slowly to room temperature. After 12 h, the mixture was filtered, washed with hexanes and dried to provide the EtOAc solvate based on $^1$HNMR.

Example 5

Preparation of 11-oxo-17-aminogeldanamycin

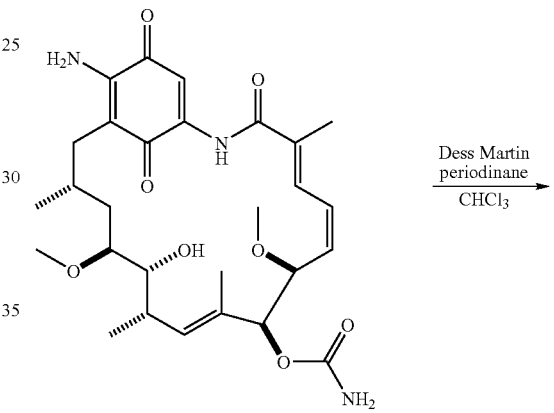

17-aminogeldanamycin

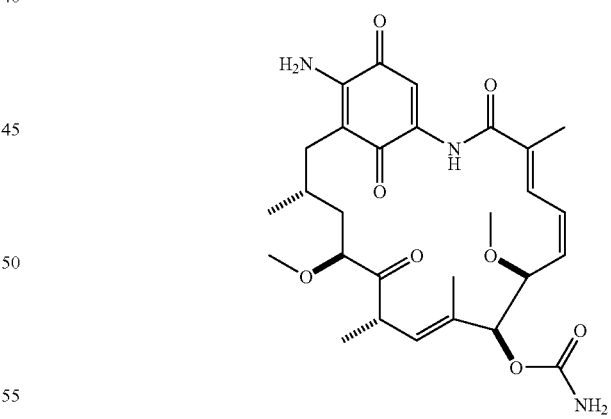

11-oxo-17-aminogeldanamycin

To a 23° C. solution of 17-aminogeldanamycin (5.0 g, 9.16 mmol, 1.0 eq) in CHCl$_3$ (750 mL) was added Dess-Martin periodinane (23.32 g, 55.0 mmol, 6.0 eq.) in a single portion. After stirring for 30 min, the reaction mixture was diluted with CHCl$_3$, washed with aqueous sodium thiosulfate and saturated aqueous sodium bicarbonate. The organic layer was separated, dried over sodium sulfate, filtered and concentrated in vacuo. The crude material was further purified by

Example 6

Preparation of 11-acetyl-17-aminogeldanamycin

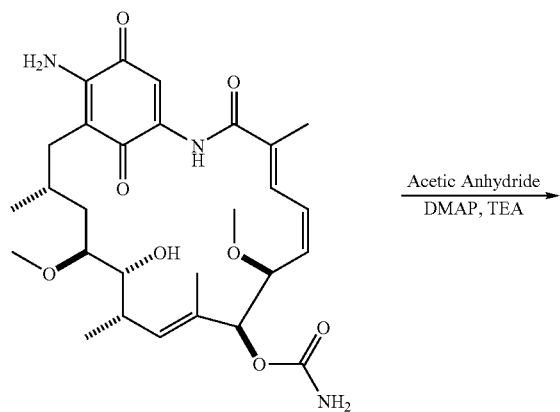

17-aminogeldanamycin

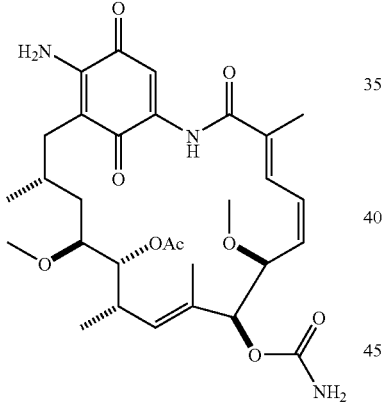

11-acetyl-17-aminogeldanamycin

To a 23° C. solution of 17-aminogeldanamycin (6.0 g, 11.0 mmol, 1.0 eq) in anhydrous DCM (156 mL) under nitrogen atmosphere was added acetic anhydride (2.075 mL, 21.99 mmol, 2.0 eq.), DMAP (1.343 g, 11.0 mmol, 1.0 eq.) and triethylamine (4.60 mL, 33.0 mmol, 3.0 eq.). The reaction mixture was allowed to stir overnight. The reaction mixture was diluted with DCM (200 mL), washed with water (100 mL) and brine (2×100 mL), dried with $Na_2SO_4$, filtered and concentrated in vacuo. The crude material was purified by gradient flash chromatography ($SiO_2$, 30%-60% EtOAc/Hexanes) to provide 1.9 g of the desired product with a trace amount of tris-acetylated product. Yield 30.9%. MS (ESI(+)) m/z 610.4 (M+Na)$^+$.

Example 7

Preparation of 17-cyclopropylmethylaminogeldanamycin

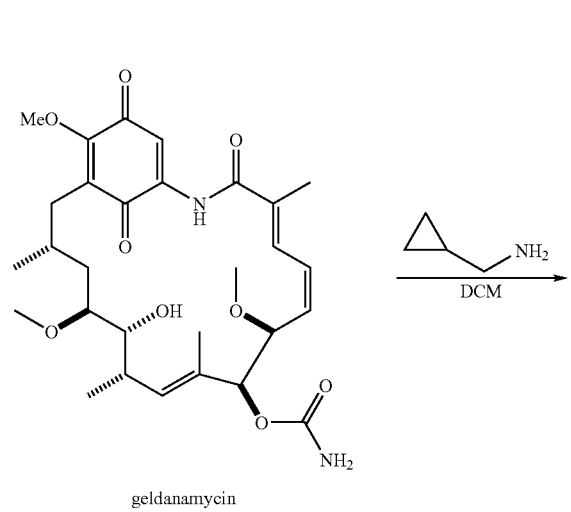

geldanamycin

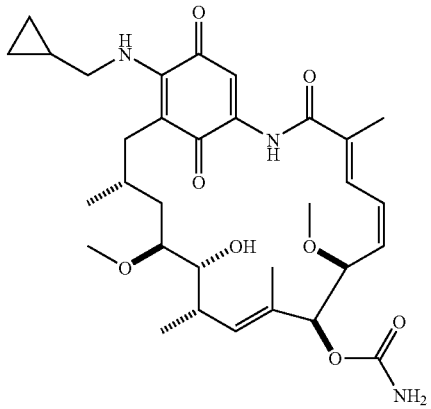

17-cyclopropylmethylaminogeldanamycin

To a 23° C. solution of geldanamycin (3.0 g, 5.35 mmol, 1.0 eq) in DCM (54 mL) under argon was added cyclopropanemethylamine (9.40 mL, 107 mmol, 20 eq). The reaction mixture was allowed to stir for 2 hours. The reaction mixture was then quenched with water (100 mL) and acidified with 1 N HCl to pH 3 and stirred for an additional 30 minutes. The organic layer was separated and the aqueous layer was extracted with DCM. The combined organic extracts were washed with water, dried over $Na_2SO_4$, filtered and concentrated in vacuo. The crude product was purified using gradient flash chromatography ($SiO_2$, 50-60% EtOAc/Hexanes) to afford 2.7 g of the desired product. Yield 84.0%. MS (ESI(+)) m/z 622.4 (M+Na)$^+$.

(From page 33:) recrystallization (DCM/Hexane) to afford 4.12 g of the pure desired product. Yield 83%. MS (ESI(+)) m/z 566.3 (M+Na)$^+$.

Example 8

Preparation of 17-benzylaminogeldanamycin

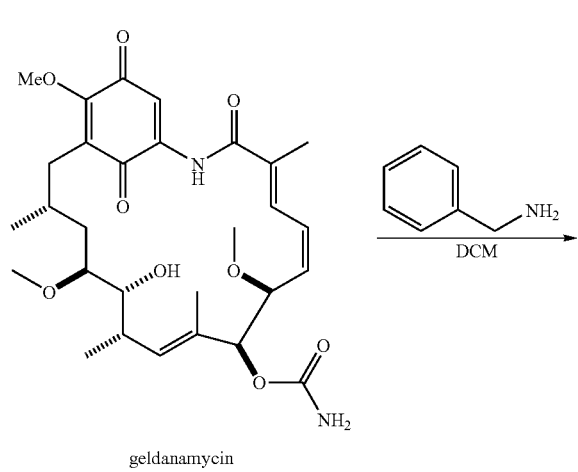

geldanamycin 17-benzylaminogeldanamycin

To a 23° C. solution of geldanamycin (3.25 g, 5.35 mmol, 1.0 eq) in DCM (110 mL) under argon was added benzylamine (9.40 mL, 53.5 mmol, 10 eq) in a single portion. After stirring at 23° C. for 12 h, the reaction mixture was diluted with water (100 mL) and acidified with 1 N HCl to pH 3 and stirred for an additional 30 minutes. The organic layer was separated and the aqueous layer was extracted with DCM. The combined organic extracts were washed with water, dried over $Na_2SO_4$, filtered and concentrated in vacuo. The crude product was purified using gradient flash chromatography ($SiO_2$, 50-60% EtOAc/Hexanes) to afford 3.51 g of the product. Yield 95.0%. MS (ESI(+)) m/z 658.4 (M+Na)$^+$.

Example 9

Preparation of 17-azetidinylgeldanamycin

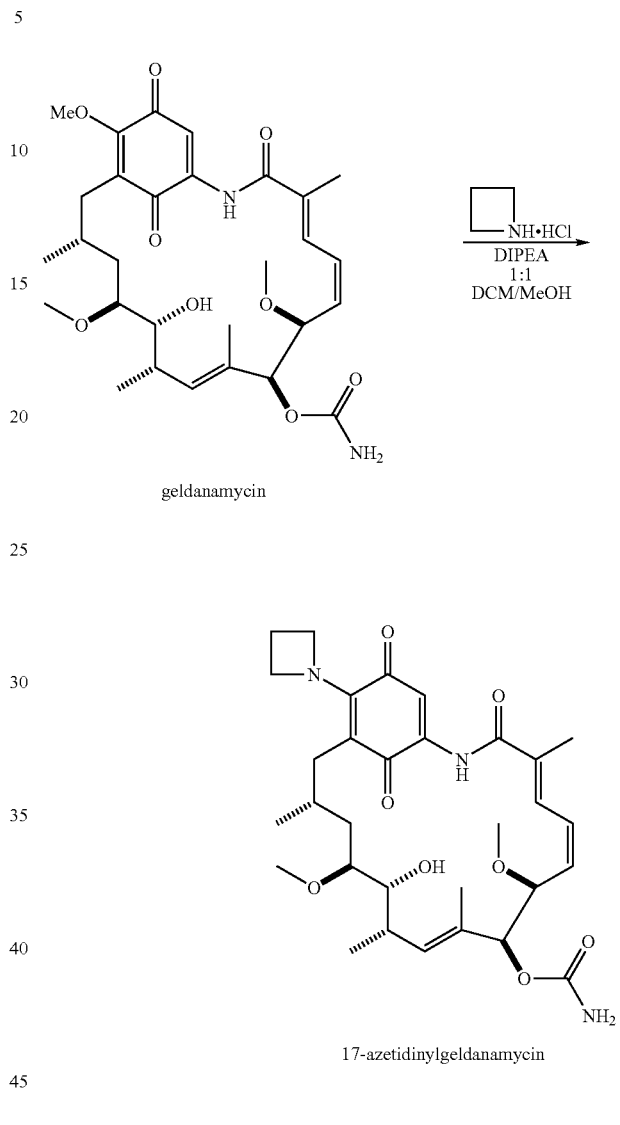

geldanamycin 17-azetidinylgeldanamycin

To a 23° C. solution of azetidine hydrochloride (751 mg, 8.03 mmol, 2.0 eq.) in 1:1 DCM:Methanol (100 mL) was added Hunig's base (2.10 mL, 12.04 mmol, 3.0 eq) followed by geldanamycin (2.25 g, 4.01 mmol, 1.0 eq). After stirring at 23° C. for 2 hours, the reaction mixture was concentrated in vacuo and then re-dissolved in DCM (100 mL). Water (100 mL) was added and the aqueous layer was acidified to pH 3. The mixture was then stirred for 30 minutes. The organic layer was separated and the aqueous layer was extracted with DCM (3×100 mL). The combined organic layers were washed with water (300 mL), dried over $MgSO_4$, filtered and concentrated in vacuo. The crude material was further purified via recrystallization from Chloroform/Hexane to afford 1.92 g of the pure desired product. Yield 82%. MS (ESI(+)) m/z 586.1 (M+H)$^+$.

Example 10

Preparation of 17-(fluoroethyl)aminogeldanamycin

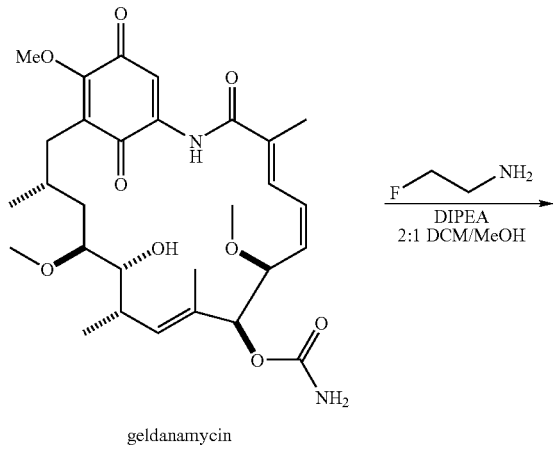

Example 11

Preparation of 17-acetylgeldanamycin

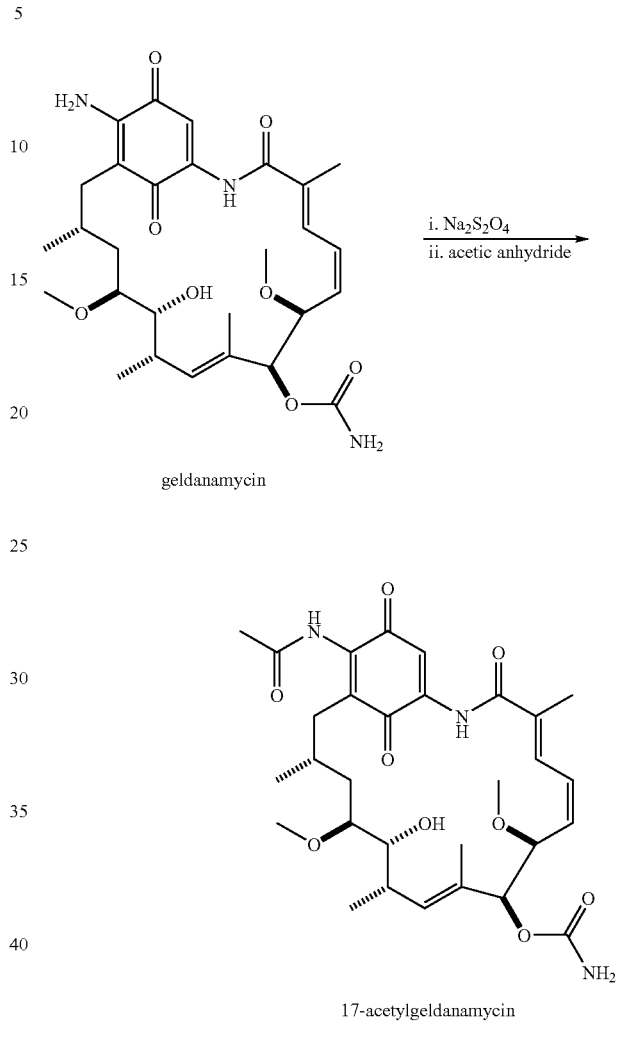

To a 23° C. solution of 2-fluoroethylamine hydrochloride (7.99 g, 80.25 mmol, 7.5 eq.) in DCM (240 mL) and MeOH (120 mL) under nitrogen atmosphere was added Hunig's base (14.02 mL, 80.25 mmol, 7.5 eq.). After the 2-fluoroethylamine hydrochloride dissolved, geldanamycin (6.0 g, 10.70 mmol, 1.0 eq)) was added. After stirring for 24 h at 23° C., the reaction mixture was concentrated in vacuo and then re-dissolved in DCM (900 mL). Water (300 mL) was added and the aqueous layer was acidified to pH 3. The mixture was stirred for 30 minutes. The organic layer was separated and the aqueous layer was extracted with DCM (3×100 mL). The combined organic layers were washed with water (900 mL), dried over $Na_2SO_4$, filtered and concentrated in vacuo. The crude product was purified using gradient flash chromatography ($SiO_2$, 30-60% EtOAc/DCM) to afford 3.0 g of the desired product. Yield 47.4%. MS (ESI(+)) m/z 614.4 (M+Na)$^+$.

To a 23° C. solution of 17-aminogeldanamycin (5.5 g, 10.08 mmol, 1.0 eq) in EtOAc (500 mL) was added $Na_2S_2O_4$ (0.1 M, 500 mL). The biphasic mixture was stirred at 23° C. until the reaction mixture went from a deep purple to a pale yellow color (ca 10 min). The organic layer was separated and the aqueous layer was extracted with EtOAc (3×200 mL). The combined organic extracts were dried over $Na_2SO_4$, filtered and concentrated in vacuo. The residue was then dissolved in $CHCl_3$ (72 mL) under an inert atmosphere ($N_2$) and cooled to 0° C. using an ice bath. Acetic anhydride (2.85 mL, 30.2 mmol, 3.0 eq.) was added dropwise at 0° C. After stirring for 3 h, the reaction mixture was diluted with EtOAc and concentrated in vacuo. The crude product was dissolved in methanol at 23° C. and stirred for 4 days under an open atmosphere to allow for the oxidation of the hydroquinone to the quinone. The crude product was purified by isocratic flash chromatography (80:15:5 DCM:EtOAc:MeOH) to afford 3.5 g of the desired product as a yellow solid. Yield 59.1%. MS (ESI(+)) m/z 610.4 (M+Na)$^+$.

Example 12

Oral Bioavailability Effects Upon Administration of Amorphous Dispersion Formulation (17-AG Plus PVP)

The effect on oral bioavailability of an exemplary compound, 17-AG, in the form of an amorphous dispersion of 17-AG plus PVP (polyvinylpyrrolidone, or also referred to as Povidone) was investigated by dosing beagle dogs and measuring 17-AG levels in blood plasma at various time points following a single oral capsule dose.

A 12% 17-AG/PVP (w/w) dispersion was made utilizing rotary evaporation and characterized for purity, residual solvent level, and amorphous content as described, filled into HPMC capsules and dosed into dogs at a level of 15 mg/kg. Blood was collected pre-dose, at 15 minutes, at 30 minutes, 1 hour, 2 hours, 4 hours, 6 hours, 12 hours, and 24 hours post dose into tubes containing sodium heparin. Collected blood samples were immediately placed on wet ice and refrigerated centrifuge for isolation of plasma within 30 min of collection. Isolated plasma was saved in labeled screw cap freezer vials or eppendorf tubes and stored frozen (−70° C.) until analyzed for plasma 17-AG levels. The design of the study is as follows. A single group of dogs consisting of 2 males & 2 females was utilized for dosing, with a week washout in between each dose.

| Dose 1 | Dose 2 | Dose 3 | Dose 4 |
|---|---|---|---|
| 12% 17-AG PVP K30 @15 mg/kg, uncoated HPMC capsule | N/A | Crystalline 17-AG @15 mg/kg, uncoated HPMC capsule | 12% 17-AG PVP K30 @15 mg/kg, enteric coated HPMC capsule |

After analysis of 17-AG plasma levels following dosing, there was a significant effect on exposure due to the dosing of amorphous 17-AG/PVP dispersion. There was >100-fold increase in both Cmax and AUC levels when dosing amorphous 17-AG/PVP dispersion as compared to dosing crystalline 17-AG. Plasma levels of 17-AG following dosing of crystalline material were below quantifiable limits. Dosing of the 17-AG/PVP dispersion in coated capsules also produced similar increases in exposure but was not as significant as the result from the uncoated capsule. There were no differences seen in the exposure data due to sex for the variables tested. Any variability observed in the exposure is most likely due to animal specific differences or in-life observations (i.e. dosing issues, emesis).

Figures 10A, 10B:
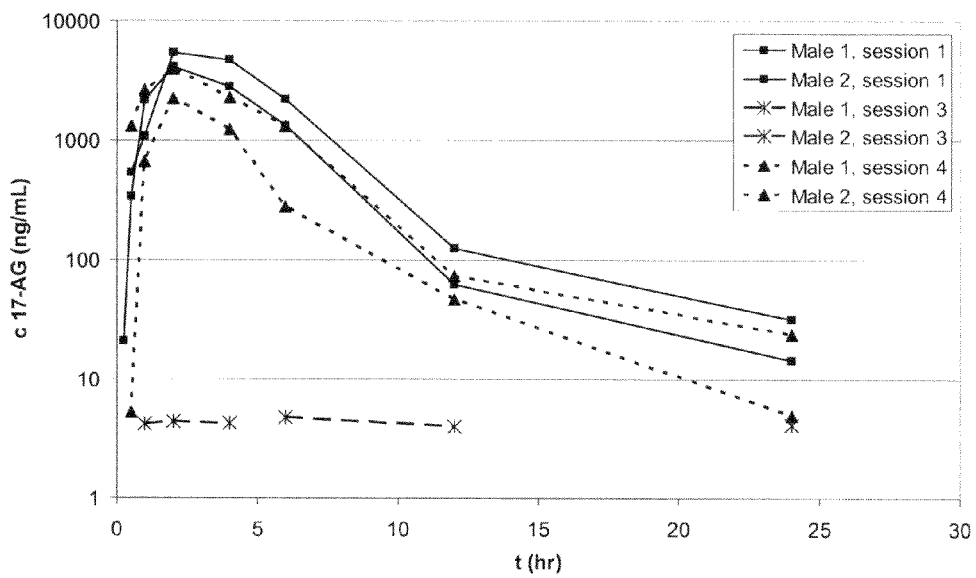
Figures 11A, 11B:
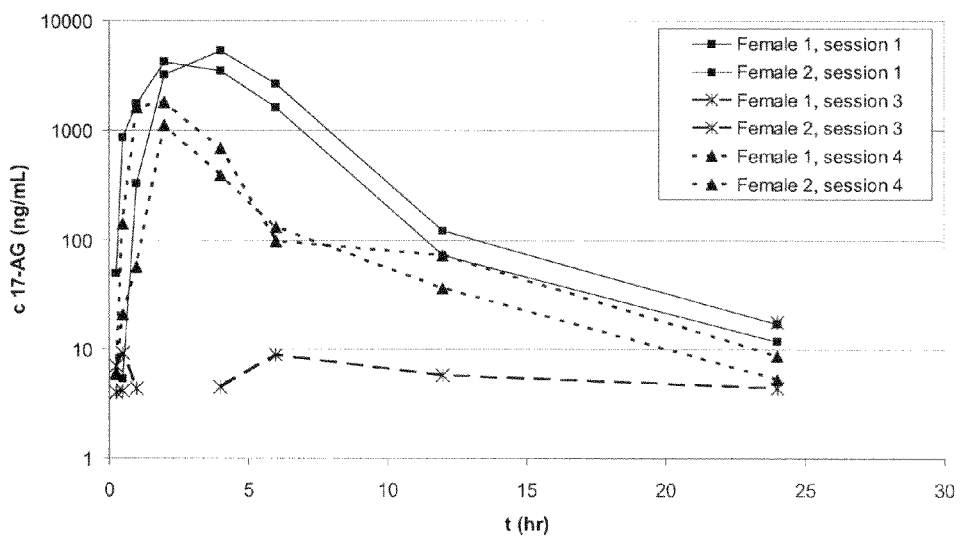

Oral bioavailability results (average values) are found in FIG. 10a (male) and FIG. 11a (female), which demonstrate that crystalline 17-AG has very low oral bioavailability, but amorphous compound has high bioavailability. Summary Tables of PK data are shown in FIG. 10b and FIG. 11b, respectively.

Figure 12:
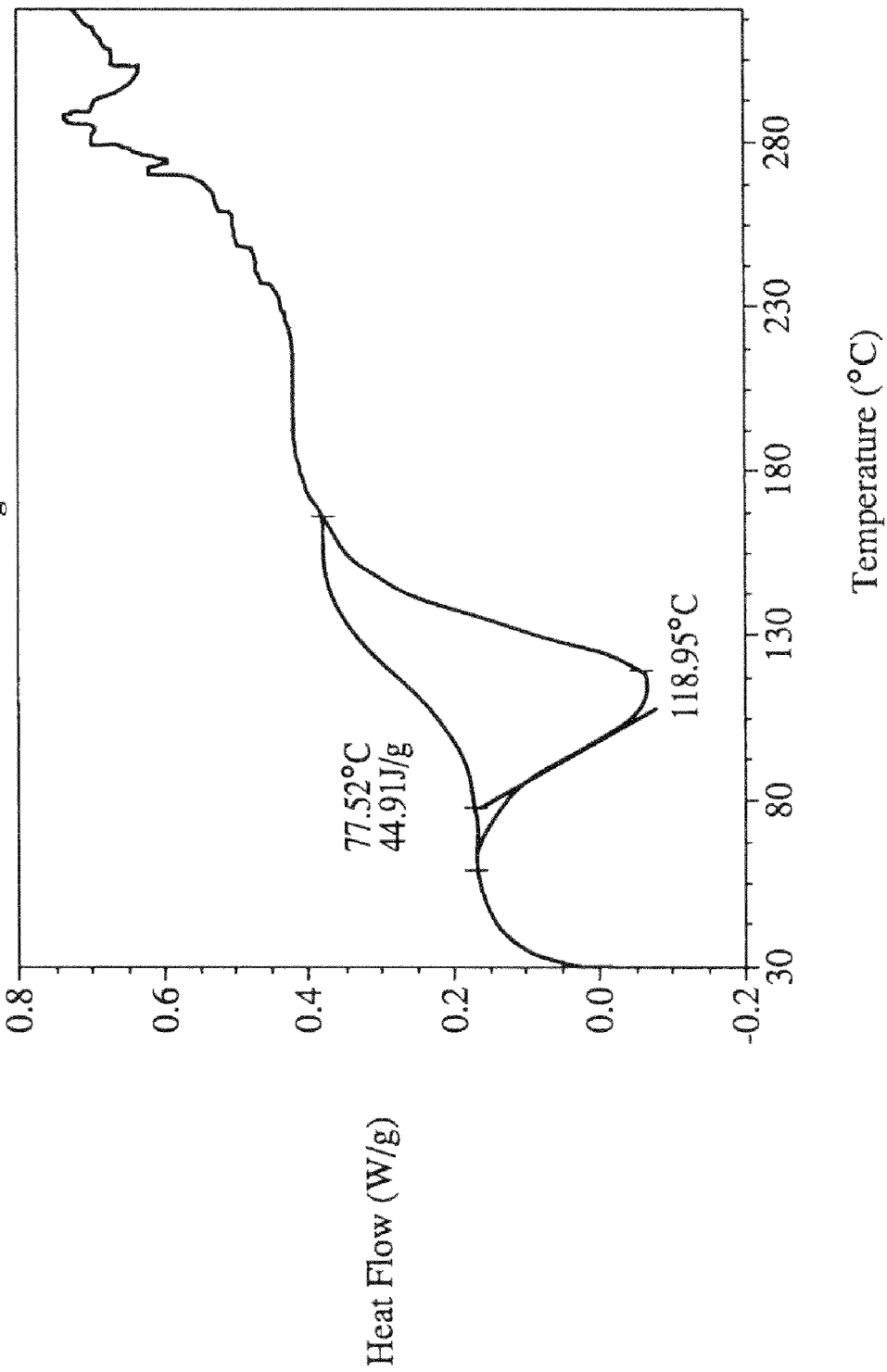
FIG. 12 depicts a DSC scan of 17-AG (12% load) in a PVP K-30 solid dispersion formulation made using lyophilization from t-BuOH/water (3:1).

Following are exemplary methods of preparing solid dispersion formulations using amorphous geldanamycin analogs. Generally, each formulation may be prepared either with a crystallization inhibitor, or without a crystallization inhibitor. When present, the crystallization inhibitor used may vary in both type and in amount. Exemplary methods include, but are not limited to cryo-grinding (Example 13(a)), spray drying (Example 13(b)), lyophilization (Example 13(c)) and rotary evaporation (Example 14 through Example 16). An exemplary DSC pattern that resulted from one technique, i.e., lyophilization utilizing t-BuOH, is found in FIG. 12. Exemplary Exposure data using two different methods of preparing solid dispersions are found in FIG. 14a (rotary evaporation) and FIG. 14b (spray-dried) and a Summary Table in FIG. 14c.

Example 13

Preparation of Amorphous 17-AG

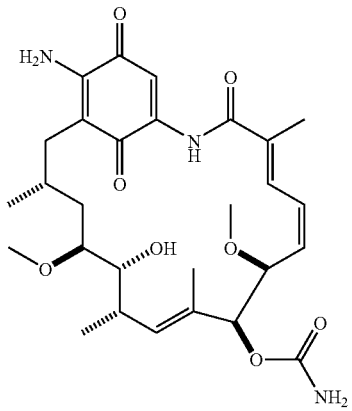

17-aminogeldanamycin
amorphous

To 17-AG (1 g) (Form I Polymorph) was added $CH_3CN$ (50 mL) followed by t-BuOH (100 mL). The mixture was heated at 60° C. until 17-AG completely dissolved was then clarified by filtration through a 0.45 um filter. The solutions were analyzed using polarized light microscopy to ensure complete dissolution. The filtrate was immersed into a bath of liquid nitrogen until frozen and then lyophilized, which resulted in amorphous 17-AG as a light purple powder. The amorphous nature was confirmed via polarized light microscopy.

Example 13(a)

Cryo-Grinding Protocol: Preparation of Amorphous Solid Dispersion Formulation (17-AG and PVP)

17-AG (~1 g) was cooled to ~200° C. in liquid nitrogen and ground to produce amorphous material by physical grinding and pulverizing for 30 minutes. Ground samples were checked for amorphous state by XRPD and P.L.M.

Example 13(b)

Spray Drying Protocol: Preparation of Amorphous Solid Dispersion Formulation [17-AG (20% Load) Plus Polyvinylpyrrolidone (PVP) K-30 Povidone®]

To a 3:1 mixture of acetone (75 g, 94.95 mL) and ethanol 190 proof USP/NF grade (25 g, 31.65 mL) was added Polyvinylpyrrolidone (PVP) K-30 Povidone® (20 g) in a single portion. The mixture was stirred at 23° C. until the dissolution of the polymer was complete (ca 30 min). 17-AG (5 g, 36.7 mmol) was added in portions over the course of 10 mins to provide an opaque purple mixture. After stirring for 2 hours at the room temperature, an aliquot was examined using PLM to ensure complete dissolution; the purple solution was then spray-dried on a Buchi mini spray dryer under the following conditions; Inlet temperature 90° C., Outlet temperature 64° C., $N_2$ flow 600 l/h, Aspiration 70%, to provide a light purple amorphous powder. This material was amorphous based on analysis via polarized light microscopy. MS (ESI(+)) m/z 563.4 $(M+H_2O)^+$.

Example 13(c)

Lyophilization Protocol: Preparation of Amorphous Solid Dispersion Formulation [17-AG in PVP]

A series of amorphous dispersions of varying loads of 17-AG (12%, 15%, 20%, 30%, 40%, 50% w/w) in Polyvinylpyrrolidone (PVP) K-30 and K-90 Povidone® were prepared via lyophilization according to the following protocol. A representative DSC pattern is found in FIG. 12.

A mixture of 17-AG (100 mg, 0.18 mmol) in t-BuOH (500 mL) was heated to 50° C. using a heat gun and stirred vigorously. Aliquots were periodically taken and examined via polarized light microscopy to determine complete dissolution of crystalline 17-AG. After heating at 50° C. for 2 h, the dissolution was complete due to a lack of birefringence observed under polarized light microscopy. The 17-AG solution (62.5 mL, 12.5 mg) was slowly added to the appropriate amount of PVP (K-30 or K-90) dissolved in water (20.8 mL) according to the following schedule. All mixtures maintained a ratio of t-BuOH:water (3:1).

12% load-17-AG (12.5 mg) in tBuOH (62.5 mL)
    PVP (91.5 mg) in water (20.8 mL)
15% load-17-AG (12.5 mg) in tBuOH (62.5 mL)
    PVP (71 mg) in water (20.8 mL)
20% load-17-AG (12.5 mg) in tBuOH (62.5 mL)
    PVP (50 mg) in water (20.8 mL)
30% load-17-AG (12.5 mg) in tBuOH (62.5 mL)
    PVP (29 mg) in water (20.8 mL)
40% load-17-AG (12.5 mg) in tBuOH (62.5 mL)
    PVP (18.7 mg) in water (20.8 mL)
50% load-17-AG (12.5 mg) in tBuOH (62.5 mL)
    PVP (12.5 mg) in water (20.8 mL)

The warm solutions were then transferred to lyophilization cups (110 mL capacity) and allowed to slowly cool to 23° C. After reaching 23° C., the solutions were again analyzed using polarized light microscopy to ensure complete dissolution. No birefringence was detected. All cups were transferred to a pre-cooled (−40° C.) tray lyophilizer, held at −40° C. for 8 hours, and then slowly ramped to 23° C. over the course of 2 days resulting in light purple amorphous solids in quantitative yield. All samples were amorphous based on polarized light microscopy, and >95% pure by HPLC.

Following Examples 14 through 16 further illustrate the rotary evaporation technique to prepare solid dispersion formulations utilizing a variety of PVP grades.

Example 14

Rotary Evaporation Protocol: Preparation of Amorphous Solid Dispersion Formulation [17-AG (12%, 20% and 30% Load) and PVP K-30]

17-AG (12% load, 1.52 g) was added to ethanol (200 proof, 100 mL) and the mixture was stirred at 45° C. for 45 min. In a separate flask PVP K-30 (11.13 g) was added to ethanol (200 proof, 150 mL). The resulting solution was stirred at 45° C. for 15 min.

Figure 39:
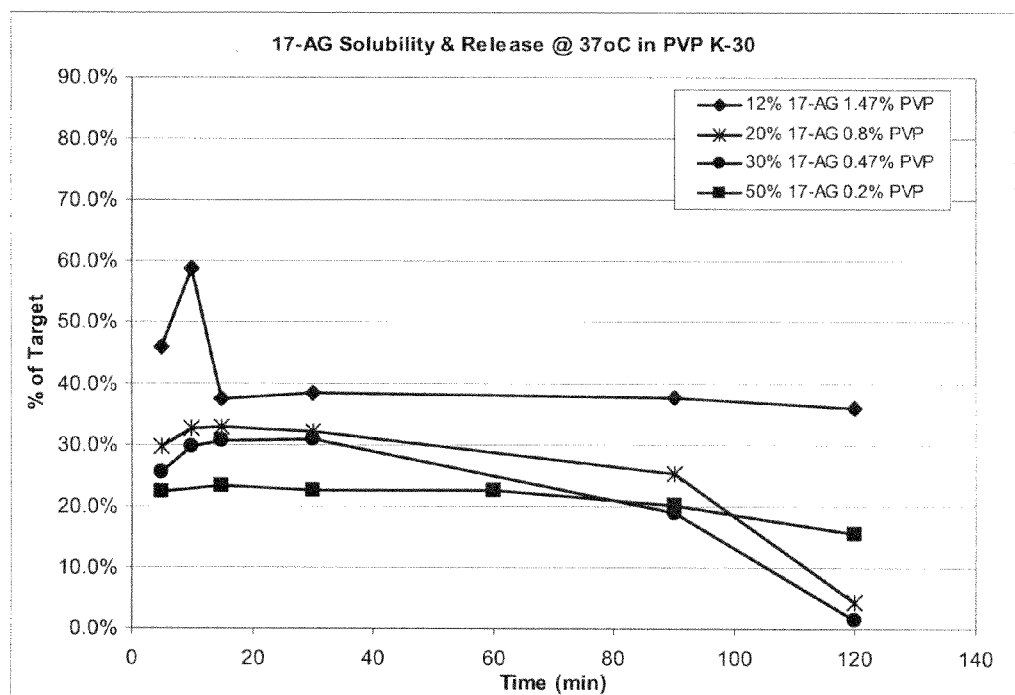
FIG. 39 depicts a graph of a relative in vitro dissolution study (SIF at 37° C.) of amorphous 17-AG plus PVP dispersions using varying load levels of 17-AG (12%, 20%, 30% and 50%). The trend that supersaturated levels of 17-AG was inversely correlated to load (i.e. dispersions with higher load levels of 17-AG and lower levels of crystallization inhibitor, PVP, had lower supersaturated levels of 17-AG) was consistent regardless of the PVP grade.

The 17-AG solution was added to the PVP solution and the resulting solution was stirred at 45° C. for an additional 4 hours (monitored using a microscope, looking for total disappearance of crystals). The homogenous purple solution was then concentrated and pumped under high vacuum for 12 hours. The resulting glass material was analyzed by $^1$H-NMR (to determine residual ethanol content) and by Cross Polar Microscopy (to determine the amount of residual crystalline material). The material was crushed to a powder using a mortar and a pestle and dried under high vacuum at 40° C. for 10 h after which time it was analyzed by $^1$H-NMR for ethanol content. The material was crushed again and further dried under high vacuum for an additional 16 hours to result in fine glassy red-purple material (11.1 g) containing 3% w/w of ethanol. Material was analyzed by $^1$H-NMR, CPM, HPLC and DSC. The amount of 17-AG was adjusted accordingly to achieve corresponding 20% load of 17-AG (w/w) and 30% load of 17-AG (w/w). Representative dissolution data for 12%, 20% and 30% loads are found in FIG. 39.

Example 15

Rotary Evaporation Protocol: Preparation of Amorphous Solid Dispersion Formulation [17-AG (12% Load) in PVP K-15]

Figure 38:
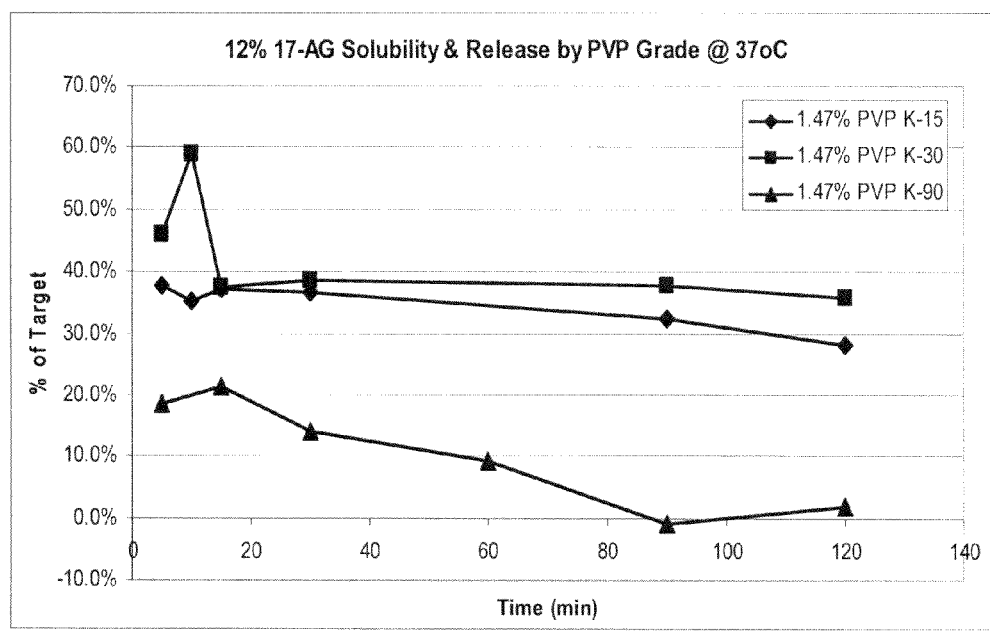
FIG. 38 depicts a graph of a relative in vitro dissolution study (SIF at 37° C.) of amorphous 17-AG (12% load) in solid dispersions using various grades of PVP (K-15, K-30 and K-90) at 37° C., plotted as a function of % of Target (2 mg/ml) versus time (minutes). The trend that PVP K-90 resulted in lower supersaturated levels of 17-AG than PVP K-15 or PVP K-30 grades was consistent regardless of the 17-AG load.

17-AG (10 g) was added to EtOH (1 L, 99.9%) in a 3 L one-necked flask. This mixture was turned at ca 100 rpm on a rototary evaporator at 60° C. and atmospheric pressure. Aliquots were periodically taken and examined via polarized light microscopy to determine complete dissolution of the crystalline 17-AG. After turning at 60° C. for 2 h, the dissolution was complete due to a lack of birefringence observed under polarized light microscopy. Polyvinylpyrrolidone (PVP) K-15 Povidone® (73 g) was added in a single portion and the mixture returned to the rototary evaporator and turned at ca 100 rpm and 60° C. bath temperature. After 1 h, the solutions were again analyzed using polarized light microscopy to ensure complete dissolution. No birefringence was detected. Vacuum was applied and the EtOH was removed over the course of 30 min resulting in purple foam. The flask was transferred to the hi-vac and dried overnight. The brittle foam was scraped from the sides and the crude material was pumped under hi-vac for an additional 36 h. The material was further crushed with a spatula to facilitate removal from the flask to provide 76 g (92% yield) of an amorphous dispersion based on polarized light microscopy and XRPD. Representative dissolution data is found in FIG. 38.

Example 16

Rotary Evaporation Protocol: Preparation of Amorphous Solid Dispersion Formulation [17-AG (12% Load) in PVP K-90]

An amorphous solid dispersion formulation [17-AG (12% load) in PVP K-90 was prepared using a procedure similar to above Example 15 except that PVP K-30 was used to obtain 48 g (48% yield) of an amorphous dispersion based upon polarized light microscopy, using rotary evaporation followed by hi-vac. Representative dissolution data is found in FIG. 38.

Following Example 17 is a stability study that was conducted on the formulations described above (in Examples 14, 15 and 16), and summarized in the table below.

Example 17

Various 17-AG/PVP dispersions were subjected to various storage conditions and the chemical and physical stability of each were assessed at specified time points. The dispersions tested were: 12% 17-AG in PVP K15, 12% 17-AG in PVP K90, 12% 17-AG in PVP K30, 20% 17-AG in PVP K30, and 30% 17-AG in PVP K30. The storage conditions tested were: RT ambient humidity, RT 33% RH, RT 75% RH, 40° C. ambient humidity, and 40° C. 75% RH. Chemical stability of 17-AG was assessed by measurement of purity by RP-HPLC, and physical stability of the amorphous dispersions was assessed by appearance of crystalline material by polarized light microscopy (P.L.M.). Separate aliquots for each timepoint and storage condition were made for every dispersion by placing ~50 mg of material in open glass vials. Vials were placed in appropriate temperature controlled stability chambers which utilized saturated salt solutions to control humidity (magnesium chloride for 33% RH, and sodium chloride for 75% RH). Stability data for T=0 and T=1 month time point for the dispersions and conditions tested is shown in the table below.

| Conditions | 12% K-15 | | 12% K-90 | | 12% K-30 | | 20% K-30 | | 30% K-30 | |
|---|---|---|---|---|---|---|---|---|---|---|
| | HPLC Purity (%) | Appearance by P.L.M. | HPLC Purity (%) | Appearance by P.L.M. | HPLC Purity (%) | Appearance by P.L.M. | HPLC Purity (%) | Appearance by P.L.M. | HPLC Purity (%) | Appearance by P.L.M. |
| T = 0 | 97.10 | amorphous | 97.30 | amorphous | 99.50 | amorphous | 99.60 | amorphous | 99.70 | amorphous |
| RT | Stability time points | | | amorphous | 98.62 | amorphous | 99.15 | amorphous | 99.42 | amorphous |
| RT, 33% RH | stopped at 2 weeks | | | amorphous | 98.71 | amorphous | 99.29 | amorphous | 99.40 | amorphous |
| RT, 75% RH | | | 97.09 | amorphous | 98.09 | amorphous | 98.89 | amorphous | 99.24 | amorphous |
| 40° C. | | | 98.57 | amorphous | 98.13 | amorphous | 98.87 | amorphous | 99.34 | amorphous |
| 40° C., 75% RH | | | 91.49 | some crystalline material visible | 93.04 | some crystalline material visible | 94.96 | some crystalline material visible | 96.86 | some crystalline material visible |

Example 18

Preparation of a Solid Dispersion [17-AAG in PEG6000 (5% w/w)]

To a solution of geldanamycin (20.0 g, 35.7 mmol, 1 eq.) in DCM (750 mL) was added allylamine (53 mL, 714 mmol, 20 eq) at room temperature and under nitrogen atmosphere. The slurry was stirred at room temperature for 6 hours. The resulting purple solution was quenched with water (300 mL) and acidified with 2N HCl (300 mL) to pH 3 and stirred for and additional 30 min. The aqueous phase was extracted with DCM (300 mL) and the combined organic layers washed with water (300 mL), dried over $MgSO_4$, filtered, and concentrated. The purple residue was dissolved into acetone (300 mL) at 60° C. and heptanes (1.5 L) was added and the resulting mixture cooled to 5° C., filtered, and the solid washed with heptane (200 mL) to afford crude 17-AAG (18.15 g) after drying. The purple solid was dissolved in of acetone (306 mL) heated to 55-60° C. and n-heptane (1.2 L) was slowly added to form a slurry. The mixture was maintained at 55° C. for 30 minutes and cooled to room temperature. The crystalline material was collected and dried under vacuum for 48 hours to afford 17-AAG as purple needles. (16.15 g, 28 mmol, 77% yield). >99% pure by HPLC monitored (254 nm) mp 210-212° C.

To 17-AAG (18 mg) was added PEG6000 (382 mg) and the solid mixture was melted using heat. The resulting waxy dispersion was analyzed by HPLC and by Cross Polar Microscopy.

Additional solid amorphous dispersions containing 17-AAG were prepared, the amorphous character was confirmed by polarized light microscopy and are summarized in the following table.

| Composition/TA Load (%) | Polymer | Grade | Method | Solvent (EtOH) | Physical appearance | Dissolution |
|---|---|---|---|---|---|---|
| 95 | PEG | 1000 | melt/fusion | | | |
| 2 | PEG | 1000 | melt/fusion | | | |
| 2 | PEG | 6000 | melt/fusion | | slow dissolution, glassy material | |
| 3 | PVP | K-90 | rotary evaporation | 2 ml | slow dissolution, glassy material | |
| 4 | PVP | K-90 | rotary evaporation | 2 ml | slow dissolution, glassy material | |
| 5 | PEG | 1000 | melt/fusion | | | |
| 5 | PEG | 6000 | melt/fusion | | appears amorphous by PLM | |
| 17 | PVP | K-30 | rotary evaporation | | appears amorphous by PLM | |
| 33 | PVP | K-30 | rotary evaporation | | appears amorphous by PLM | |
| 25 | PVP | K-30 | mechanical mix | | | |
| 30 | PVP | K-30 | rotary evaporation | 35 ml | appears amorphous by PLM | |
| 13 | PVP | K-30 | rotary evaporation | 10 ml | appears amorphous by PLM | |
| 5 | PVP | K-30 | rotary evaporation | 10 ml | appears amorphous by PLM | |
| 10 | PVP | K-30 | rotary evaporation | 10 ml | appears amorphous by PLM | |
| 20 | PVP | K-30 | rotary evaporation | 10 ml | appears amorphous by PLM | |
| 25 | PVP | K-30 | rotary evaporation | 10 ml | appears amorphous by PLM | |
| 12 | PVP | K-30 | rotary evaporation | 100 ml | appears amorphous by PLM | increased solubility by in-vitro dissolution |

Example 19

Preparation of 17-AG Amorphous Solid Dispersion Formulations [17-AG (20% Load) in Various Polymers]

Method for Preparing Dispersions:

17-AG (2 g) was added to EtOH (1 L) in a 3 L one-necked flask. This mixture was turned on the rotary evaporator at 60° C., ambient pressure and aggressive turning. An aliquot was taken and examined for signs of crystallization under the microscope after 1 hour. Polymer (8.2 g) was added and the mixture was concentrated via rotary evaporation and turned at 60° C. for another hour. An aliquot was taken and examined for signs of crystallization using PLM after the hour. Vacuum was then applied and the EtOH was removed over the course of 30 minutes to provide a foam-like material. The material was dried in vacuo over night. The resulting brittle foam was then scraped from the sides and the material was pumped under high-vacuum for an additional 36 hours. The solid dispersion generated was then ground and sieved (No. 50 sieve) to a particle size of 300 microns.

Example 20

General Techniques Utilized to Characterize Amorphous Materials

Visual Polarized Light Microscopy (PLM): A check ("✓") indicates no visual signs of crystalline material and no birefringence under cross polarized light when examining the solid state material or when dissolved in water.

Figure 44:
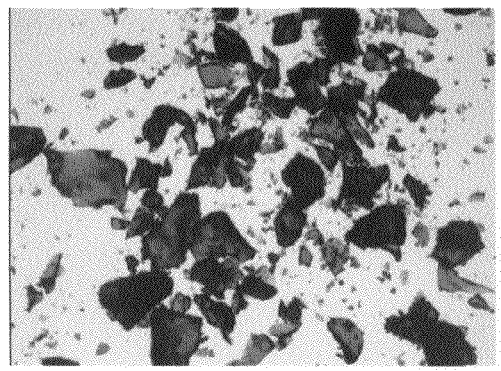
FIG. 44 depicts exemplary images acquired using a polarized light microscope: (A) 4× transmitted light image of solid state 17AG/PVP amorphous dispersion; (B) 10× polarized light image of 17AG/PVP amorphous dispersion in water; (C) 10× polarized light image of 0.01% spike of crystalline Form I into a 17-AG/PVP amorphous dispersion, dissolved in water; (D) 10× polarized light image of 0.1% spike of crystalline Form I into a 17-AG/PVP amorphous dispersion, dissolved in water; and (E) 10× polarized light image of 1.0% spike of crystalline Form I into a 17-AG/PVP amorphous dispersion, dissolved in water.
Figure 44:
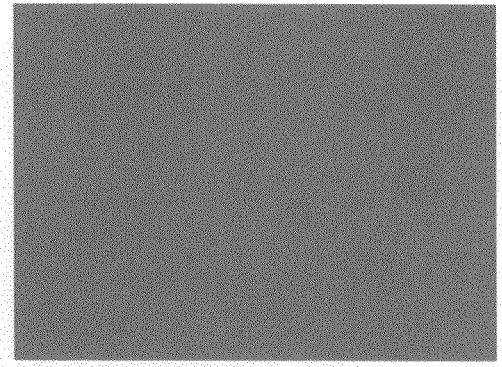
Figure 44:
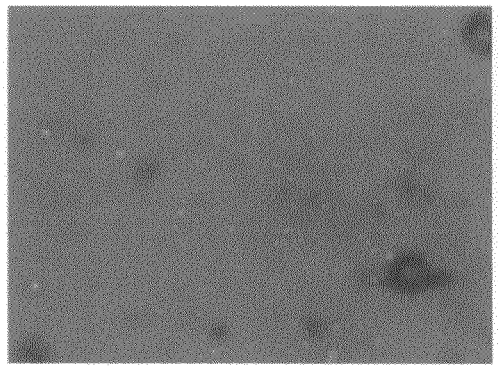
Figure 44:
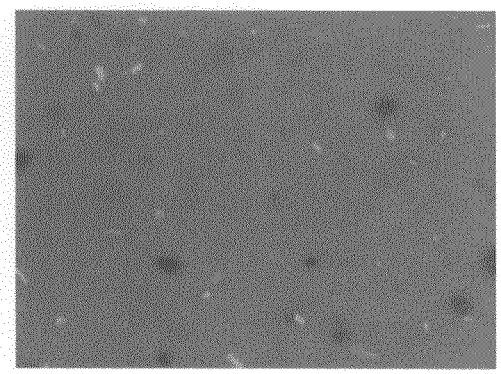
Figure 44:
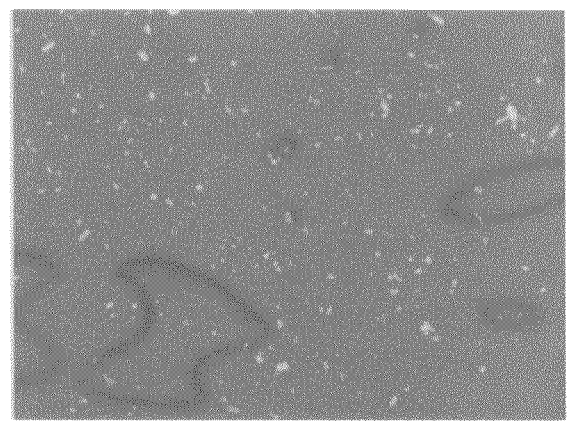
Figure 45:
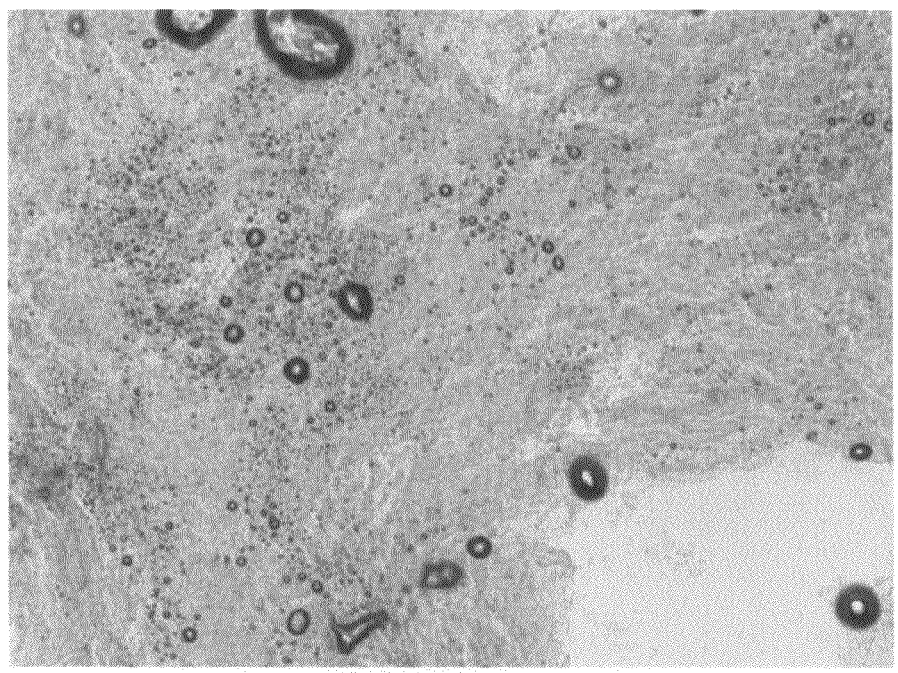
FIG. 45 depicts a transmitted light micrograph of the 17-AG/PVP dispersion made by lyophilization from 3:1 t-BuOH/water, dissolved in water.

DSC: A check ("✓") indicates identification of a glass transition temperature (Tg), no apparent crystal endotherm. Exemplary micrographs are shown in FIG. 44 and FIG. 45 (amorphous dispersion visualized under PLM).

XRPD: A check indicates no crystalline signature.

In vitro Dissolution: A check indicates a supersaturated level of 17-AG of at least 0.4 mg/ml (50% of 12% 17-AG K-30).

HNMR: A check ("✓") indicates a spectrum consistent with the expected structure and one that shows <5% residual solvents.

LCUV: A check indicates >95% purity.

Stability: A check a check ("✓") indicates TG-DSC >40° C. above RT, >1 month stability (room temperature by LCUV, DSC, microscopy.

Characteristics of Amorphous 17-AG Solid Dispersions in Various Polymers

|  | 17-AG in PVP | 17-AG in Eudragit | 17-AG in Plasdone | 17-AG in HPMCP | 17-AG in HPMCAS |
|---|---|---|---|---|---|
| Visual (PLM)-solid | ✓ | ✓ | ✓ | ✓ | ✓ |
| Visual-dissolved in water | ✓ | ✓ | ✓ | ✓ | ✓ |
| $^1$H NMR | ✓ | ✓ | ✓ | ✓ | ✓ |
| TG-DSC | ✓ | ✓ | ✓ | ✓ | ✓ |
| XRPD (@ 33% load) | ✓ | ✓ | ✓ | ✓ | ✓ |
| Purity | ✓ | ✓ | ✓ | ✓ | ✓ |

Preparation of Samples for in-vitro Dissolution: A series of scintillation vials was used to prepare samples according to the following table, containing 17-AG (20% load) polymer dispersion (50.0 mg). To each vial was added simulated intestinal fluid (5 mL) and each was shaken at 37° C. At 5-, 15-, 30-, 60-, 90, -120-min, 4-hour, 8-hour and overnight timepoints, aliquots (300 uL) of each suspension were drawn and filtered via polypropylene filter (0.45 micron) into MeOH (750 uL). The samples were then diluted in MeOH and tested using UV method for solution concentration. The results of each sample are summarized in the following tables.

Dissolution Experiment Setup

| Sample | Dispersion weight (mg) | 17-AG (mg) | Target Conc (mg/mL) | Polymer from dispersion (mg) | Polymer (%) | Solution volume (mL) |
|---|---|---|---|---|---|---|
| 17-AG in PVP | 50.0 | 10 | 2 | 40.0 | 0.80 | 5 |
| 17-AG in HPMCP | 50.0 | 10 | 2 | 40.0 | 0.80 | 5 |
| 17-AG in HPMCAS | 50.0 | 10 | 2 | 40.0 | 0.80 | 5 |
| 17-AG in Plasdone S-630 | 50.0 | 10 | 2 | 40.0 | 0.80 | 5 |
| 17-AG in Eudragit L100 | 50.0 | 10 | 2 | 40.0 | 0.80 | 5 |

The following are data collected from an in vitro dissolution study demonstrating that supersaturated levels of 17-AG are achieved, relative to equilibrium solubility, when crystallization inhibitors are used to prepare solid dispersion formulations (resulting in supersaturated levels of 17-AG when measured by dissolution in vitro). Such formulations can be prepared utilizing various types of crystallization inhibitors or polymers (other than PVP). Exemplary crystallization inhibitors utilized are HPMCP, HPMCAS, Plasone S-630 and Eudragit L100.

Dissolution Summary Results

| Polymer | 17-AG Load (w/w %) | Equilibrium solubility of 17-AG in SIF @ 37° C. (mg/mL) | Supersaturated Concentration of 17-AG from Various Polymer dispersions in SIF @ 37° C. (mg/mL) (t = 5 min) |
|---|---|---|---|
| PVP K30 | 20 | 0.004 | 0.459 mg/mL (100X)* |

-continued

| Polymer | 17-AG Load (w/w %) | Equilibrium solubility of 17-AG in SIF @ 37° C. (mg/mL) | Supersaturated Concentration of 17-AG from Various Polymer dispersions in SIF @ 37° C. (mg/mL) (t = 5 min) |
|---|---|---|---|
| HPMCP HP-55 | 20 | 0.004 | 0.250 mg/mL (60X)* |
| HPMCAS HG | 20 | 0.004 | 0.283 mg/mL (70X)* |
| Plasdone S-630 | 20 | 0.004 | 0.522 mg/mL (130X)* |
| Eudragit L100 | 20 | 0.004 | 0.420 mg/mL (100X)* |

*Fold increase relative to 17-AG equilibrium solubility

Figure 13:
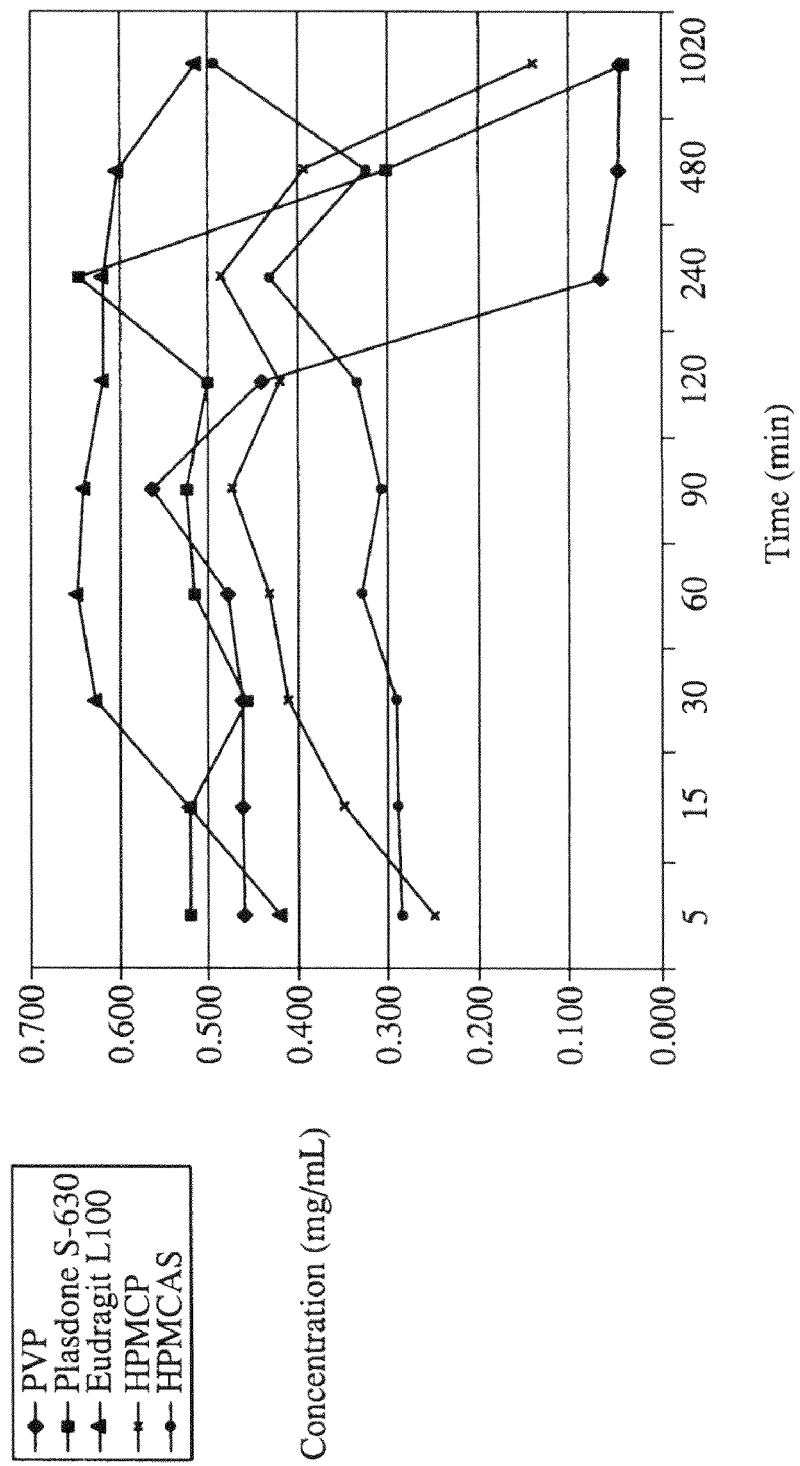
FIG. 13 depicts a graph showing results from an in vitro dissolution study of various 17-AG/polymer dispersions, plotted as a function of mg/ml versus time (minutes).

FIG. 13 shows the in vitro dissolution of 17-AG dispersions made using the above various crystallization inhibitors.

Amorphous dispersions can be made using other geldanamycin analogs as well. To similarly demonstrate that compounds other than 17-AG benefit from the addition of a crystallization inhibitor, Example 21 below is an in-vitro dissolution study demonstrating that supersaturated concentrations of geldanamycin analogs can be achieved when a crystallization inhibitor is added to a substantially amorphous solid dispersion formulation, which may also result in improved in vivo bioavailability as seen for the analog 17-AG. Such formulation can be prepared utilizing various geldanamycin analogs. Particular analogs utilized are 17-benzyl-AG, 17-fluoroethyl-AG, 17-cyclopropylmethyl-AG, 17-acetyl-AG, 17-azetidinyl-G, 11-acetyl-17-AG and 11-oxo-17-AG. The results of each analog are summarized in the below tables in Example 21.

Example 21

Preparation of Amorphous Solid Dispersion Formulations Using Various Geldanamycin Analogs [17-AG (12% Load) Plus PVP]

A mixture of a geldanamycin compound and solvent is heated and stirred vigorously. Aliquots are periodically taken and examined via polarized light microscopy to determine complete dissolution of the crystalline material. Upon complete dissolution, the crystallization inhibitor is slowly added to the solution. The mixture is stirred vigorously with heat, and aliquots are taken and examined via microscopy to ensure complete dissolution of the components. Alternatively, the order of addition can be changed so that the polymer is used as a co-solvent, e.g., the compound is added to a pre-mixed solution of the polymer and the appropriate ratio or combination of solvents. The dispersions were characterized as described above.

Characteristics of Amorphous Solid Dispersions of Geldanamycin Analogs

| | 17-benzyl-AG | 17-fluoroethyl-AG | 17-cyclopropylmethyl-AG | 17-acetyl-AG | 17-azetidinyl-AG | 11-acetyl-17-AG | 11-oxo-17-AG | 17-AG |
|---|---|---|---|---|---|---|---|---|
| Visual-solid | ✓ | ✓ | ✓ | ✓ | ✓ | ✓ | ✓ | ✓ |
| Visual-solubility | ✓ | ✓ | ✓ | ✓ | ✓ | ✓ | ✓ | ✓ |
| $^1$H NMR | ✓ | ✓ | ✓ | ✓ | ✓ | ✓ | ✓ | ✓ |
| DSC-$T_g$ | ✓ | ✓ | ✓ | ✓ | ✓ | ✓ | ✓ | ✓ |
| DSC crystallinity | ✓ | ✓ | ✓ | ✓ | ✓ | ✓ | ✓ | ✓ |
| Purity | ✓ | ✓ | ✓ | ✓ | ✓ | ✓ | ✓ | ✓ |

Using a procedure similar to Example 20, a series of scintillation vials was prepared according to the table below, except that analogs of 17-AG (12% load) plus PVP K-30 (83.3 mg) were used accordingly.

Dissolution Experiment Setup

| Sample | Dispersion weight (mg) | Analog amount (mg) | Target Conc (mg/mL) | PVP from dispersion (mg) | PVP (%) | Solution volume (mL) |
|---|---|---|---|---|---|---|
| 17-AG | 83.3 | 10 | 2 | 73 | 1.47 | 5 |
| 17-benzyl-AG | 83.3 | 10 | 2 | 73 | 1.47 | 5 |
| 17-fluoroethyl-AG | 83.3 | 10 | 2 | 73 | 1.47 | 5 |
| 17-cyclopropylmethyl-AG | 83.3 | 10 | 2 | 73 | 1.47 | 5 |
| 17-acetyl-AG | 83.3 | 10 | 2 | 73 | 1.47 | 5 |
| 17-azetidinyl-G | 83.3 | 10 | 2 | 73 | 1.47 | 5 |
| 11-acetyl-17-AG | 83.3 | 10 | 2 | 73 | 1.47 | 5 |
| 11-oxo-17-AG | 83.3 | 10 | 2 | 73 | 1.47 | 5 |

Figure 15:
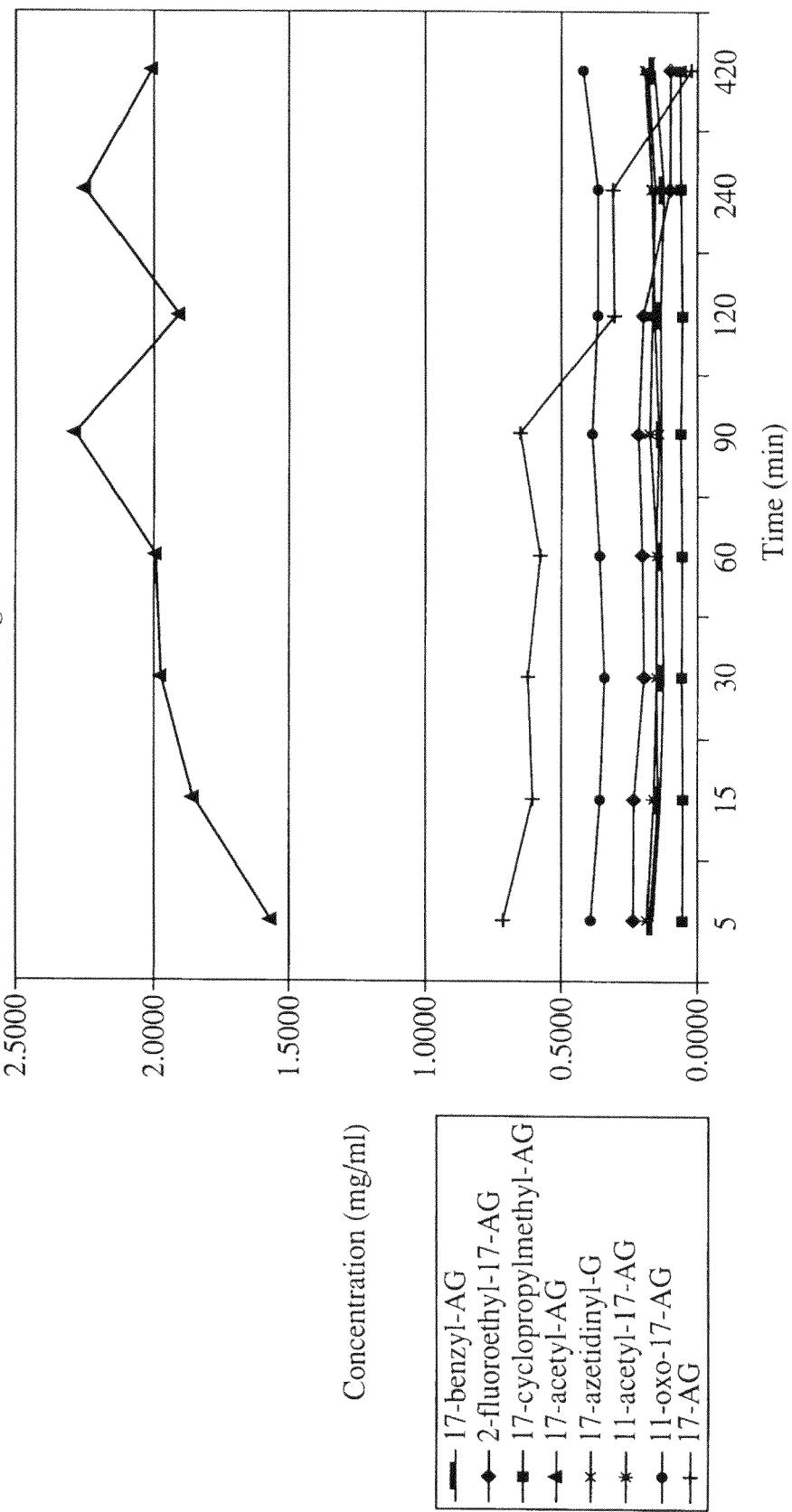
FIG. 15 depicts an in vitro dissolution study in SIF of amorphous dispersions of a series of ansamycin analogs generated from PVP utilizing rotary evaporation, plotted as a function of mg/ml versus time (minutes).

Summarized below are the results from an in-vitro dissolution study for dispersions containing amorphous material made using a wide variety of ansamycin compound analogs. The data demonstrate that supersaturated levels of a variety of ansamycin compounds can be achieved. The dissolution profile of amorphous dispersions of the series of ansamycin analogs generated from PVP utilizing rotary evaporation is found in FIG. 15.

Geldanamycin Analog Summary Results

| Analog | Eq. Solubility of active (mg/mL) | Supersaturated concentration of analog/polymer dispersions in SIF at 37° C. (mg/ml) (t = 5 min) |
|---|---|---|
| 17-AG | 0.004 | 0.712 mg/ml (200x) |
| 17-fluoroethyl-AG | 0.015 | 0.165 mg/ml (10x) |
| 17-fluoroethyl-AG | 0.040 | 0.234 mg/ml (5x) |
| 17-cyclopropylmethyl-AG | 0.034 | 0.0573 mg/ml (2x) |
| 17-acetyl-AG | 0.350 | 1.568 mg/ml (≧5x) |
| 17-azetidinyl-G | 0.140 | 0.167 mg/ml (0x) |
| 11-acetyl-17-AG | 0.088 | 0.167 mg/ml (2x) |
| 11-oxo-17-AG | 0.330 | 0.395 mg/ml (0x) |

*Fold increase relative to equilibrium solubility

Figure 16:
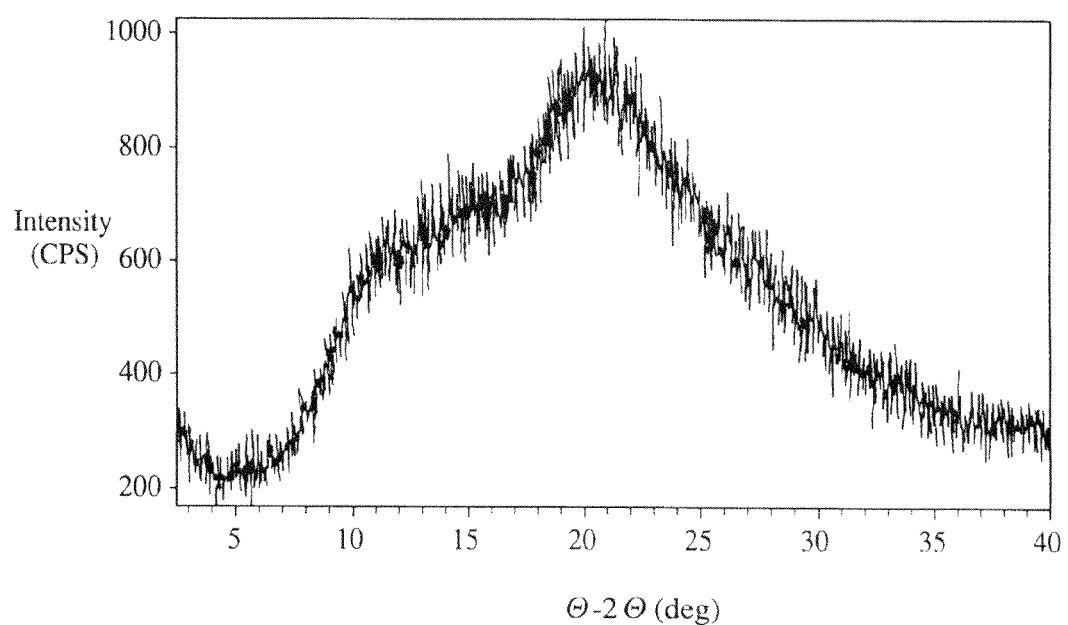
FIG. 16 depicts an XRPD pattern for an amorphous dispersion of 17-AG plus PVP (20% in K-30) made by rotary evaporation.
Figure 17:
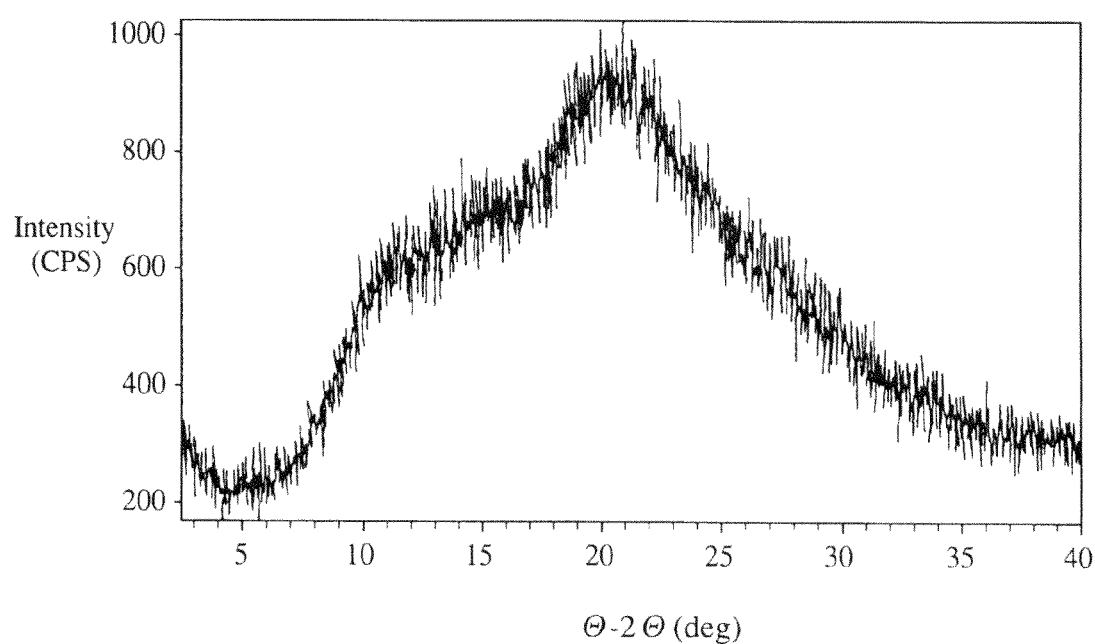
FIG. 17 depicts an XRPD pattern for an amorphous dispersion of 17-AG plus PVP spiked with 0.1% crystalline Form I.
Figure 18:
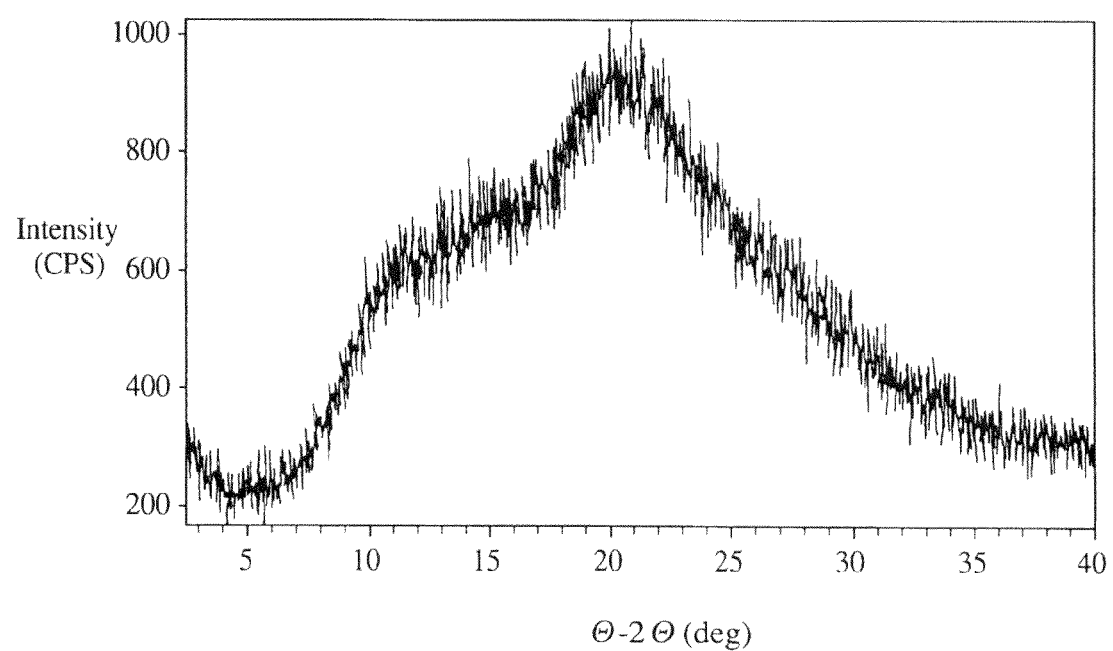
FIG. 18 depicts an XRPD pattern for an amorphous dispersion of 17-AG plus PVP spiked with 1% crystalline Form I.
Figure 19:
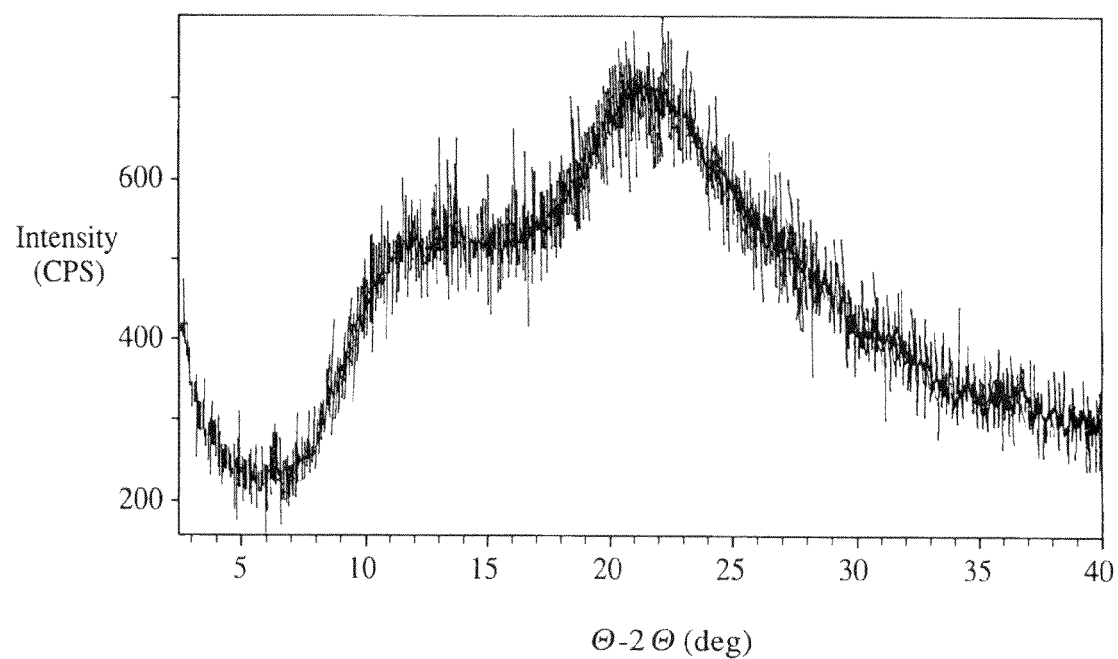
FIG. 19 depicts an XRPD pattern for an amorphous dispersion of 17-AG plus PVP spiked with spiked with 5% crystalline Form I.
Figure 20:
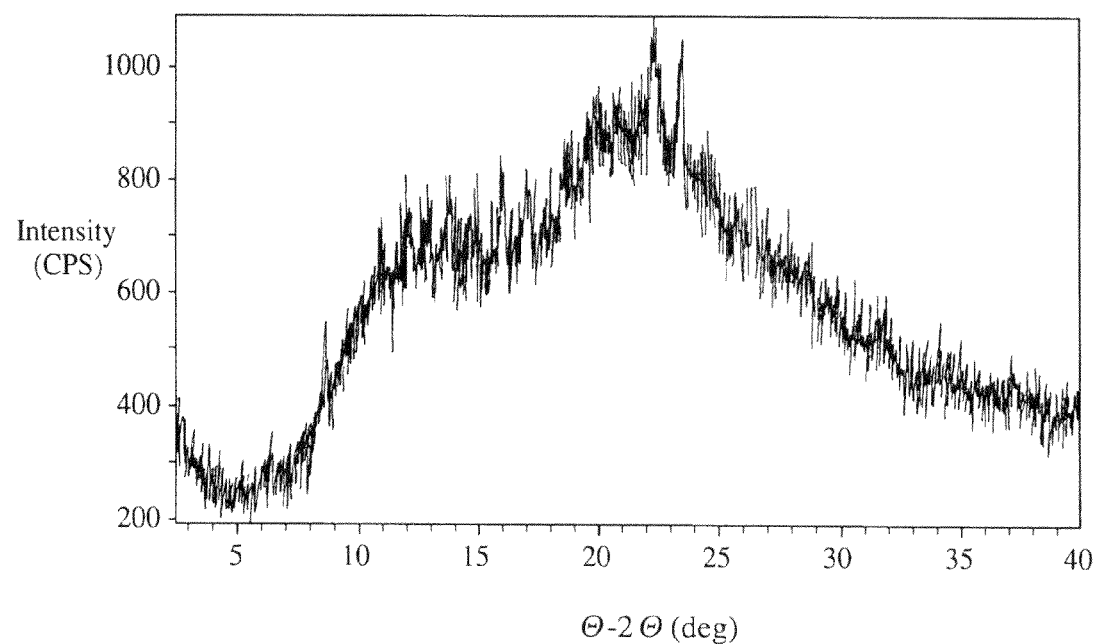
FIG. 20 depicts an XRPD pattern for an amorphous dispersion of 17-AG plus PVP spiked with spiked with 10% crystalline Form I.
Figure 21:
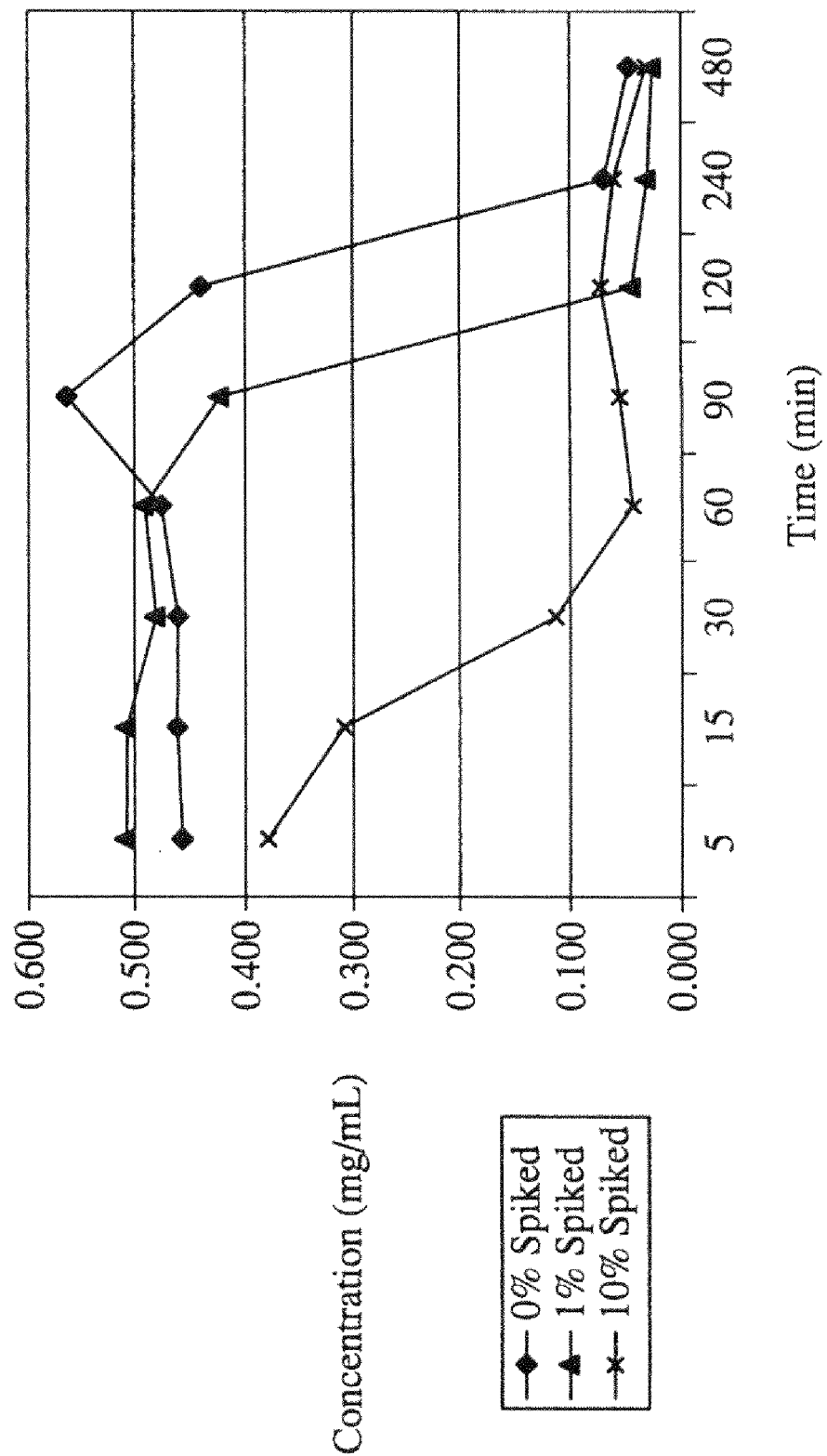
FIG. 21 depicts a graph showing results from an in vitro dissolution study of a 17-AG/PVP dispersion containing varying amounts of Form I 17-AG (0%, 1% and 10%), plotted as a function of mg/ml versus time (minutes), demonstrating the effect of varying amounts of Form I on the stability of supersaturated solutions.
Figure 22:
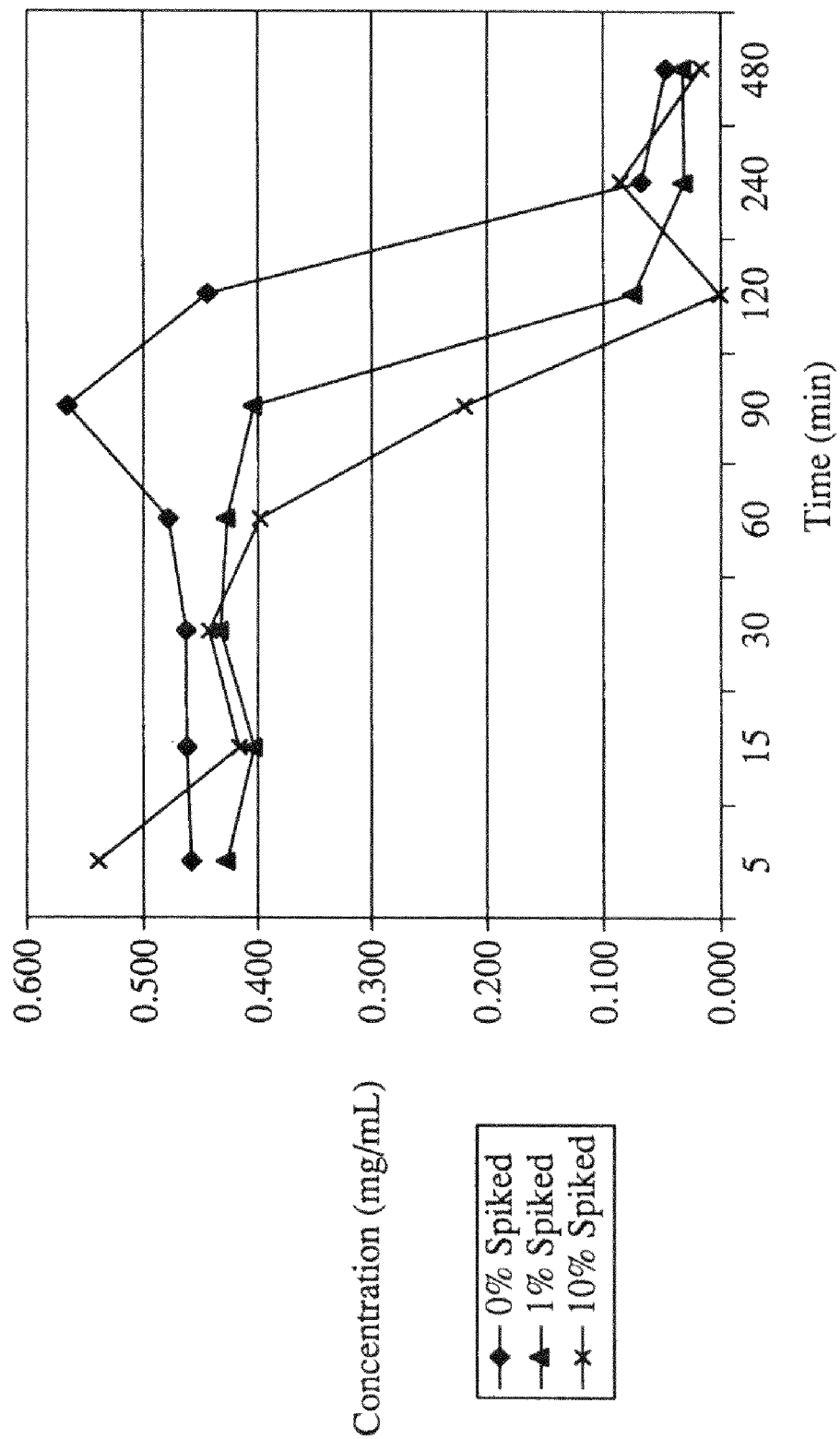
FIG. 22 depicts a graph showing results from an in vitro dissolution study of a 17-AG/PVP dispersion containing varying amounts of Form II 17-AG (0%, 1% and 10%), plotted as a function of mg/ml versus time (minutes), demonstrating the effect of varying amounts of Form II on the stability of supersaturated solutions.
Figure 23:
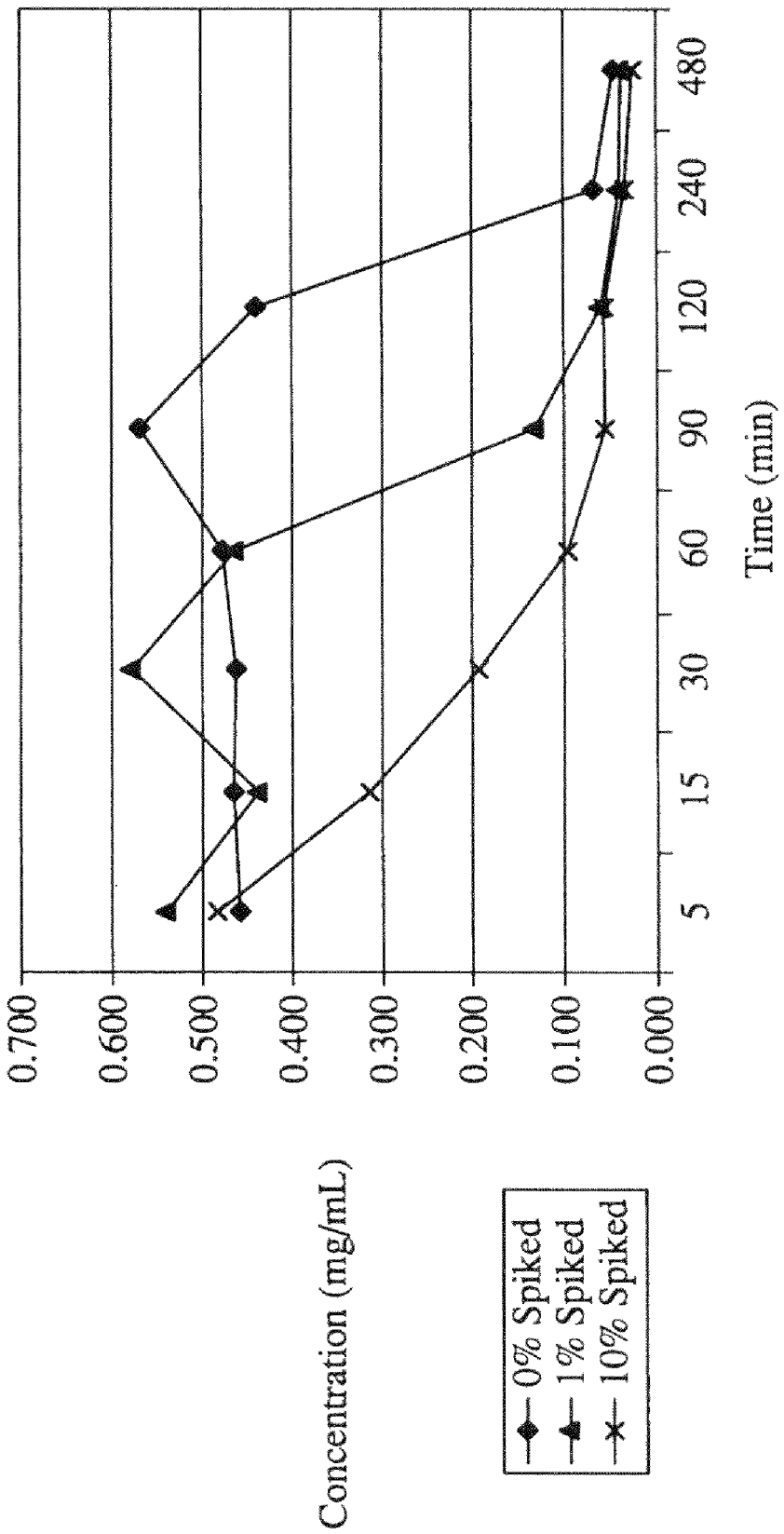
FIG. 23 depicts a graph showing results from an in vitro dissolution study of a 17-AG/PVP dispersion containing varying amounts of Form III 17-AG (0%, 1% and 10%), plotted as a function of mg/ml versus time (minutes), demonstrating the effect of varying amounts of Form III on the stability of supersaturated solutions.

Example 22 below demonstrates that supersaturated solutions of 17-AG generated from substantially amorphous solid dispersion formulations that have been "spiked" with various amounts of crystalline material (0.01%, 0.1% 1% and 10%, with 0% as a comparator) demonstrate altered precipitation kinetics of 17-AG. Adding various amounts of crystalline material to the amorphous dispersions of 17-AG affects the stability of the corresponding supersaturated solution. Increasing amounts of crystalline material present in the supersaturated solutions increases the rate of 17-AG nucleation and precipitation. The in vitro experimental dissolution protocol of each spiked formulation is summarized in the tables below. A representative DSC of 20% 17-AG in PVP-K30 is found in FIG. 16. Additional data illustrating various amounts of Spiking with Form I are found in FIGS. 16, 17, 18, 19, 20, 21, 22 and 23. Spiking with Forms II and III results in similar findings. As shown in these Figures, there is a measurable difference between the formulations containing "0%" crystalline material, and the formulations spiked with 1% crystalline material, demonstrating that the formulation designated "0%" contains less than 1% crystalline material.

Example 22

Dissolution Study Using 17-AG in Spiking Experiment

To 1 dram vials containing a solid dispersion of 17-AG (20% load) plus PVP K30 were added various amount of 17-AG Form I to provide a total mass of 500 mg and crystalline range from 0.01 to 10%. To ensure homogenous mixtures of dispersion and crystalline 17-AG, the mixtures were ground with mortar and pestle, sieved through a No. 50 screen (300 um) and mixed for 5 minutes using a Turbula Mixer. The amount of crystalline material was examined by microscopy. Substantially amorphous material had no visible crystalline material and no birefringence under cross polarized light with dry material and upon introduction of water.

| Sample | Amount of dispersion (mg) | 17-AG added (mg) | Total material (mg) | % of crystalline material | FIG. Reference No. |
|---|---|---|---|---|---|
| 0% Spiked | 500.0 | 0.0 | 500.0 | 0 | 44(A) and 44(B) |
| 0.01% Spiked | 999.9 | 0.1 | 1000.0 | 0.01 | 44(C) |
| 0.1% Spiked | 499.5 | 0.5 | 500.0 | 0.1 | 44(D) |
| 1% Spiked | 495.0 | 5.0 | 500.0 | 1 | 44(E) |
| 10% Spiked | 450.0 | 50.0 | 500.0 | 10 | — |

To a scintillation vial containing the prepared spiked solid dispersions, (prepared according to the schedule in the table below) was added simulated intestinal fluid (5 mL); the vials were then shaken at 37° C. At 5-, 15-, 30-, 60-, 90, -120-min, 4-hour, 8-hour and overnight time-points, aliquots (300 uL) of each sample were drawn and filtered via a polypropylene filter (0.45 micron) into MeOH (750 uL). The samples were then diluted in MeOH and tested using UV method for solution concentration. The results are summarized in the following table.

Additionally, FIG. 44(B) and FIG. 44(C) show a visual difference between a non-spiked dispersion and a dispersion spiked with 0.01% crystalline material, demonstrating that the non-spiked dispersion contains less than 0.01% crystalline material.

Spiking Experiment Dissolution Study-Sample Preparation

| Sample | Dispersion weight (mg) | Sample amount (mg) | Conc (mg/mL) | PVP from dispersion (mg) | PVP add back (mg) | Total material (mg) | % PVP | Solution volume (mL) |
|---|---|---|---|---|---|---|---|---|
| 0% Spiked | 50.0 | 10 | 2 | 40 | 0 | 50.0 | 0.80 | 5 |
| 0.01% Spiked | 50.0 | 10 | 2 | 40 | 0 | 50.0 | 0.80 | 5 |
| 0.1% Spiked | 50.0 | 10 | 2 | 40 | 0 | 50.0 | 0.80 | 5 |
| 1% Spiked | 48.1 | 10 | 2 | 38.1 | 1.9 | 50.0 | 0.80 | 5 |
| 10% Spiked | 35.7 | 10 | 2 | 25.7 | 14.3 | 50.0 | 0.80 | 5 |

Example 23

Control of Release Rate for 17-AG/PVP Dispersion Solid Dose Forms

To demonstrate that the control of the release rate of 17-AG from 17-AG plus PVP dispersions is feasible, tablets and capsules were made of varying composition/excipients from a 20% 17-AG plus PVP K30 dispersion which have immediate, extended, and slow release rates as measured by in-vitro dissolution. As such, controlling the dissolution rate, in Example 24 below, of solid dose forms of 17-AG amorphous dispersions could provide a means of controlling the degree of supersaturation of dissolved 17-AG when dosed in-vivo. The composition of the tablets and capsule are described in the following table.

| Dose Name | Form | Composition |
|---|---|---|
| 25 mg capsule | capsule | 100% 20% IPI-493 PVP rotary evaporation DPI, size 4 HPMC capsule |
| 50 mg capsule | capsule | 100% 20% IPI-493 PVP rotary evaporation DPI, size 2 HPMC capsule |
| Tablet 1 | tablet | 79.5% 20% IPI-493 PVP spray dried DPI, 20% Explotab, 0.5% magnesium stearate, hard compression |
| Tablet 2 | tablet | 89.5% 20% IPI-493 PVP spray dried DPI, 10% Explotab, 0.5% magnesium stearate, hard compression |
| Tablet 3 | tablet | 95.5% 20% IPI-493 PVP spray dried DPI,, 4% Explotab, 0.5% magnesium stearate, soft compression |
| Tablet 4 | tablet | 95.5% 20% IPI-493 PVP spray dried DPI, 4% Explotab, 0.5% magnesium stearate, hard compression |

Rate of release and level of dissolved 17-AG was measured by dissolving the tested tablet or capsule in 500 ml SIF pH 6.8 and stirred in a dissolution apparatus (Paddle speed 150 RPM, 37° C.) until completely dissolved. Aliquots of the tablet/capsule-SIF solution were removed at 15, 30, 90, 120, 180, & 240 minute timepoints. Sample aliquots were filtered (0.45 uM PVDF), diluted in SIF/MeOH and measured in triplicate on UV spectrometer.

Figure 24:
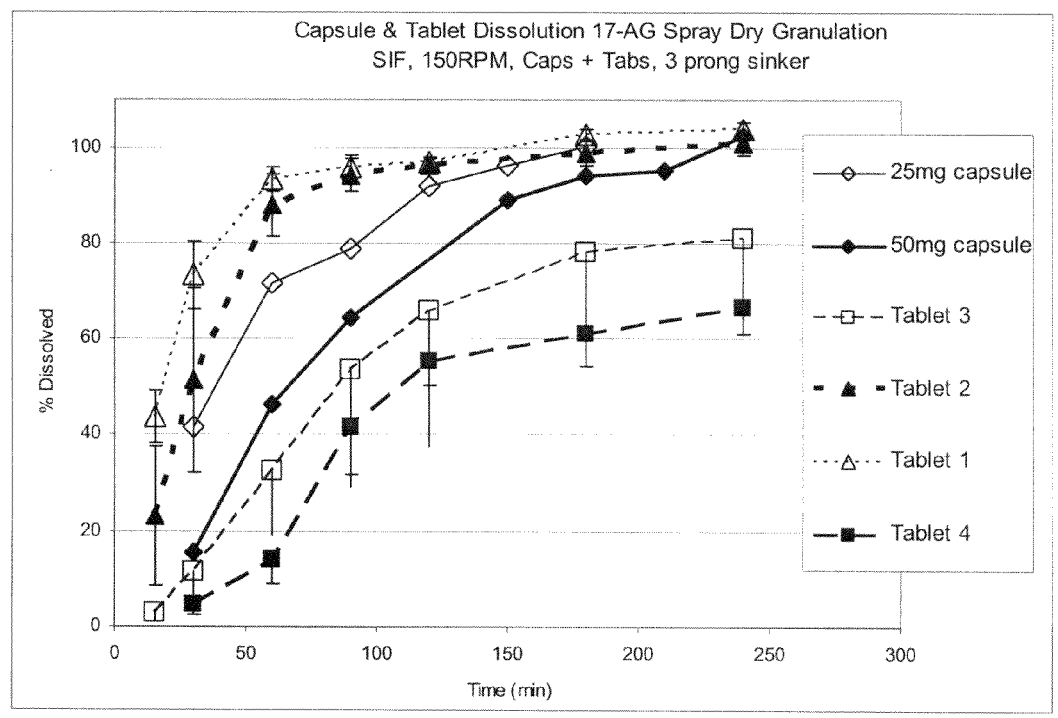
FIG. 24 depicts a graph showing the dissolution profile of 17-AG from different tablets and capsule (average values, in-vitro dissolution in SIF), demonstrating different dissolution/release profiles are possible with tablets of varying composition.

The dissolution profile of 17-AG from the different tablets and capsules is shown in the graph in FIG. 24. As demonstrated in the results, it is possible to produce tablets and capsules with different in-vitro release rates (immediate, extended, & slow).

Example 24

Effect of Crystallization Inhibitors on Supersaturation

Crystallization inhibitors such as PVP (polyvinylpyrrolidone, Povidone) can improve the solubility of compounds by preventing crystallization. The effect of PVP on the amount of solvated 17-AG was investigated by measuring levels of 17-AG in SIF pH 6.8 (simulated intestinal fluid) solutions with increasing amounts of PVP at various time points following the addition of specific amounts of 17-AG, either in crystalline form or in DMSO solutions to supersaturated levels.

Equilibrium solubility of crystalline 17-AG was measured at specific time points by addition of crystalline 17-AG to SIF pH 6.8 containing 0%, 0.5%, 1%, 2.5%, & 5% PVP (w/v) to a concentration of 5 mg/ml. Solutions were placed at 37° C., and sample aliquots were removed at 24, 48, 72, & 96 hours. Sample aliquots were filtered (0.45 uM PVDF), diluted in SIF/MeOH and measured in triplicate on UV spectrometer.

Figure 25:
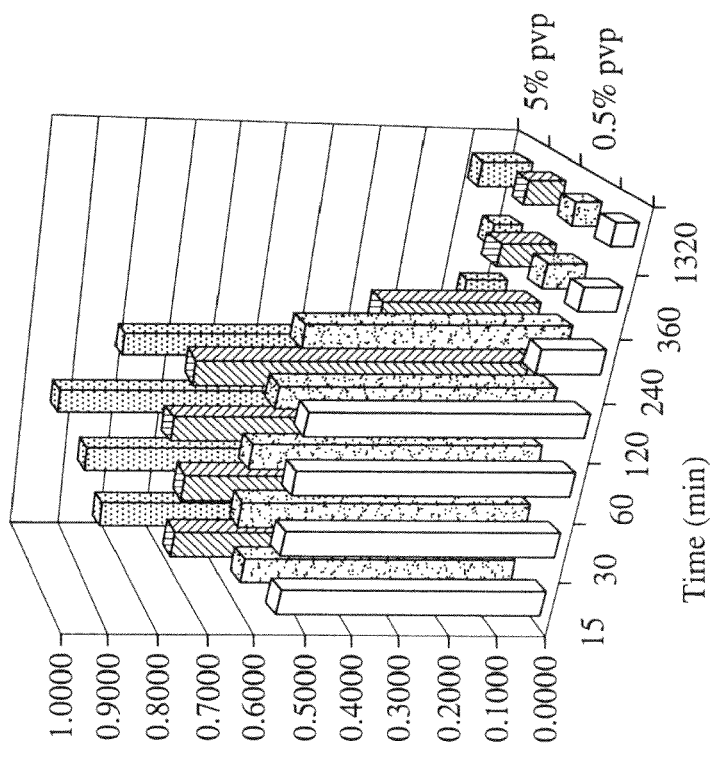
FIG. 25 on the left, depicts a three-dimensional bar graph of an in-vitro dissolution study using 0.5 mg/ml 17-AG in various SIF solutions containing 0%, 0.5%, 1.5% and 5% PVP (50 mg/ml 17-AG in DMSO diluted 1:100 into SIF); and on the right, depicts a three-dimensional bar graph of an in-vitro solubility study using 1.0 mg/ml 17-AG in various SIF solutions containing 0%, 0.5%, 1.5% and 5% PVP (100 mg/ml 17-AG in DMSO diluted 1:100 into SIF); together demonstrating that varied amounts of PVP achieve supersaturation levels of 17-AG and stabilizes the supersaturated solutions by preventing nucleation/precipitation of 17-AG.
Figure 25:
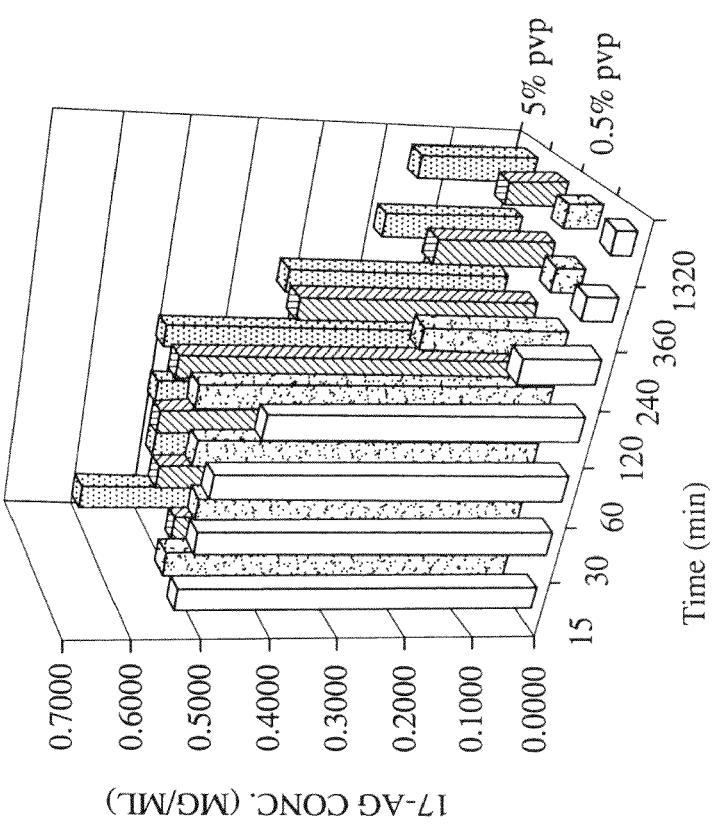
Figure 26:
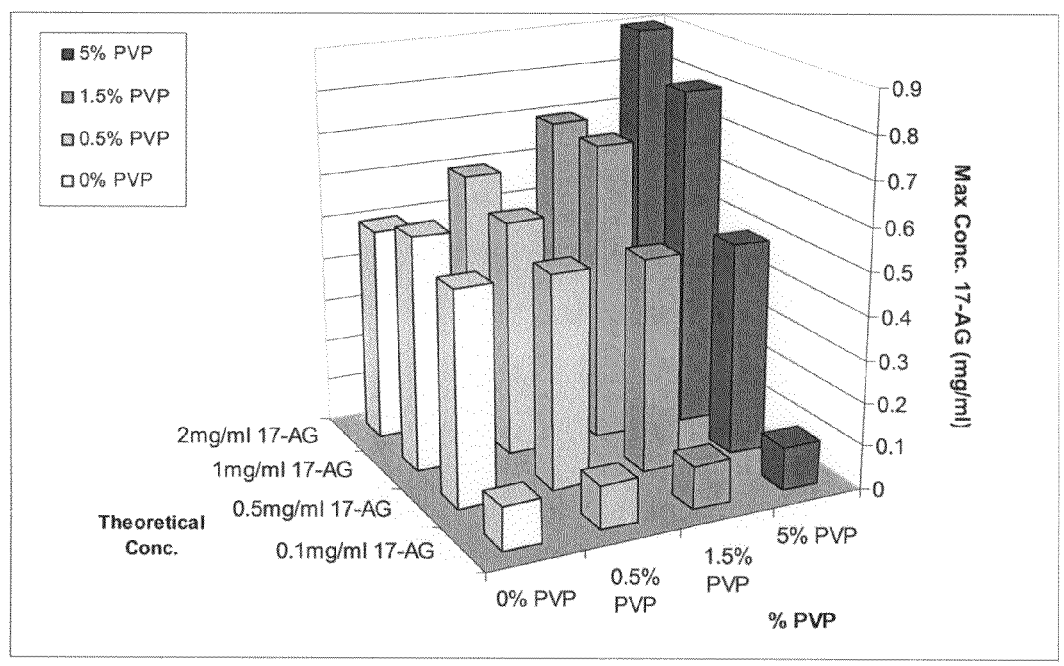
FIG. 26 depicts a three-dimensional bar graph demonstrating that varied amounts of PVP in SIF will change the degree of supersaturation of 17-AG in SIF, i.e., higher amounts of PVP result in higher supersaturated levels of 17-AG.

Supersaturated levels of 17-AG was measured by adding 17-AG DMSO stock solutions (10, 50, 100, & 200 mg/ml) at a 1:100 dilution to SIF pH 6.8 solutions containing 0%, 0.5%, 1%, 2.5%, & 5% PVP (w/v). This resulted in solutions with final 17-AG concentrations of 0.1, 0.5, 1, & 2 mg/ml respectively for each of the SIF pH 6.8 PVP solutions. Solutions were stirred in a dissolution apparatus (Paddle speed 150 RPM, 37° C.), and aliquots of each solution were removed at 15, 30, 60, 120, 240, 360, & 1320 minute time points. Sample aliquots were filtered (0.45 uM PVDF), diluted in SIF/MeOH and measured in triplicate on UV spectrometer. Representative data are found in FIG. 25 and FIG. 26.

Summary of 17-AG Solubility Results (Average Values)

| SIF pH 6.8 solution-% PVP | Crystalline 17-AG Equilibrium Solubility (mg/ml) | 17-AG Supersaturated Concentration (mg/ml) |
|---|---|---|
| 0% PVP | 0.0041 | 0.5 |
| 0.5% PVP | 0.0059 | 0.6 |
| 1.0% PVP | 0.0065 | 0.7 |
| 2.5% PVP | 0.0087 | — |
| 5.0% PVP | 0.0112 | 0.9 |

As shown above, PVP improves the levels of solvated 17-AG. The equilibrium solubility of crystalline 17-AG increases almost 3-fold from 0.0041 mg/ml in SIF pH 6.8 with 0% PVP to 0.0112 mg/ml in SIF pH 6.8 with 5% PVP. In addition, the degree of supersaturation of 17-AG increases almost 2-fold from 0.5 mg/ml at 0% PVP to 0.9 mg/ml at 5% PVP.

Figure 27:
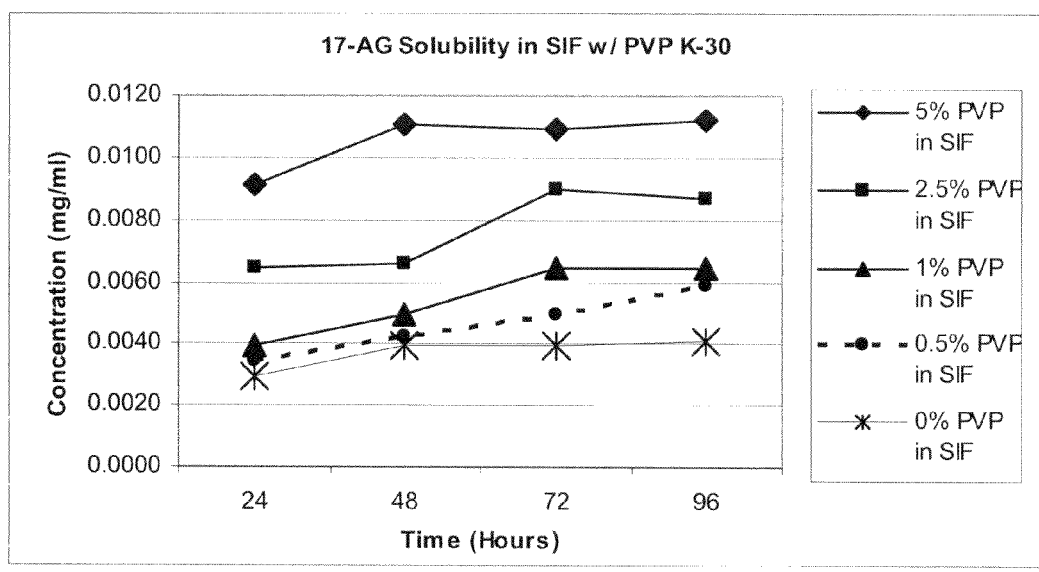
FIG. 27 depicts a graph of the equilibrium solubility of 17-AG in SIF containing varying amounts of PVP K-30 (0%, 0.5%, 1%, 2.5% and 5%), plotted as a function of mg/ml versus time, demonstrating that adding PVP increases the equilibrium solubility of 17-AG in simulated intestinal fluid (SIF).

In addition, PVP enhances the stability of the supersaturated solutions by prolonging the duration of the supersaturated state. In SIF without PVP, 17-AG starts to precipitate and come out of solution at approximately 120 minutes. In SIF solutions with PVP, the 17-AG supersaturated state can be prolonged beyond 120 minutes to almost 240 minutes. The rate of 17-AG precipitation is also attenuated by PVP in a concentration dependent manner, i.e. the higher % PVP, the slower the rate of 17-AG precipitation from the supersaturated state. However, it appears that this crystallization rate inhibitory effect of PVP can be overcome by precipitation of 17-AG from very high supersaturated levels as seen in the result of the 1.0 mg/ml solution in 5% PVP which achieves a supersaturated state of 0.9 mg/ml; however starts to precipitate out at 120 minutes. Representative data are shown in FIG. 27.

Example 25

Comparison of In Vivo Exposure in Beagle Dogs of 17-AG PVP Dispersions

The effects of varying compound load, PVP grade and particle size in 17-AG+PVP dispersions on oral bioavailability was investigated by dosing beagle dogs and measuring 17-AG levels in blood plasma at various time points following a single oral capsule dose.

The following 17-AG+PVP dispersions were made utilizing rotary evaporation and characterized for purity, residual solvent level, and amorphous content as described.

| 17-AG | PVP Grade | | |
|---|---|---|---|
| (% Load) | K15 | K30 | K90 |
| 12 | 12% 17-AG K15 | 12% 17-AG K30 | 12% 17-AG K90 |
| 20 | | 20% 17-AG K30 | |
| 30 | | 30% 17-AG K30 | |

Each 17-AG+PVP dispersion was filled into HPMC capsules and dosed into dogs at a level of 15 mg/kg. Blood was collected pre-dose, 15, 30 minutes, 1, 2, 4, 8, and 24 hours post dose into tubes containing sodium heparin. Collected blood samples were immediately placed on wet ice and refrigerated centrifuge for isolation of plasma within 30 min of collection. Isolated plasma was saved in labeled screw cap freezer vials or eppendorf tubes and stored frozen (−70° C.) until analyzed for plasma 17-AG levels. The design of the study is as follows. 2 groups of dogs were utilized for dosing, 2 males & 2 females per group, with a week washout in between each dose. For specifics of the animal dosing protocol, please refer to PCRS protocol No. INF-0704.

|       | Dog Group | Dose 1 | Dose 2 | Dose 3 | Dose 4 |
|-------|-----------|--------|--------|--------|--------|
| 17-AG Load | A | 12% 17-AG PVP K30 @15 mg/kg | 20% 17-AG PVP K30 @15 mg/kg | 30% 17-AG PVP K30 @15 mg/kg | 20% 17-AG PVP K30 <50 uM @10 mg/kg |
| PVP Grade | B | 12% 17-AG PVP K30 @15 mg/kg | 12% 17-AG PVP K15 @15 mg/kg | 12% 17-AG PVP K90 @15 mg/kg | 20% 17-AG PVP K30 >800 uM @10 mg/kg |

After analysis of 17-AG plasma levels following dosing, there was not a significant effect on exposure due to either 17-AG load or PVP grade; however, there are exposure trends. For 17-AG load, $C_{max}$ and AUC decreased with increasing 17-AG load (12%>20%>30% 17-AG). For PVP grade, $C_{max}$ and AUC were highest in PVP K30, followed by PVP K15, followed by PVP K90. No trends or affects on $C_{max}$ or AUC could be seen due to changes in particle size, i.e. exposure is robust across a large range of particle sizes. Overall, there were no consistent differences seen in the exposure data due to sex for the variables tested. Any variability observed in the exposure is most likely due to animal specific differences or in-life observations (i.e. dosing issues, emesis).

Figures 28A, 28B:
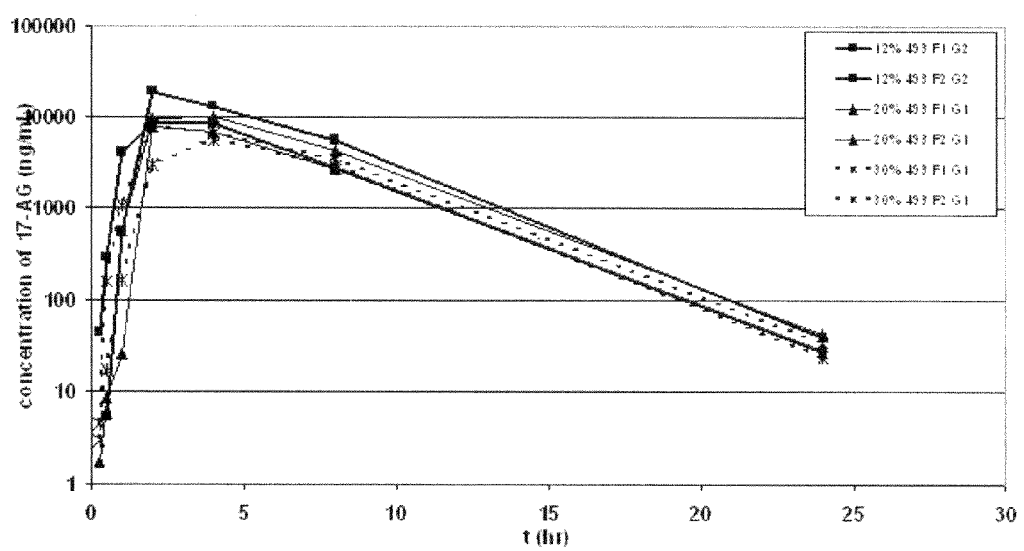
Figures 29A, 29B:
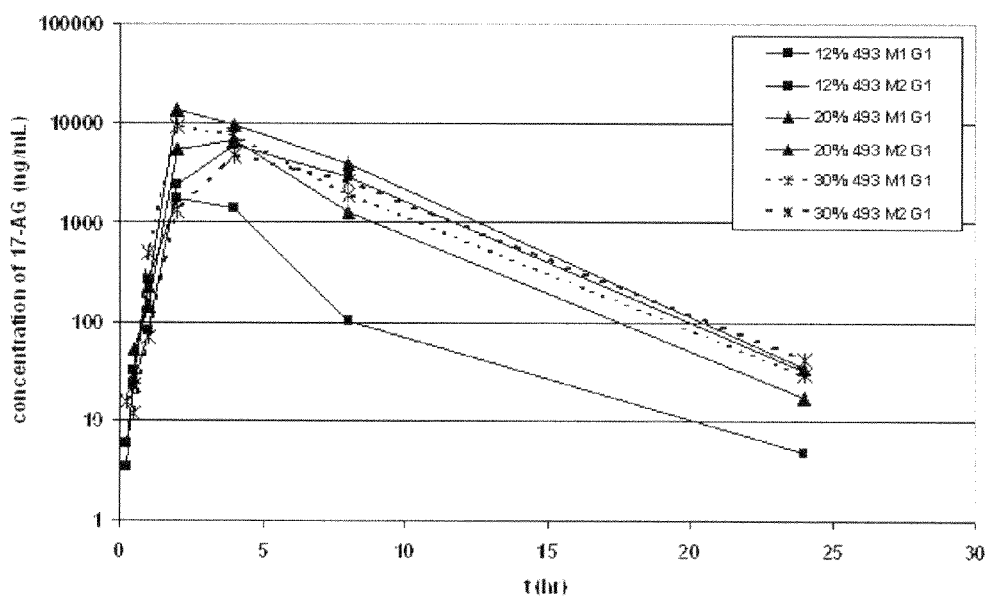
Figure 32:
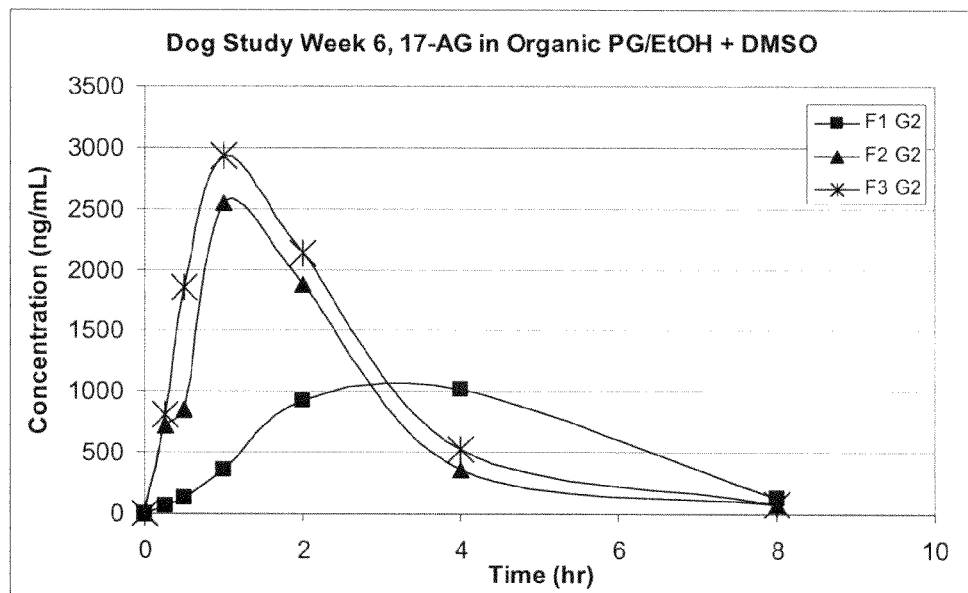
FIG. 32 depicts a graph of dog plasma level concentration after administration of 17-AG as a solution (85% propylene glycol, 5% ethanol and 10% DMSO) via oral gavage, without a crystallization inhibitor present, plotted as a function of ng/ml versus time (hours).
Figure 33:
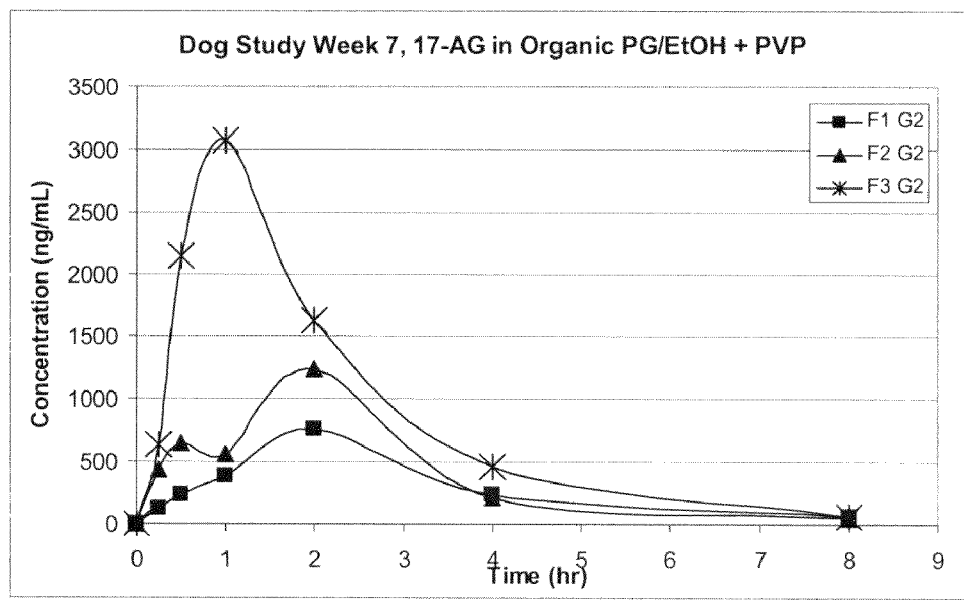
FIG. 33 depicts a graph of dog plasma level concentration after administration of 17-AG as a solution (85% propylene glycol, 5% ethanol and 10% PVP) via oral gavage containing a crystallization inhibitor (PVP), plotted as a function of ng/ml versus time (hours), demonstrating that solutions as well as solid dispersions are effective formulations for oral administration.
Figure 34:
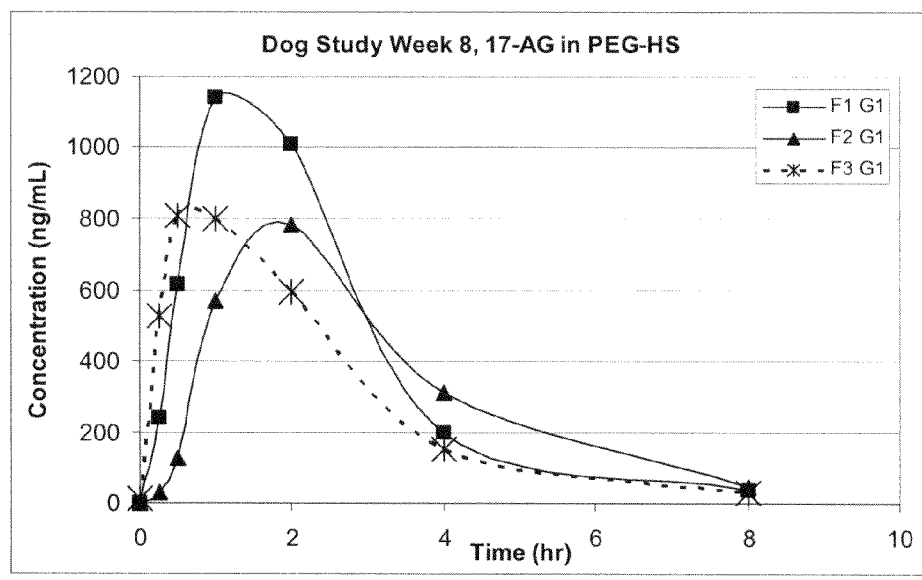
FIG. 34 depicts a graph of dog plasma level concentration after administration of 17-AG as a solution (20% polyethylene glycol-hydroxystearate, 5% DMSO in normal saline) via oral gavage, containing a crystallization inhibitor (PEG-HS), plotted as a function of ng/ml versus time (hours).
Figure 35:
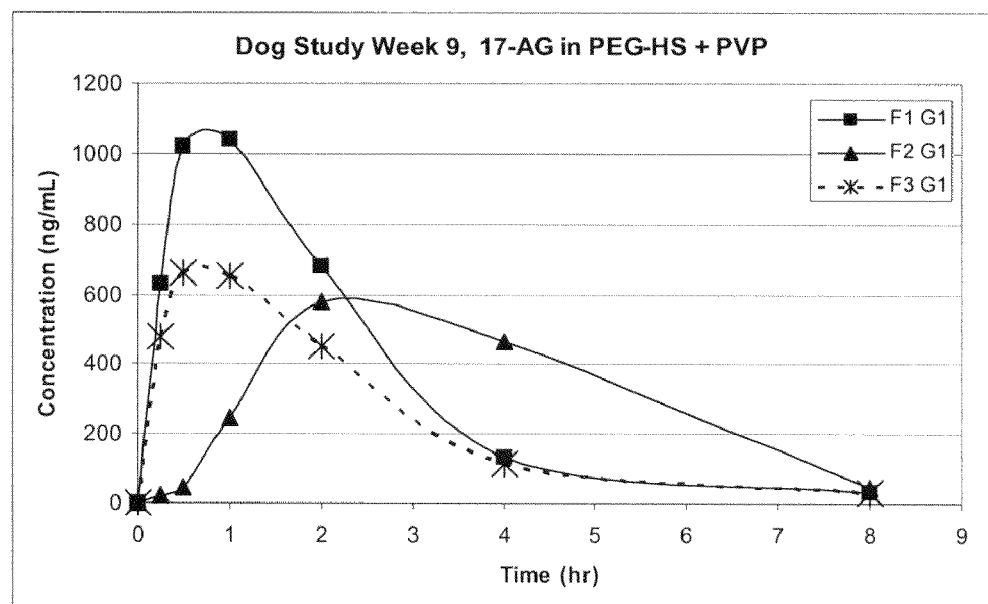
FIG. 35 depicts a graph of dog plasma level concentration after administration of 17-AG as a solution (20% polyethylene glycol-hydroxystearate, 5% DMSO, 10% PVP in normal saline) via oral gavage, containing a crystallization inhibitor (PEG-HS and PVP), plotted as a function of ng/ml versus time (hours).
Figure 36:
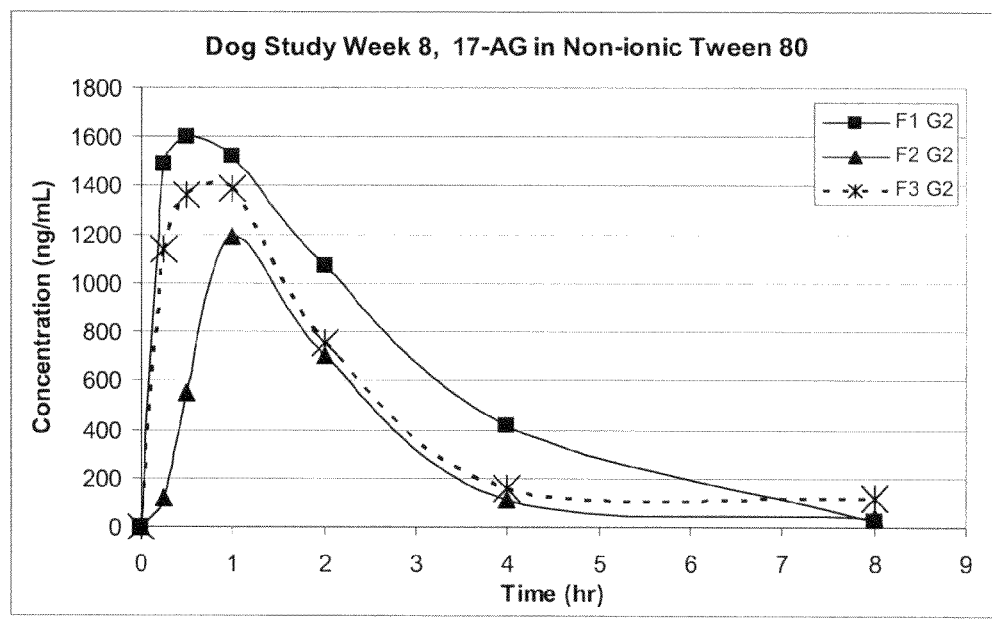
FIG. 36 depicts a graph of female dog plasma level concentration after administration if 17-AG as a solution (non-ionic 2% Tween-80, 5% DMSO in sterile water for injection) via oral gavage, containing a crystallization inhibitor (non-ionic Tween-80), plotted as a function of ng/ml versus time (hours).
Figure 37:
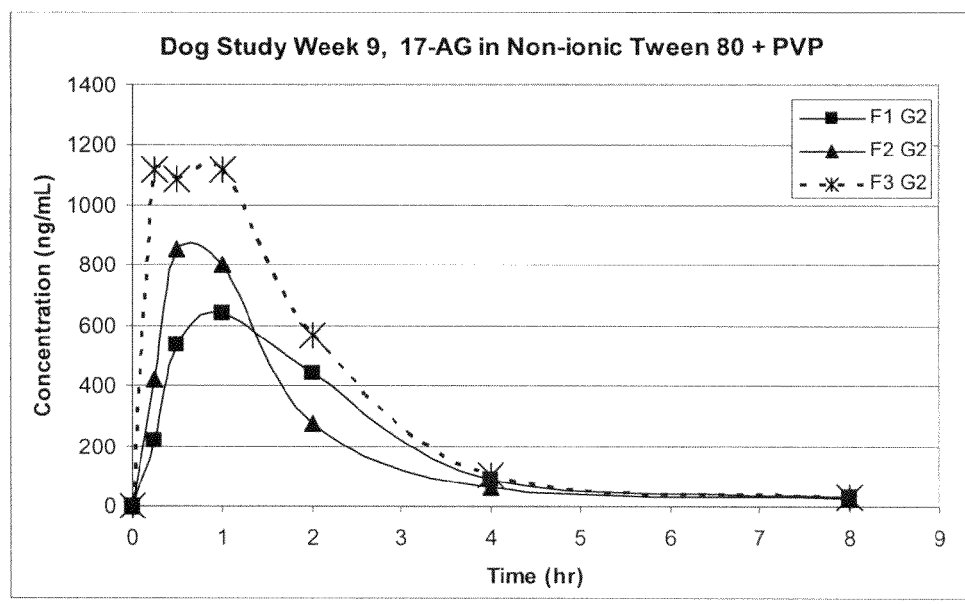
FIG. 37 depicts a graph of dog plasma level concentration after administration of 17-AG as a solution (non-ionic 2% Tween-80, 5% DMSO, 10% PVP in sterile water for injection) via oral gavage, containing a crystallization inhibitor (PVP and non-ionic Tween-80), plotted as a function of ng/ml versus time (hours).
Figures 40A, 40B, 40C:
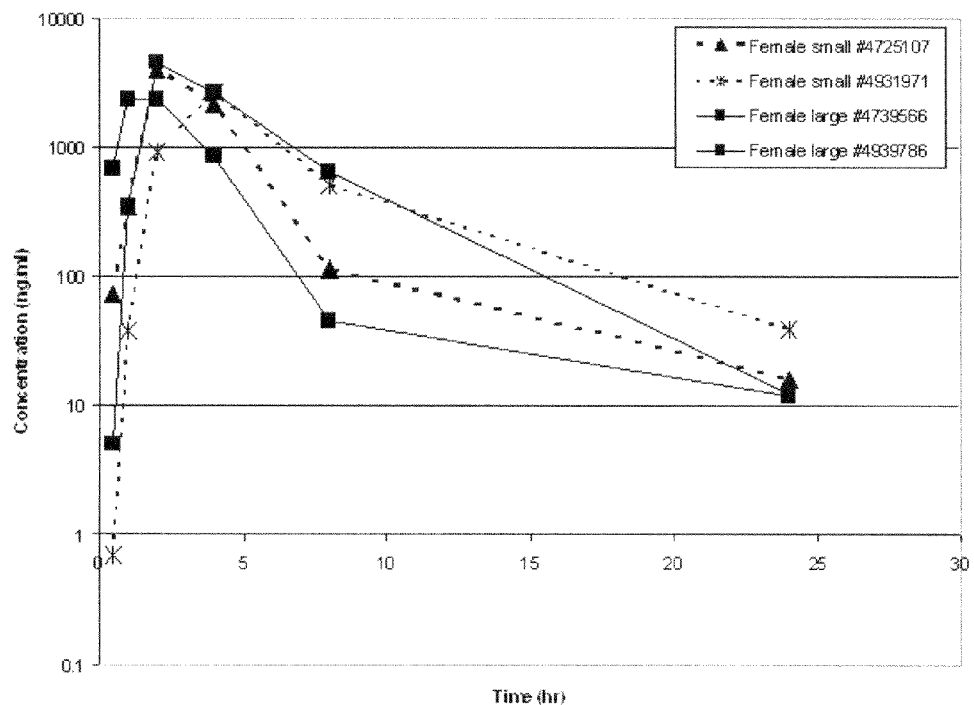
Figures 41A, 41B:
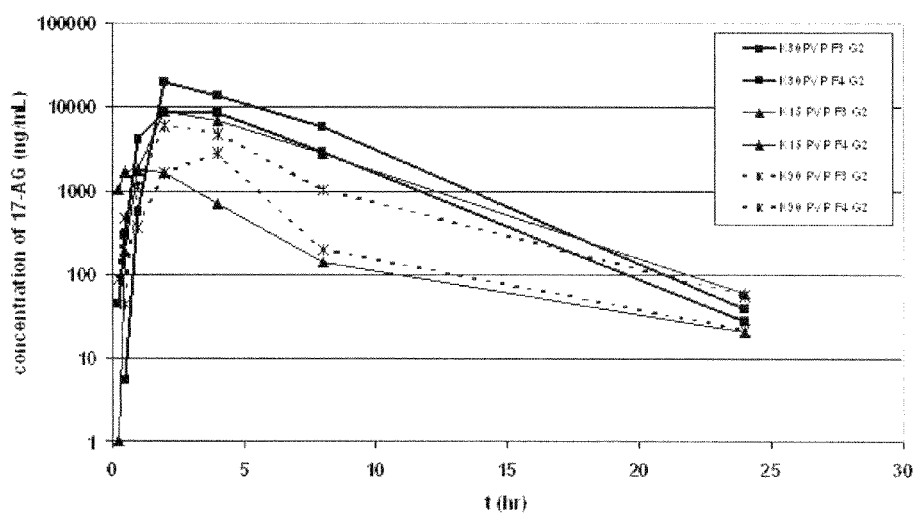
Figures 42A, 42B:
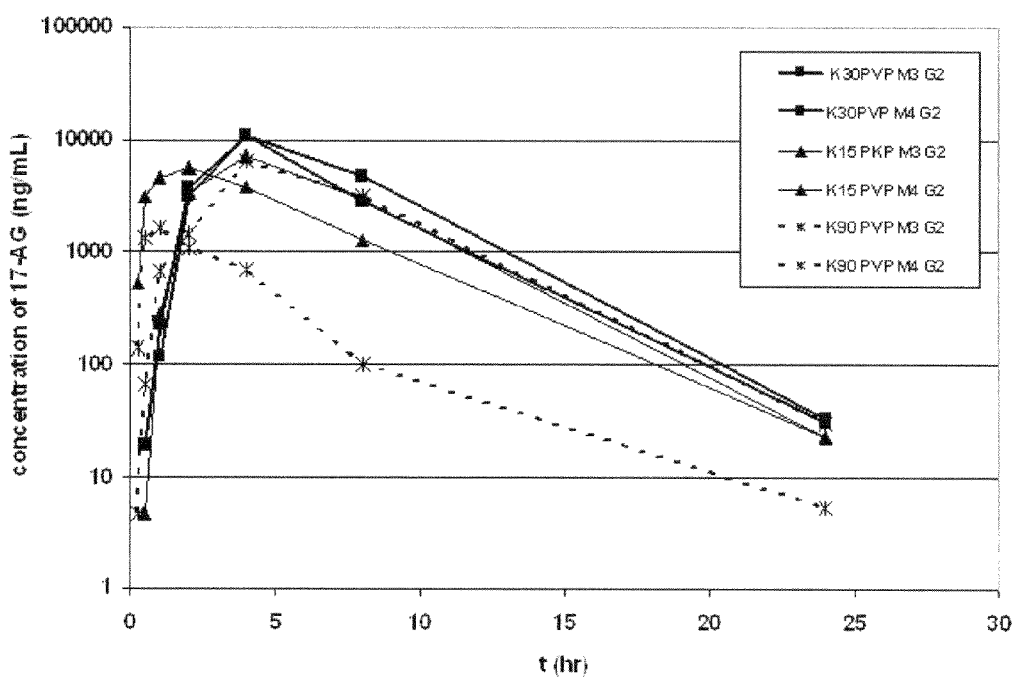
Figure 43:
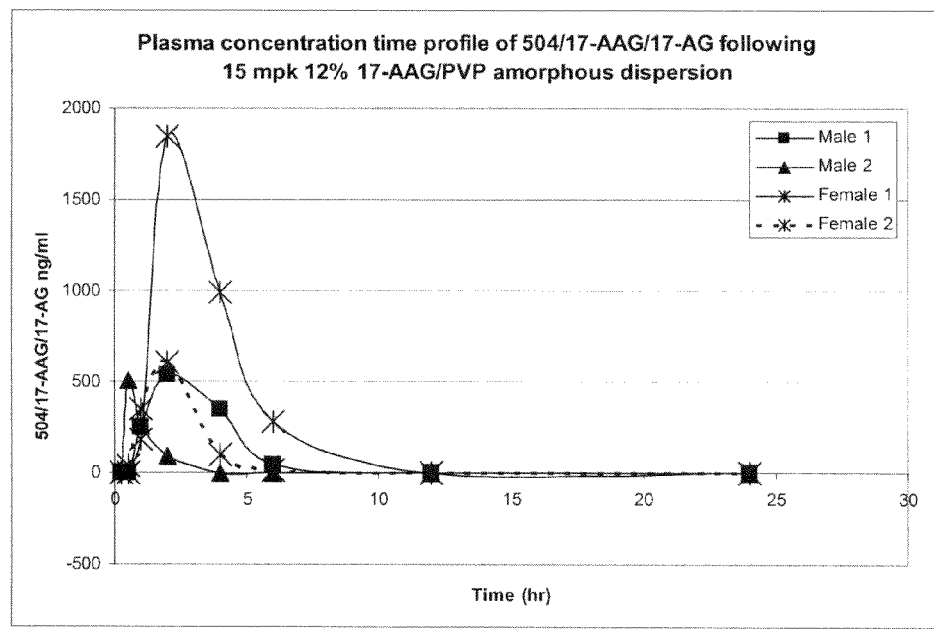
FIG. 43 depicts a graph of plasma levels achieved after a single capsule dose of an amorphous dispersion (12%17-AAG, with a crystallization inhibitor PVP in uncoated HPMC capsule) in beagle dogs, demonstrating that good in-vivo exposure can be achieved in dosing amorphous dispersions of ansamycin analogs other than 17-AG.

Summary of the oral bioavailability results (average values) reflecting various load levels are found in FIG. 28a and FIG. 29a, and accompanying summary data tables in FIG. 28b and FIG. 29b. Summary of the oral bioavailability results (average values) reflecting various PVP grades are found in FIG. 41a and FIG. 42a, and accompanying summary data tables in FIG. 41b and FIG. 42b. Summary of the oral bioavailability results (average values) reflecting various particles sizes of 20% 17-AG and PVP K-30 are found in FIG. 40a, and accompanying summary data table in FIG. 40b.

Example 26

In Vivo Exposure of Various Oral Formulations of 17-AG in Beagle Dogs

The oral bioavailability of various formulations of the compound 17-AG was investigated by making various oral formulations, dosing beagle dogs and measuring 17-AG levels in blood plasma at various time points following a single oral dose. In addition, the effect of PVP on enhancing exposure was investigated by its addition to many of the tested formulations.

In brief, different crystalline, solvated, and amorphous forms of 17-AG were dosed either as filled capsules or as suspensions. In addition, various 17-AG solutions utilizing a range of different organic, anionic, & non-ionic components were dosed by oral gavage. The different oral formulations tested are listed in the following table.

| Formulation/Dose | 17-AG dose form | Dose of 17-AG (mg) | FIG. No. Reference |
|---|---|---|---|
| 20% 17-AG + PVP K30 rotary evaporation dispersion | amorphous dispersion in capsule | 50 | 14a |
| 20% 17-AG + PVP K30 spray dried dispersion | amorphous dispersion in capsule | 50 | 14b |
| 17-AG crystalline + lactose | crystalline solid in capsule | 50 | — |
| 17-AG crystalline + PVP | crystalline solid in capsule | 50 | — |
| 17-AG Ethyl acetate solvate + lactose | crystalline solid in capsule | 50 | 30a and 30c |
| 17-AG Ethyl acetate solvate + PVP | crystalline solid in capsule | 50 | 30b and 30c |
| Amorphous 17-AG + lactose | amorphous solid in capsule | 50 | 31a and 31c |
| Amorphous 17-AG + PVP | amorphous solid in capsule | 50 | 31b and 31c |
| 2 mg/ml 17-AG in 85% PG, 10% DMSO, 5% EtOH | solution | 50 | 32 |
| 2 mg/ml 17-AG in 85% PG, 10% PVP, 5% EtOH | solution | 50 | 33 |
| 2 mg/ml 17-AG in 20% PGHS, 5% DMSO in NS | solution | 50 | 34 |
| 2 mg/ml 17-AG in 20% PGHS, 5% DMSO, 10% PVP in NS | solution | 50 | 35 |
| 2 mg/ml 17-AG in 2% Tween-80, 5% DMSO in SWFI | solution | 50 | 36 |
| 2 mg/ml 17-AG in 2% Tween-80, 5% DMSO, 10% PVP in SWFI | solution | 50 | 37 |
| 2 mg/ml 17-AG in 0.17% SLS, 5% DMSO in SWFI | solution | 50 | — |
| 2 mg/ml 17-AG in 0.17% SLS, 5% DMSO, 10% PVP in SWFI | solution | 50 | — |
| 2 mg/ml 17-AG in 10% PGHS, 2.5% DMSO, 5% Tween-80, 50% olive oil in NS | emulsion | 50 | — |
| 2 mg/ml 17-AG in 10% PGHS, 2.5% DMSO, 5% Tween-80, 5% PVP, 50% olive oil in NS | emulsion | 50 | — |
| 12% 17-AG HPMC-AS rotary evaporation dispersion | amorphous dispersion in capsule | 50 | — |

-continued

| Formulation/Dose | 17-AG dose form | Dose of 17-AG (mg) | FIG. No. Reference |
|---|---|---|---|
| 12% 17-AG Eudragit L100 rotary evaporation dispersion | amorphous dispersion in capsule | 50 | — |
| 2% 17-AG nano-suspension in 2% Tween-80 | crystalline solid in suspension | 50 | — |
| 2% 17-AG nano-suspension in 2% Tween-80, 10% PVP | crystalline solid in suspension | 50 | — |
| 2% 17-AG suspension in 1% Carboxymethylcellulose | crystalline solid in suspension | 15 mg/kg | — |

The crystalline, solvated, and amorphous forms of 17-AG were made as previously described and blended with either anhydrous lactose or PVP in a Turbula blender for 15 minutes.

Solutions were made by adding the formulation components to the desired percentage by weight and either adding 17-AG to the desired concentration of 2 mg/ml until dissolved or by adding a stock solution of 40 mg/ml 17-AG in DMSO and diluting 1:20 to achieve the final concentration of 2 mg/ml. All solutions were clear and purple in color without any evidence of precipitate.

Figure 46:
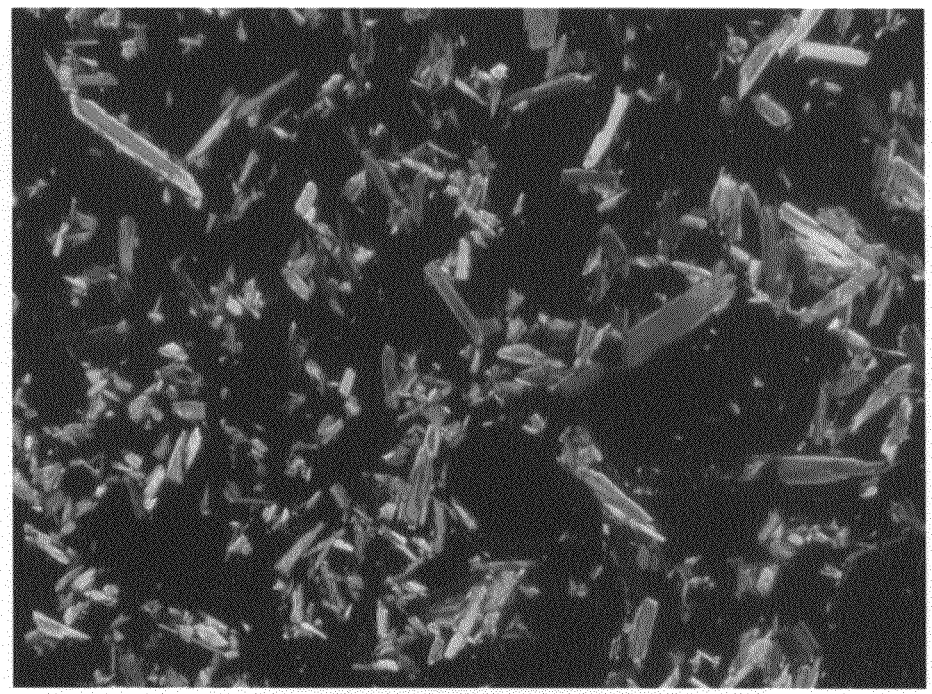
FIG. 46 depicts exemplary photo images of a suspension and an emulsion: (A) 2% 17-AG suspension in 1% Carboxymethylcellulose; and (B) 2 mg/ml 17-AG in 10% PGHS, 2.5% DMSO, 5% Tween-80, 50% olive oil in NS.
Figure 46:
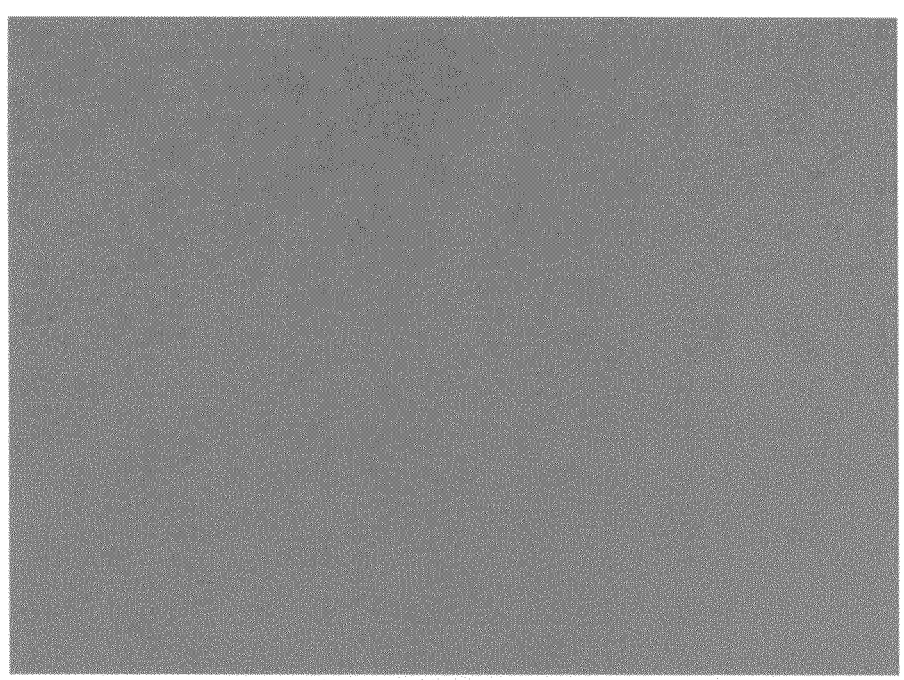

The suspension in carboxymethylcellulose was made by levigating crystalline 17-AG with glycerol in a mortar and pestle followed by homogenization in the 1% carboxymethylcellulose solution in a high speed homogenizer for 10 minutes. Homogeneity of the suspension was checked by microscopy. FIG. 46(A) is an exemplary photo of a suspension of 17-AG, in 1% carboxymethylcellulose.

The emulsions were made by making a 4 mg/ml solution of 17-AG in either 10% PGHS/2.5% DMSO/5% Tween-80 or 10% PGHS/2.5% DMSO/5% Tween-80/5% PVP, combining the solution 1 to 1 with olive oil followed by mixing in a high speed homogenizer for 15 minutes. Confirmation of the emulsion was performed by microscopy. FIG. 46(B) is an exemplary photo of an emulsion of 17-AG, in 10% PGHS, 2.5% DMSO, 5% Tween-80, 50% olive oil, in NS.

The nanosuspension was made by levigating crystalline 17-AG by high shear in a microfluidizer (Microfluidics Corp, Model: M-110L) for 10-20 minutes in Tween-80. Mean particle size (d50: 300-400 nM) was measured by laser light diffraction (Malvern Corp, Mastersizer 2000).

All dosed formulations had at least 2 hours physical stability at room temperature.

Blood was collected pre-dose, 15, 30 minutes, 1, 2, 4, and 8 hours post-dose into tubes containing sodium heparin. Collected blood samples were immediately placed on wet ice and refrigerated centrifuge for isolation of plasma within 30 min of collection. Isolated plasma was saved in labeled screw cap freezer vials or eppendorf tubes and stored frozen (−70° C.) until analyzed for plasma 17-AG levels. The design of the study is as follows. Two groups of dogs, each group consisting of 3 females were utilized for dosing, with a week washout in between each dose.

| | Group A | Group B |
|---|---|---|
| Study 1 | 20% 17-AG PVP K30, rotary evaporation | |
| Study 2 | 17-AG + Lactose | |
| Study 3 | 17-AG + PVP K30 | |
| Study 4 | 17-AG EtOAc Solvate + Lactose | |
| Study 5 | 20% 17-AG PVP K30, spray dried dispersion | 17-AG EtOAc Solvate + PVP |
| Study 6 | Amorphous 17-AG + Lactose | Organic PG/EtOH + DMSO solution |
| Study 7 | Amorphous 17-AG + PVP | Organic PG/EtOH + PVP solution |
| Study 8 | PEG-HS solution | Non-ionic Tween 80 solution |
| Study 9 | PEG-HS + PVP solution | Non-ionic Tween 80 + PVP solution |
| Study 10 | Anionic mic SLS solution | Oil Emulsion |
| Study 11 | Anionic mic SLS + PVP solution | Oil Emulsion + PVP |
| Study 12 | 20% 17-AG HPMC-AS dispersion | |
| Study 13 | 20% 17-AG Eudragit L100 dispersion | |
| Study 14 | Nano suspension | |
| Study 15 | Nano suspension + PVP | |

For the solid formulations, PVP does not appear to enhance exposure for the physical mixes of crystalline 17-AG and PVP to a level where 17-AG can be detected. However, there was low exposure after dosing the EtOAc Solvate of 17-AG, and significant exposure after dosing amorphous 17-AG or amorphous dispersions of 17-AG. Moreover, the inclusion of PVP to these formulations appears to improve the exposure profiles of the EtOAc Solvate and amorphous 17-AG. This result is consistent with the in-vitro dissolution experiments demonstrating the ability of PVP to enhance 17-AG solubility and stabilize supersaturated solutions of 17-AG. Method of manufacture does not appear to have an effect since the exposure from dosing either solvent evaporated or spray dried 20% 17-AG/PVP amorphous dispersion is the same. Also consistent with the results from the 17-AG/PVP dispersions are the in-vivo results from dosing solid dispersions of 17-AG with other crystallization inhibitors, HPMC-AS and Eudragit L100. The improved bioavailability of 17-AG from these formulations as compared to dosing crystalline 17-AG demonstrates the utility of utilizing crystallization inhibitors in amorphous dispersion with geldanamycin analogs.

For the liquid (solution, emulsion) formulations, there was a significant exposure for all of the formulations dosed. Inclusion of PVP in the formulation did not appear to have the same significant effect in the solution doses as it did in the solid dose exposure results. This could be due to the fact that all of the solutions were dosed at a relatively low concentration (2 mg/ml) and small volume (25 ml), and had good physical stability. The consistently high exposure results for all of the solution doses would suggest that 17-AG is being readily absorbed before PVP could demonstrate its ability to stabilize the solution.

For the suspension and nano-suspension formulations, there was little or no measurable level of 17-AG following dosing, either with or without the crystallization inhibitor PVP.

In total, these results demonstrate the ability to dose 17-AG utilizing a wide range of oral formulations. Any variability observed in the exposure is most likely due to animal specific differences or in-life observations (i.e. dosing issues, emesis). Exemplary graphs of the exposure data for specific doses are found in the Figure No. References as specified in the table below. A summary of the oral bioavailability results (average values) is found in the following table:

Example 27

In-Vivo Efficacy of 17-AG

In-vivo efficacy of 17-AG was demonstrated by conducting in 2 mouse xenograph studies utilizing mouse xenograph tumor models of client proteins dependent upon HSP90.

In the first study, H1975, a non-small cell lung cancer cell line which contains L858R and T790M mutations in EGFR, a client protein for HSP90 was utilized. 5-6 week old Nu/Nu mice were implanted with 10×10e6H1975 cells. Dosing commenced after implanted cells reached ~150 mm3. Dosing was by oral gavage and the dosing schedule was every other day with vehicle (20% PGHS, 5% DMSO, 75% NS), and 75 mg/kg, and 100 mg/kg 17-AG in vehicle. After dosing, ~35% and ~70% reduction in tumor volume was seen in the dosing

| Formulation/Dose | Half Life (h) | $T_{max}$ (h) | $C_{max}$ (ng/ml) | AUC INF (ng * hr/ml) | FIG. No. Reference |
|---|---|---|---|---|---|
| 20% 17-AG + PVP K30 rotary evaporation dispersion | 1.5 | 1.8 | 1176.2 | 3153.0 | 14a |
| 20% 17-AG + PVP K30 spray dried dispersion | 1.2 | 1.7 | 1450.0 | 3011.3 | 14b |
| 17-AG crystalline + lactose | C.N.E. | C.N.E. | BLQ | C.N.E. | |
| 17-AG crystalline + PVP | C.N.E. | C.N.E. | BLQ | C.N.E. | |
| 17-AG Ethyl acetate solvate + lactose | 2.7 | 0.7 | 98.1 | 239.0 | 30a and 30c |
| 17-AG Ethyl acetate solvate + PVP | 3.2 | 1.0 | 124.4 | 322.2 | 30b and 30c |
| Amorphous 17-AG + lactose | 1.5 | 1.0 | 942.3 | 1854.4 | 31a and 31c |
| Amorphous 17-AG + PVP | 1.3 | 1.2 | 1141.3 | 2594.2 | 31b and 31c |
| 2 mg/ml 17-AG in 85% PG, 10% DMSO, 5% EtOH solution | 1.3 | 2.0 | 2170.0 | 4937.1 | 32 |
| 2 mg/ml 17-AG in 85% PG, 10% PVP, 5% EtOH solution | 1.4 | 1.7 | 1696.7 | 4454.4 | 33 |
| 2 mg/ml 17-AG + 20% PGHS, 5% DMSO in NS solution | 1.4 | 1.2 | 908.3 | 2894.3 | 34 |
| 2 mg/ml 17-AG + 20% PGHS, 5% DMSO, 10% PVP in NS solution | 1.5 | 1.2 | 761.3 | 2512.8 | 35 |
| 2 mg/ml 17-AG in 2% Tween-80, 5% DMSO in SWFI solution | 1.5 | 0.8 | 1393.3 | 3915.6 | 36 |
| 2 mg/ml 17-AG in 2% Tween-80, 5% DMSO, 10% PVP in SWFI solution | 1.5 | 0.6 | 871.3 | 2116.6 | 37 |
| 2 mg/ml 17-AG in 0.17% SLS, 5% DMSO in SWFI solution | 1.2 | 1.0 | 2362 | 6090 | — |
| 2 mg/ml 17-AG in 0.17% SLS, 5% DMSO, 10% PVP in SWFI solution | 1.4 | 0.4 | 1788 | 3300 | — |
| 2 mg/ml 17-AG in 10% PGHS, 2.5% DMSO, 5% Tween-80, 50% olive oil in NS emulsion | 1.3 | 0.9 | 1011 | 2923 | — |
| 2 mg/ml 17-AG in 10% PGHS, 2.5% DMSO, 5% Tween-80, 5% PVP, 50% olive oil in NS emulsion | 1.6 | 0.5 | 765 | 2394 | — |
| 12% 17-AG HPMC-AS rotary evaporation dispersion | 1.19 | 2 | 2133 | 6901 | — |
| 12% 17-AG Eudragit L100 rotary evaporation dispersion | 1.6 | 0.5 | 765 | 2394 | — |
| 2% 17-AG nano-suspension in 2% Tween-80 | C.N.E. | 0.25 | 5.27 | C.N.E. | — |
| 2% 17-AG nano-suspension in 2% Tween-80, 10% PVP | C.N.E. | 0.50 | 8.50 | C.N.E. | — |
| 2% 17-AG suspension in 1% Carboxymethylcellulose | C.N.E. | C.N.E. | BLQ | C.N.E. | — |

CNE = cannot estimate.

Figure 47:
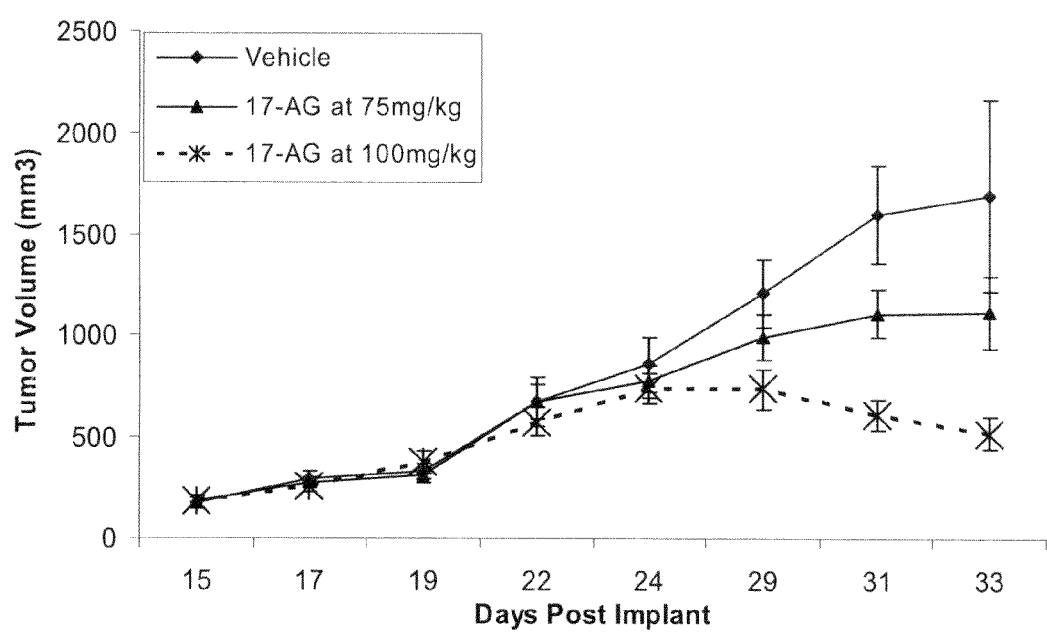
FIG. 47 depicts a graph showing tumor volume as a function of time (days) utilizing a mouse xenograph model H1975 when dosed using a solution of 17-AG in 20% PG-HS, 5% DMSO and 75% normal saline.
Figure 48:
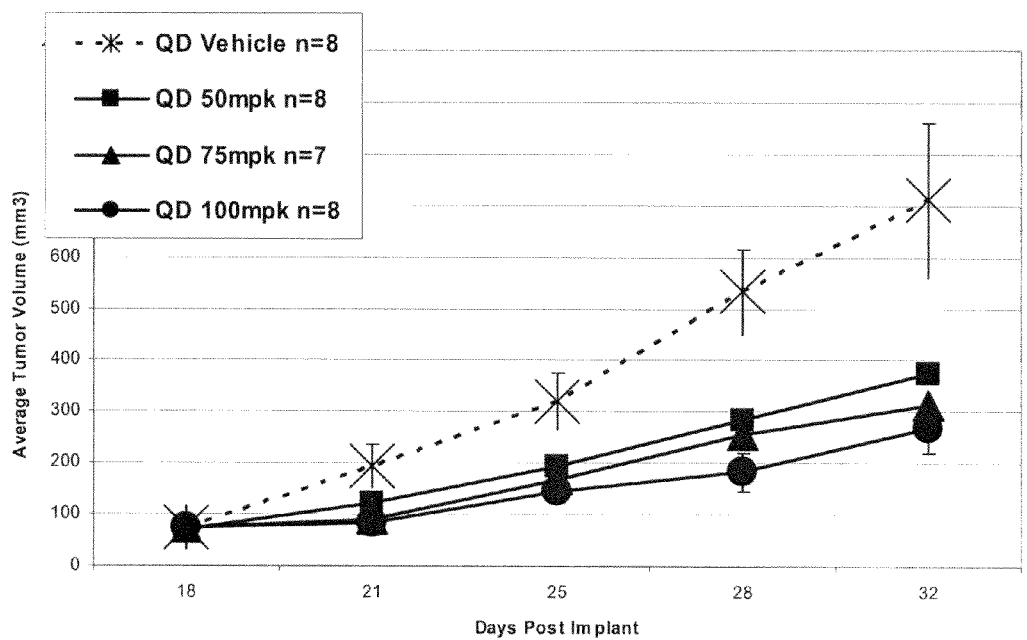
FIG. 48 depicts a graph showing tumor volume as a function of time (days) utilizing a mouse xenograph model H1650 when dosed using a solution of 17-AG in 15% PVP, 5% ethanol and 80% propylene glycol.

Following Example 27 illustrates that 17-AG as a solution reduces tumor growth in a mouse xenograph model. Representative data are found in FIG. 47 and FIG. 48.

arms as compared to vehicle treated animals demonstrating efficacy of dosing 17-AG in a xenograph tumor model dependent upon an HSP90 client protein.

In the second study, H1650 lung adenocarcinoma cell line which contains a mutant form of EGFR (Del E746-A750) was utilized. 5-6 week old Nu/Nu mice were implanted with 10×10e6H1650 cells. Dosing commenced after implanted cells reached ~100 mm3. Dosing was by oral gavage and the dosing schedule was every day with vehicle (15% PVP, 5% EtOH, 80% PG), and 50 mg/kg, 75 mg/kg, and 100 mg/kg 17-AG in vehicle. After dosing, 62% maximum reduction in tumor volume was seen in the dosing arms as compared to vehicle treated animals demonstrating efficacy of dosing 17-AG in a xenograph tumor model dependent upon on an HSP90 client protein.

Other embodiments included herein are provided in the following claims.

We claim:

1. A polymorph Form I of 17-amino-geldanamycin characterized by XRPD peaks at 6.2±0.3, 8.5±0.3, 13.6±0.3 and 15.9±0.3 degrees 2-theta.

2. The polymorph according to claim 1, wherein it has XRPD peaks at 16.9±0.3, 22.4±0.3, 23.4±0.3, 26.3±0.3, 30.6±0.3, 31.7±0.3, 35.1±0.3 and 36.1±0.3 degrees 2-theta.

3. The polymorph according to claim 1, characterized in that it has substantially all peaks in its XRPD pattern shown in FIG. 2.

4. A polymorph Form II of 17-amino-geldanamycin characterized by XRPD peaks at 12.5±0.3, 15.1±0.3, 20.7±0.3, 22.4±0.3 and 25.0±0.3 degrees 2-theta.

5. The polymorph according to claim 4, wherein it has XRPD peaks at 9.5±0.3, 10.1±0.3, 16.1±0.3, 16.8±0.3, 19.8±0.3, 21.5±0.3, 25.8±0.3, 29.5±0.3 and 30.5±0.3 degrees 2-theta.

6. The polymorph according to claim 4 characterized in that it has substantially all peaks in its XRPD pattern shown in FIG. 5.

7. A polymorph Form III of 17-amino-geldanamycin characterized by XRPD peaks at 18.3±0.3, 21.0±0.3, and 24.3±0.3 degrees 2-theta.

8. The polymorph according to claim 7, characterized by XRPD peaks at 8.4±0.3, 9.3±0.3, 10.9±0.3, 11.6±0.3, 13.6±0.3, 13.9±0.3, 15.7±0.3, 16.3±0.3, 17.1±0.3, 18.3±0.3, 18.6±0.3, 19.9±0.3, 21.0±0.3, 22.0±0.3, 24.3±0.3, 25.8±0.3, 28.2±0.3, 29.2±0.3, and 30.8±0.3 degrees 2-theta.

9. The polymorph according to claim 7 characterized in that it has substantially all peaks in its XRPD pattern shown in FIG. 6.

10. An ethyl acetate solvate of 17-amino-geldanamycin.

11. The solvate according to claim 10 characterized by XRPD peaks at 8.2±0.3, 15.9±0.3 and 22.3±0.3 degrees 2-theta.

12. The solvate according to claim 11 characterized by at least one other peak selected from those at 6.2±0.3, 8.2±0.3, 12.6±0.3, 14.5±0.3, 15.9±0.3, 16.8±0.3, 17.5±0.3, 22.3±0.3, 23.3±0.3 and 25.3±0.3 degrees 2-theta.

13. The solvate according to claim 10 characterized in that it has substantially all peaks in its XRPD pattern shown in FIG. 7.

* * * * *